United States Patent
Lounsbury

(10) Patent No.: US 11,918,633 B2
(45) Date of Patent: Mar. 5, 2024

(54) COMPOSITIONS OF PROKARYOTIC PHENYLALANINE AMMONIA-LYASE AND METHODS OF TREATING ADOLESCENT SUBJECTS

(71) Applicant: BIOMARIN PHARMACEUTICAL INC., Novato, CA (US)

(72) Inventor: Debra Lounsbury, San Francisco, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

(21) Appl. No.: 17/747,697

(22) Filed: May 18, 2022

(65) Prior Publication Data
US 2022/0370576 A1 Nov. 24, 2022

Related U.S. Application Data

(60) Provisional application No. 63/190,567, filed on May 19, 2021.

(51) Int. Cl.
*C12N 9/88* (2006.01)
*A61K 38/51* (2006.01)
*A61P 3/00* (2006.01)

(52) U.S. Cl.
CPC ............... *A61K 38/51* (2013.01); *A61P 3/00* (2018.01); *C12Y 403/01024* (2013.01)

(58) Field of Classification Search
None
See application file for complete search history.

(56) References Cited

U.S. PATENT DOCUMENTS

| | | | |
|---|---|---|---|
| 7,531,341 B1 | 5/2009 | Vellard et al. | |
| 7,534,595 B2 | 5/2009 | Vellard et al. | |
| 7,537,923 B2 | 5/2009 | Kakkis et al. | |
| 7,560,263 B2 | 7/2009 | Kakkis et al. | |
| 7,790,433 B2 | 9/2010 | Kakkis et al. | |
| 9,557,340 B2 | 1/2017 | Foehr et al. | |
| 10,221,408 B2 | 3/2019 | Okhamafe et al. | |
| 11,505,790 B2 | 11/2022 | Okhamafe et al. | |
| 2008/0008695 A1* | 1/2008 | Vellard | A61P 25/00 435/232 |
| 2009/0047268 A1 | 2/2009 | Kakkis et al. | |
| 2009/0263369 A1 | 10/2009 | Kakkis et al. | |
| 2009/0047265 A1 | 12/2009 | Kakkis et al. | |
| 2010/0278802 A1 | 11/2010 | Kakkis et al. | |
| 2011/0201022 A1 | 8/2011 | Foehr et al. | |
| 2013/0039898 A1 | 2/2013 | Okhamafe et al. | |
| 2016/0139144 A1 | 5/2016 | Foehr et al. | |
| 2016/0362675 A1 | 12/2016 | Okhamafe et al. | |
| 2019/0345475 A1 | 11/2019 | Okhamafe et al. | |

FOREIGN PATENT DOCUMENTS

| | | |
|---|---|---|
| WO | WO 2008153776 A1 | 12/2008 |
| WO | WO 2009025760 A2 | 2/2009 |
| WO | WO 2009025760 A3 | 2/2009 |
| WO | WO 2010014225 A2 | 2/2010 |
| WO | WO 2010014225 A3 | 2/2010 |
| WO | WO 2011097335 A2 | 8/2011 |
| WO | WO 2011097335 A3 | 8/2011 |

OTHER PUBLICATIONS

Karlie C. Mahan et al Pegvaliase: a novel treatment option for adults with phenylketonuria (Year: 2019).*
European Medicines Agency (https://www.ema.europa.eu/en/documents/product-information/palynziq-epar-product-information_en.pdf—date of first authorization May 3, 2019) (Year: 2019).*
International Searching Authority, International Search Report and Written Opinion for International Patent Application No. PCT/US2022/029806 (Pub No. WO 2022245924) dated Oct. 5, 2022 (12 pages).

* cited by examiner

*Primary Examiner* — Tekchand Saidha
(74) *Attorney, Agent, or Firm* — JONES DAY

(57) ABSTRACT

Phenylalanine ammonia-lyase (PAL) variants with a greater phenylalanine-converting activity and/or a reduced immunogenicity as compared to a wild-type PAL for therapeutic uses, including the treatment of adolescent subjects having PKU.

16 Claims, 12 Drawing Sheets

Figure 1A:
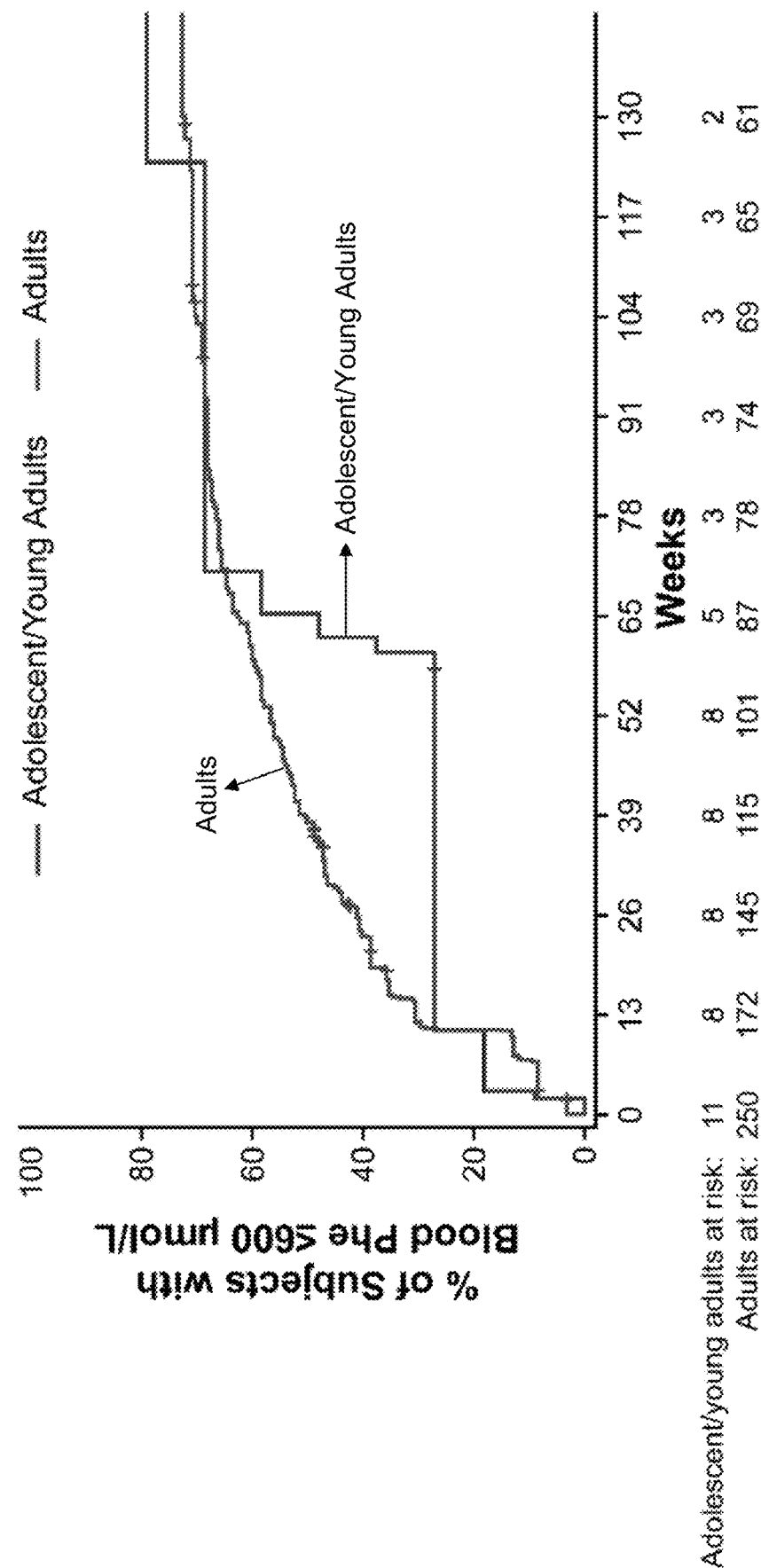

Specification includes a Sequence Listing.

FIG. 3

| Assessment [a] | Study Week Screen[h] | 1 | 2 | 3 | 4 | 5 | 6 | 7 | 8 | 9 | 13 | 17 | 21 | 25 | 29 | 33 | 37 | 41 | 45 | 49 | 53 | 57 | 61 | 65 | 69 | 73 | HRV | SC/ET |
|---|---|---|---|---|---|---|---|---|---|---|---|---|---|---|---|---|---|---|---|---|---|---|---|---|---|---|---|---|
| Study Day | -28/1 | 1 | 8 | 15 | 22 | 29 | 36 | 43 | 50 | 57 | 85 | 113 | 141 | 169 | 197 | 225 | 253 | 281 | 309 | 337 | 365 | 393 | 421 | 449 | 477 | 505 | | |
| Informed consent | X | | | | | | | | | | | | | | | | | | | | | | | | | | | | |
| Self-administration training[c] | | X | | | | | | | | | | | | | | | | | | | | | | | | | | | |
| Study drug observer training[d] | X | | | | | | | | | | | | | | | | | | | | | | | | | | | | |
| Demographics | X | | | | | | | | | | | | | | | | | | | | | | | | | | | | |
| Medical history[e] | X | | | | | | | | | | | | | | | | | | | | | | | | | | | | |
| HIV, hepatitis B and C screens[f] | X | | | | | | | | | | | | | | | | | | | | | | | | | | | | |
| 12 lead ECG | X | | | | | | | | | | | | | | | | | | | | | | | | | | | X | |
| Physical examination | X | X | X | X | X | X | X | X | X | X | X | X | X | X | X | X | X | X | X | X | X | X | X | X | X | X | | X |
| Vital signs | X | X | X | X | X | X | X | X | X | X | X | X | X | X | X | X | X | X | X | X | X | X | X | X | X | X | X | X |
| Weight | X | X | X | X | X | X | X | X | X | X | X | X | X | X | X | X | X | X | X | X | X | X | X | X | X | X | | X |
| Clinical safety laboratory tests[g] | X | X | X | X | X | X | X | X | X | X | X | X | X | X | X | X | X | X | X | X | X | X | X | X | X | X | X | X |
| C-reactive protein | X | X | X | | | | | | | X | X | X | X | X | X | X | X | X | X | X | X | X | X | X | X | X | | X |
| Erythrocyte sedimentation rate[h] | X | | | | | | | | | | | | | | | | | | | | | | | | | | | X |
| Serum cortisol[i] | X | X | | | | | | | | | | | | X | | | | | | X | | | | | | X | | X |
| Complements C3 and C4 | X | X | | | | X | | | | | | | X | | X | | | X | | X | | X | | X | | X | X | X |
| Tryptase | | X | | | | | | | | | | | | | | | | | | | | | | | | | | X |
| Urine albumin/creatinine ratio[j] | X | | | | | | | | | | | X | | X | | | | X | | X | | X | | X | | X | X | X |
| Urine pregnancy test[k] | X | X | X | X | X | X | X | X | X | X | X | X | X | X | X | X | X | X | X | X | X | X | X | X | X | X | X | X |
| 3-day diet diary[l] | X | X | | | | X | X | X | | X | X | X | X | X | X | X | X | X | X | X | X | X | X | X | X | X | | X |
| PK (plasma pegvaliase)[m] | | X | | | | X | | | | X | X | X | X | X | X | X | X | X | X | X | X | X | X | X | X | X | | X |
| Plasma Phe, tyrosine[n] | X[b] | X | X | X | X | X | X | X | X | X | X | X | X | X | X | X | X | X | X | X | X | X | X | X | X | X | | X |
| Immunogenicity assessments[o] | X | X | | | | X | X | X | | X | X | X | X | X | X | X | X | X | X | X | X | X | X | X | X | X | | X |
| ADHD-RS IV[p] | X | X | | | | | | | | | X | | | X | | | X | | X | X | | X | | X | | X | X[o] | X |
| BRIEF[q] | X | X | | | | | | | | | X | | | X | | | X | | X | X | | X | | X | | X | | X |
| Weekly call (non-visit weeks)[r] | | | | | | | | | | | | | | | | | | | | | | | | | | | | |
| Adverse events[s] | | X | X | X | X | X | X | X | X | X | X | X | X | X | X | X | X | X | X | X | X | X | X | X | X | X | X | X |
| Concomitant medication[s] | X | X | X | X | X | X | X | X | X | X | X | X | X | X | X | X | X | X | X | X | X | X | X | X | X | X | X | X |
| Administer study drug[t] | | X | X | X | X | X | X | X | X | X | X | X | X | X | X | X | X | X | X | X | X | X | X | X | X | X | | X |

| Assessment [a] | Study Week | 73[b] | 81 | 89 | 97 | 105 | 113 | 121 | 129 | 137 | 145 | 153 | HRV | SC/ET |
|---|---|---|---|---|---|---|---|---|---|---|---|---|---|---|
| | Study Day | 505 | 561 | 617 | 673 | 729 | 785 | 841 | 897 | 953 | 1009 | 1065 | | |
| Study drug observer training [c] | | | | | | | | | | | | | | |
| 12 lead ECG | | | | | | | | | | | | X | | X |
| Physical examination | | X | X | X | X | X | X | X | X | X | X | X | | X |
| Vital signs | | X | X | X | X | X | X | X | X | X | X | X | | X |
| Weight | | X | X | X | X | X | X | X | X | X | X | X | | X |
| Clinical safety laboratory tests [d] | | X | X | X | X | X | X | X | X | X | X | X | | X |
| C-reactive protein | | X | X | X | X | X | X | X | | | | | | X |
| Erythrocyte sedimentation rate [e] | | X | | | | | | | | | | X | | X |
| Serum cortisol [f] | | X | | | X | | | X | | | | | | |
| Complements C3 and C4 | | X | X | X | X | X | X | X | X | X | X | X | | X |
| Tryptase | | | | | | | | | | | | | X | |
| Urine albumin/creatinine ratio [g] | | X | X | X | X | X | X | X | X | X | X | X | X | X |
| Urine pregnancy test [h] | | X | X | X | X | X | X | X | X | X | X | X | | X |
| 3-day diet diary [i] | | X | X | X | X | X | X | X | X | X | X | X | | X |
| PK (plasma pegvaliase) [j] | | X | X | X | X | X | X | X | X | X | X | X | | X |
| Plasma Phe, tyrosine [k] | | X | X | X | X | X | X | X | X | X | X | X | | X |
| Immunogenicity assessments [l] | | X | X | X | X | X | X | X | X | X | X | X | X[1] | X |
| ADHD-RS IV [m] | | X | | X | | X | | X | | X | | X | | X |
| BRIEF [n] | | X | | X | | X | | X | | X | | X | | X |
| Weekly call (non-visit weeks) [o] | | | | | | | | | | | | | | |
| Adverse events [p] | | X | X | X | X | X | X | X | X | X | X | X | X | X |
| Concomitant medication [p] | | X | X | X | X | X | X | X | X | X | X | X | X | X |
| Administer study drug [q] | | X | X | X | X | X | X | X | X | X | X | X | | |

FIG. 4

| Study Week | Screen[b] | 1 | 2 | 3 | 4 | 5 | 6 | 7 | 8 | 9 | 13 | 17 | 21 | 25 | 29 | 33 | 37 | 41 | 45 | 49 | 53 | 57 | 61 | 65 | 69 | 73 | HRV | SC/ET |
|---|---|---|---|---|---|---|---|---|---|---|---|---|---|---|---|---|---|---|---|---|---|---|---|---|---|---|---|---|
| Study Day | -28/1 | 1 | 8 | 15 | 22 | 29 | 36 | 43 | 50 | 57 | 85 | 113 | 141 | 169 | 197 | 225 | 253 | 281 | 309 | 337 | 365 | 393 | 421 | 449 | 477 | 505 | | |
| Assessment[a] | | | | | | | | | | | | | | | | | | | | | | | | | | | | |
| Informed consent | X | | | | | | | | | | | | | | | | | | | | | | | | | | | |
| Self-administration training[c] | | | | | | | | | | | | | | | | | | | | | | | | | | X | | |
| Study drug observer training[d] | | | | | | | | | | | | | | | | | | | | | | | | | | X | | |
| Demographics | X | | | | | | | | | | | | | | | | | | | | | | | | | | | |
| Medical history (allergy, PKU)[e] | X | | | | | | | | | | | | | | | | | | | | | | | | | | | |
| HIV, hepatitis B and C screens[f] | X | | | | | | | | | | | | | | | | | | | | | | | | | | | |
| 12 lead ECG | X | | | | | | | | | | | | | | | | | | | | | | | | | X | | X |
| Physical examination | X | X | X | X | X | X | X | X | X | X | X | X | X | X | X | X | X | X | X | X | X | X | X | X | X | X | | X |
| Vital signs | X | X | X | X | X | X | X | X | X | X | X | X | X | X | X | X | X | X | X | X | X | X | X | X | X | X | X | X |
| Weight | X | X | X | X | X | X | X | X | X | X | X | X | X | X | X | X | X | X | X | X | X | X | X | X | X | X | X | X |
| Clinical safety laboratory tests[g] | X | X | X | X | X | X | X | X | X | X | X | X | X | X | X | X | X | X | X | X | X | X | X | X | X | X | X | X |
| C-reactive protein | X | X | | | | | | | | X | X | X | X | X | X | X | X | X | X | X | X | X | X | X | X | X | | X |
| Erythrocyte sedimentation rate[h] | X | | | | | | | | | | | | | | | | | | | | | | | | | | | X |
| Serum cortisol[i] | X | X | | | | | | | | | | | | X | | | | | | X | | X | | | | | | X |
| Complements C3 and C4 | X | X | | | | | | | | | | | X | X | | X | | X | | X | | X | | X | | X | | X |
| Tryptase | X | X | | | | | | | | | | | | | | | | | | | | | | | | | X | |
| Urine albumin/creatinine ratio[j] | | X | | | | | | | | | X | X | X | X | X | X | X | X | X | X | X | X | X | X | X | X | | X |
| Urine pregnancy test[k] | X | X | X | X | X | X | X | X | X | X | X | X | X | X | X | X | X | X | X | X | X | X | X | X | X | X | | X |
| 3-day diet diary[l] | | X | X | | | X | | | | | | | | | | | | | | | | | | | | | | |
| Plasma Phe, tyrosine[m] | X[b] | X | X | X | X | X | X | X | X | X | X | X | X | X | X | X | X | X | X | X | X | X | X | X | X | X | | X |
| ADHD-RS IV[n] | | X | | | | | | | | | X | | | X | | X | | X | | X | | X | | X | | X | | X |
| BRIEF[o] | | X | | | | | | | | | | | | X | | X | | X | | X | | X | X | | | X | | X |
| Weekly call (non-visit weeks)[p] | | | | | | | | | | | | | | | | | | | | | | | | | | | | |
| Adverse events[q] | | X | X | X | X | X | X | X | X | X | X | X | X | X | X | X | X | X | X | X | X | X | X | X | X | X | X | X |
| Concomitant medication[q] | X | X | X | X | X | X | X | X | X | X | X | X | X | X | X | X | X | X | X | X | X | X | X | X | X | X | X | X |

FIG. 5

FIG. 6

| Assessment [a] | Study Week | 73[b] | 74 | 75 | 76 | 77 | 78 | 79 | 80 | 81 | 85 | 89 | 93 | 97 | 101 | 105 | 109 | 113 | 117 | 121 | 125 | 129 | 133 | 137 | 141 | 145 | HRV | SC/ET |
|---|---|---|---|---|---|---|---|---|---|---|---|---|---|---|---|---|---|---|---|---|---|---|---|---|---|---|---|---|
| | Study Day | 505 | 512 | 519 | 526 | 533 | 540 | 547 | 554 | 561 | 589 | 617 | 645 | 673 | 701 | 729 | 757 | 785 | 813 | 841 | 869 | 897 | 925 | 953 | 981 | 1009 | | |
| Self-administration training [c] | | X | | | | | | | | | | | | | | | | | | | | | | | | | | |
| Study drug observer training [d] | | X | | | | | | | | | | | | | | | | | | | | | | | | | | |
| 12 lead ECG | | X | | | | | | | | | | | | | | | | | | | | | | | | | | X |
| Physical examination | | X | X | | X | X | X | X | X | X | X | X | X | X | X | X | X | X | X | X | X | X | X | X | X | X | | X |
| Vital signs | | X | X | X | X | X | X | X | X | X | X | X | X | X | X | X | X | X | X | X | X | X | X | X | X | X | | X |
| Weight | | X | X | X | X | X | X | X | X | X | X | X | X | X | X | X | X | X | X | X | X | X | X | X | X | X | | X |
| Clinical safety laboratory tests [e] | | X | X | X | X | X | | | | X | X | X | X | X | X | X | X | X | X | X | X | X | X | X | X | X | | X |
| C-reactive protein | | X | | | | | | | | X | | X | | X | | X | | X | | X | | X | | X | | X | | X |
| Erythrocyte sedimentation rate [f] | | X | | | | | | | | | | | | | | | | | | | | | | | | | | X |
| Serum cortisol [g] | | X | | | | | | | | | | | | X | X | | | | | X | | | | | | X | | X |
| Complements C3 and C4 | | X | | | | X | | | | X | | X | | X | | X | | X | | X | | X | | X | | X | | X |
| Tryptase | | X | | | | | | | | | | | | | | | | | | | | | | | | | X | |
| Urine albumin/creatinine ratio [h] | | X | | | | X | | X | | X | | X | | X | | X | | X | | X | | X | | X | | X | | X |
| Urine pregnancy test [i] | | X | X | X | X | X | X | X | X | X | X | X | X | X | X | X | X | X | X | X | X | X | X | X | X | X | | X |
| 3-day diet diary [j] | | X | X | X | X | X | X | X | X | X | X | X | X | X | X | X | X | X | X | X | X | X | X | X | X | X | | X |
| PK (plasma pegvaliase) [k] | | X | | | | X | | | | X | | X | | X | | X | | X | | X | | X | | X | | X | | X |
| Plasma Phe, tyrosine [l] | | X | | | | | X | | | X | X | X | X | X | X | X | X | X | X | X | X | X | X | X | X | X | | X |
| Immunogenicity assessments [m] | | X | | | | | | | | X | X | X | X | X | X | X | X | X | X | X | X | X | X | X | X | X | X[m] | X |
| ADHD-RS IV [n] | | X | | | | | | | | X | X | X | X | X | X | X | X | X | X | X | X | X | X | X | X | X | | X |
| BRIEF [o] | | X | | | | | | | | X | X | X | X | X | X | X | X | X | X | X | X | X | X | X | X | X | | X |
| Weekly call (non-visit weeks) [p] | | | | | | | | | | | | | | | | | | | | | | | | | | | | |
| Adverse events [q] | | X | X | X | X | X | X | X | X | X | X | X | X | X | X | X | X | X | X | X | X | X | X | X | X | X | X | X |
| Concomitant medication [q] | | X | X | X | X | X | X | X | X | X | X | X | X | X | X | X | X | X | X | X | X | X | X | X | X | X | X | X |
| Administer study drug [r] | | X | X | X | X | X | X | X | X | X | X | X | X | X | X | X | X | X | X | X | X | X | X | X | X | X | X | X |

Protein Sequence of Anabaena variabilis PAL (SEQ ID NO:1)

```
  1  mktlsgaqsk tssqqtsftg nssanviign qkitindvar varngtlvsl tnntdilggi
 61  qascdyinna vesgepiygv tsgfggmanv aisreqasel qtnlvwflkt gagnkipiad
121  vraamllran shmrgasgir lelikrmeif inagvtpyvv efgsigasgd lvplsyitgs
181  ligldpsfkv dfngkemdap talrqinlsp itlipkegla mmrgtsvmtg iaancvydtq
241  iltaiamgvh aldiqalngt nqsfhpfihn skphpgqiwa adqmisllan sqlvrdeidg
301  khdyrdheli qdryslrcip qylgpivdgi sqiakqieie insvtdnpli dvdnqasyhg
361  gnflgqyvgm gmdhlryig llakhidvqi allaspefsn gippsligr erkvnmglkg
421  lqicgnsimp litfygnsia dfpthaeqf nqminsqgyt satlarrsvd ifqnyvaial
481  mfgvqavdlr tykktghyda raclspater lysavrhvvg qkptsdrpyi wndneqgide
541  hiarisadia aggvivgavq dilpclh
```

FIG. 7A

AvPAL_C503S (SEQ ID NO:2)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVVEFSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLMA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARASLSPATERLYSAVRHVVGQKPTSDRPYIWNDNEQGLDEHIARISADIAAGGVIVQAVQ
DILPCLH

AvPAL_C565S (SEQ ID NO:3)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVVEFSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLMA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARACLSPATERLYSAVRHVVGQKPTSDRPYIWNDNEQGLDEHIARISADIAAGGVIVQAVQ
DILPSLH

AvPAL_C565SC503S (SEQ ID NO:4)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVVEFSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLMA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARASLSPATERLYSAVRHVVGQKPTSDRPYIWNDNEQGLDEHIARISADIAAGGVIVQAVQ
DILPSLH

FIG. 7B

SEQUENCE LISTING

```
<160> NUMBER OF SEQ ID NOS: 4

<210> SEQ ID NO 1
<211> LENGTH: 567
<212> TYPE: PRT
<213> ORGANISM: Artificial Sequence
<220> FEATURE:
<223> OTHER INFORMATION: Anabaena variabilis (Av) PAL wild type

<400> SEQUENCE: 1

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45
```

```
Ser Leu Thr Asn Asn Thr Asp Ile Leu Gln Gly Ile Gln Ala Ser Cys
 50                  55                  60

Asp Tyr Ile Asn Asn Ala Val Glu Ser Gly Glu Pro Ile Tyr Gly Val
 65                  70                  75                  80

Thr Ser Gly Phe Gly Gly Met Ala Asn Val Ala Ile Ser Arg Glu Gln
                 85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
            195                 200                 205

Ser Pro Leu Thr Leu Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
            275                 280                 285

Ala Asn Ser Gln Leu Val Arg Asp Glu Leu Asp Gly Lys His Asp Tyr
290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
450                 455                 460
```

```
Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 2
<211> LENGTH: 567
<212> TYPE: PRT
<213> ORGANISM: Artificial Sequence
<220> FEATURE:
<223> OTHER INFORMATION: Anabaena variabilis (Av) PAL variant
      AvPAL_C503S

<400> SEQUENCE: 2

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255
```

```
Leu Asn Gly Thr Asn Gln Ser Phe His Pro Phe Ile His Asn Ser Lys
            260                 265                 270

Pro His Pro Gly Gln Leu Trp Ala Asp Gln Met Ile Ser Leu Leu
        275                 280                 285

Ala Asn Ser Gln Leu Val Arg Asp Glu Leu Asp Gly Lys His Asp Tyr
        290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
        450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Ser Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
        530                 535                 540

Ile Ser Ala Asp Ile Ala Ala Gly Gly Val Ile Val Gln Ala Val Gln
545                 550                 555                 560

Asp Ile Leu Pro Cys Leu His
                565
```

<210> SEQ ID NO 3
<211> LENGTH: 567
<212> TYPE: PRT
<213> ORGANISM: Artificial Sequence
<220> FEATURE:
<223> OTHER INFORMATION: Anabaena variabilis (Av) PAL variant
      AvPAL_C565S

<400> SEQUENCE: 3

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
```

```
                35                  40                  45
Ser Leu Thr Asn Asn Thr Asp Ile Leu Gln Gly Ile Gln Ala Ser Cys
 50                  55                  60

Asp Tyr Ile Asn Asn Ala Val Glu Ser Gly Glu Pro Ile Tyr Gly Val
 65                  70                  75                  80

Thr Ser Gly Phe Gly Gly Met Ala Asn Val Ala Ile Ser Arg Glu Gln
                 85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
450                 455                 460
```

```
Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                    485                 490                 495

His Tyr Asp Ala Arg Ala Cys Leu Ser Pro Ala Thr Glu Arg Leu Tyr
                500                 505                 510

Ser Ala Val Arg His Val Val Gly Gln Lys Pro Thr Ser Asp Arg Pro
                515                 520                 525

Tyr Ile Trp Asn Asp Asn Glu Gln Gly Leu Asp Glu His Ile Ala Arg
                530                 535                 540

Ile Ser Ala Asp Ile Ala Ala Gly Gly Val Ile Val Gln Ala Val Gln
545                 550                 555                 560

Asp Ile Leu Pro Ser Leu His
                565

<210> SEQ ID NO 4
<211> LENGTH: 567
<212> TYPE: PRT
<213> ORGANISM: Artificial Sequence
<220> FEATURE:
<223> OTHER INFORMATION: Anabaena variabilis (Av) PAL variant AvPAL_
      C565SC503S

<400> SEQUENCE: 4

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
                20                  25                  30

Leu Thr Ile Asn Asp Val Ala Arg Val Ala Arg Asn Gly Thr Leu Val
            35                  40                  45

Ser Leu Thr Asn Asn Thr Asp Ile Leu Gln Gly Ile Gln Ala Ser Cys
50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
        130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
```

-continued

```
                    245                 250                 255
Leu Asn Gly Thr Asn Gln Ser Phe His Pro Phe Ile His Asn Ser Lys
            260                 265                 270
Pro His Pro Gly Gln Leu Trp Ala Ala Asp Gln Met Ile Ser Leu Leu
            275                 280                 285
Ala Asn Ser Gln Leu Val Arg Asp Glu Leu Asp Gly Lys His Asp Tyr
            290                 295                 300
Arg Asp His Glu Leu Ile Gln Asp Arg Tyr Ser Leu Arg Cys Leu Pro
305                 310                 315                 320
Gln Tyr Leu Gly Pro Ile Val Asp Gly Ile Ser Gln Ile Ala Lys Gln
                    325                 330                 335
Ile Glu Ile Glu Ile Asn Ser Val Thr Asp Asn Pro Leu Ile Asp Val
            340                 345                 350
Asp Asn Gln Ala Ser Tyr His Gly Gly Asn Phe Leu Gly Gln Tyr Val
            355                 360                 365
Gly Met Gly Met Asp His Leu Arg Tyr Tyr Ile Gly Leu Leu Ala Lys
370                 375                 380
His Leu Asp Val Gln Ile Ala Leu Leu Ala Ser Pro Glu Phe Ser Asn
385                 390                 395                 400
Gly Leu Pro Pro Ser Leu Leu Gly Asn Arg Glu Arg Lys Val Asn Met
                    405                 410                 415
Gly Leu Lys Gly Leu Gln Ile Cys Gly Asn Ser Ile Met Pro Leu Leu
            420                 425                 430
Thr Phe Tyr Gly Asn Ser Ile Ala Asp Arg Phe Pro Thr His Ala Glu
            435                 440                 445
Gln Phe Asn Gln Asn Ile Asn Ser Gln Gly Tyr Thr Ser Ala Thr Leu
            450                 455                 460
Ala Arg Arg Ser Val Asp Ile Phe Gln Asn Tyr Val Ala Ile Ala Leu
465                 470                 475                 480
Met Phe Gly Val Gln Ala Val Asp Leu Arg Thr Tyr Lys Lys Thr Gly
                    485                 490                 495
His Tyr Asp Ala Arg Ala Ser Leu Ser Pro Ala Thr Glu Arg Leu Tyr
            500                 505                 510
Ser Ala Val Arg His Val Val Gly Gln Lys Pro Thr Ser Asp Arg Pro
            515                 520                 525
Tyr Ile Trp Asn Asp Asn Glu Gln Gly Leu Asp Glu His Ile Ala Arg
            530                 535                 540
Ile Ser Ala Asp Ile Ala Ala Gly Gly Val Ile Val Gln Ala Val Gln
545                 550                 555                 560
Asp Ile Leu Pro Ser Leu His
                    565
```

COMPOSITIONS OF PROKARYOTIC PHENYLALANINE AMMONIA-LYASE AND METHODS OF TREATING ADOLESCENT SUBJECTS

1. CROSS-REFERENCE TO RELATED APPLICATIONS

This application claims the benefit of U.S. Provisional Application No. 63/190,567, filed May 19, 2021, which is incorporated by reference herein in its entirety.

2. SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled 11808-479-999_SEQ_LISTING.txt, was created on May 15, 2022, and is 20,195 bytes in size.

3. FIELD OF THE DISCLOSURE

This disclosure relates to prokaryotic phenylalanine ammonia-lyase (PAL) and compositions thereof, and optimization of such compositions to enhance prokaryotic PAL catalytic activity and/or stability, while reducing immunogenicity and/or proteolytic sensitivity of prokaryotic PAL. The disclosure further relates to the use of such optimal compositions of prokaryotic PAL for treating adolescent subjects.

4. BACKGROUND OF THE DISCLOSURE

PAL is a non-mammalian enzyme widely distributed in plants (Koukol, et al., J. Biol. Chem. 236:2692-2698 (1961); Hanson, et al., The Enzymes 7:75-166 (1972); Poppe, et al., Curr. Org. Chem. 7:1297-1315 (2003)), some fungi (Rao, et al., Can. J. Biochem. 4512:1863-1872 (1967); Abell, et al., Methods Enzymol. 142:242-253 (1987)) and bacteria (Bezanson, et al., Can. J. Microbiol. 16:147-151 (1970); Xiang, et al., J. Biol. Chem. 277:32505-32509 (2002); Hill, et al., Chem. Commun. 1358-1359 (2003)) and can be recombinantly produced in *Escherichia coli*.

PAL from the cyanobacteria strains, *Anabaena variabilis* (Av), has been cloned and expressed in bacteria, and was shown to display PAL enzyme activity in vitro and in vivo (see e.g., U.S. Pat. Nos. 7,531,341; 7,534,595; 7,537,923; and 7,560,263). A pegylated recombinant *Anabaena variabilis* PAL (rAvPAL-PEG) has also been produced, wherein the rAvPAL protein was derivatized by covalent attachment of polyethylene glycol (PEG) to increase its half-life and optimize its pharmacokinetic profile and/or reduce its immunogenicity (Id.). Recently, rAvPAL-PEG was approved as an injectable product for treatment of Phenylketonuria (PKU) in adult subjects. There remains a need for methods for using such therapeutics in adolescent subjects.

5. SUMMARY OF DISCLOSURE

In one aspect, provided herein is a method for reducing blood phenylalanine concentration in a subject, comprising administering to the subject a weekly dose of a formulation comprising an AvPAL variant, wherein the subject is about 12 years old to about 18 years old, and wherein the weekly dose is administered for more than about 50 weeks, wherein the AvPAL variant comprises an amino acid sequence of SEQ ID NO:2, SEQ ID NO:3 or SEQ ID NO:4. In some embodiments, the weekly dose is administered for more than about 60 weeks, more than about 70 weeks, more than about 80 weeks, more than about 90 weeks, more than about 100 weeks, more than about 110 weeks, more than about 120 weeks, more than about 130 weeks, more than about 140 weeks, more than about 150 weeks, more than about 160 weeks, more than about 170 weeks, more than about 180 weeks, more than about 190 weeks, more than about 200 weeks, more than about 210 weeks, more than about 220 weeks, more than about 230 weeks, more than about 240 weeks, or more than about 250 weeks.

In some embodiments, the dosage is in the range of about 0.1 mg per week to about 1 mg per week. In some embodiments, the dosage is in the range of about 1 mg per week to about 2 mg per week. In some embodiments, the dosage is in the range of about 2 mg per week to about 10 mg per week. In some embodiments, the dosage is in the range of about 10 mg per week to about 20 mg per week. In some embodiments, the dosage is in the range of about 20 mg per week to about 40 mg per week. In some embodiments, the dosage is in the range of about 40 mg per week to about 70 mg per week. In some embodiments, the dosage is in the range of about 70 mg per week to about 140 mg per week. In some embodiments, the dosage is in the range of about 140 mg per week to about 280 mg per week. In some embodiments, the dosage is in the range of about 280 mg per week to about 420 mg per week. In some embodiments, the dosage is in the range of about 420 mg per week to about 840 mg per week.

In some embodiments, the AvPAL variant is administered once weekly. In some embodiments, the AvPAL variant is administered twice weekly. In some embodiments, the AvPAL variant is administered four times per week. In some embodiments, the AvPAL variant is administered seven times per week. In some embodiments, the AvPAL variant is administered fourteen times per week. In some embodiments, the AvPAL variant is administered daily.

In some embodiments, the method provided herein comprises administering to the subject the AvPAL variant at an induction dosage in the range of about 0.1 mg per week to about 10 mg per week, followed by administering to the subject the AvPAL variant at a titration dosage in the range of about 1 mg per week to about 200 mg per week, followed by administering to the subject the AvPAL variant at a maintenance dosage in the range of about 20 mg per week to about 840 mg per week. In some embodiments, the induction dosage is about 2.5 mg per week. In some embodiments, the titration dosage is in the range of about 5 mg per week to about 70 mg per week. In some embodiments, the maintenance dosage is in the range of about 140 mg per week to about 420 mg per week. In some embodiments, the induction dosage is administered for a duration of between about 2 week and about 6 weeks, the titration dosage is administered for a duration of between about 3 weeks and about 8 weeks, and the maintenance dosage is administered for a duration of between about 50 weeks and about 80 weeks. In some embodiments, the induction dosage is administered for a duration of about 4 weeks, the titration dosage is administered for a duration of about 5 weeks, and the maintenance dosage is administered for a duration of between about 56 weeks and 64 weeks. In some embodiments, the maintenance dosage is comprised of a first maintenance dosage of between about 70 mg per week and about 280 mg per week, a second maintenance dosage of between about 140 mg per week and about 560 mg per week, and a third maintenance dosage of between about 210 mg per week and about 840 mg per week. In some embodiments, the first maintenance dosage is administered for a duration of between about 16 weeks and about 24 weeks, the second maintenance dosage is administered for a duration of about 16 weeks, and the third maintenance dosage is administered for a duration of about 24 weeks.

In some embodiments, following the administration of the maintenance dosage, the method further comprises administering to a subject the AvPAL variant an extension dosage in the range of about 20 mg per week to about 840 mg per week. In some embodiments, the extension dosage is administered for a duration of between about 40 weeks and about 120 weeks.

In some embodiments, the induction dosage is administered for a duration of about 4 weeks, the titration dosage is administered for a duration of about 5 weeks, the maintenance dosage is administered for a duration of between about 64 weeks, and the extension dosage is administered for a duration of about 80 weeks.

In some embodiments, the method provided herein further comprises assessing the blood phenylalanine concentration prior to administering the induction dosage.

In some embodiments, the method further comprises assessing the blood phenylalanine concentration after administration of one or more induction dosages, titration dosages, maintenance dosages, and/or extension dosages.

In some embodiments, the method further comprises adjusting the dosage based on the blood phenylalanine concentration. In some embodiments, the dosage is adjusted to attain a blood phenylalanine concentration of below about 600 μM. In some embodiments, the dosage is adjusted to attain a blood phenylalanine concentration of below about 360 μM. In some embodiments, the maintenance dosage is increased if blood phenylalanine concentration is greater than about 360 μM.

In some embodiments, the subject has phenylketonuria (PKU). In some embodiments, the subject is between about 12 years old and about 15 years old. In some embodiments, the subject is between about 16 years old and about 17 years old.

In some embodiments, the AvPAL variant comprises the amino acid sequence of SEQ ID NO:2. In some embodiments, the AvPAL variant comprises the amino acid sequence of SEQ ID NO:3. In some embodiments, the AvPAL variant comprises the amino acid sequence of SEQ ID NO:4.

In some embodiments, the AvPAL variant is pegylated. In some embodiments, said pegylation is achieved by reacting the AvPAL variant with NHS-activated polyethylene glycol at a ratio of at least 1.6 polyethylene glycol per lysine residue of AvPAL variant. In some embodiments, said pegylation is achieved by reacting the AvPAL variant with NHS-activated polyethylene glycol at a ratio of at least 2.4 polyethylene glycol per lysine residue of AvPAL variant. In some embodiments, said pegylation is achieved by reacting the AvPAL variant with NHS-activated polyethylene glycol at a ratio of 3 polyethylene glycol per lysine residue of AvPAL variant. In some embodiments, said pegylation is achieved by reacting the AvPAL variant with NHS-activated polyethylene glycol at a ratio of 5 polyethylene glycol per lysine residue of AvPAL variant. In some embodiments, said pegylation is achieved by reacting the AvPAL variant with NHS-activated polyethylene glycol at a ratio of 6 polyethylene glycol per lysine residue of AvPAL variant. In some embodiments, said pegylation is achieved by reacting the AvPAL variant with NHS-activated polyethylene glycol at a ratio of 7 polyethylene glycol per lysine residue of AvPAL variant. In some embodiments, said pegylation is achieved by reacting the AvPAL variant with NHS-activated polyethylene glycol at a ratio of 8 polyethylene glycol per lysine residue of AvPAL variant. In some embodiments, said pegylation is achieved by reacting the AvPAL variant with NHS-activated polyethylene glycol at a ratio of 9 polyethylene glycol per lysine residue of AvPAL variant.

In some embodiments, the AvPAL variant is administered as a formulation comprising a pharmaceutically acceptable carrier comprising a stabilizer. In some embodiments, the stabilizer is L-phenylalanine or structural analog thereof. In some embodiments, the stabilizer is selected from the group consisting of L-phenylalanine, trans-cinnamic acid and benzoic acid. In some embodiments, the stabilizer is trans-cinnamic acid. In some embodiments, the formulation further comprises sodium chloride, and tromethamine and tromethamine hydrochloride.

Other features and advantages of the disclosure will become apparent from the following detailed description. It should be understood, however, that the detailed description and the specific examples, while indicating preferred embodiments of the disclosure, are given by way of illustration only, because various changes and modifications within the spirit and scope of the disclosure will become apparent to those skilled in the art from this detailed description.

6. BRIEF DESCRIPTION OF THE FIGURES

Figure 1B:
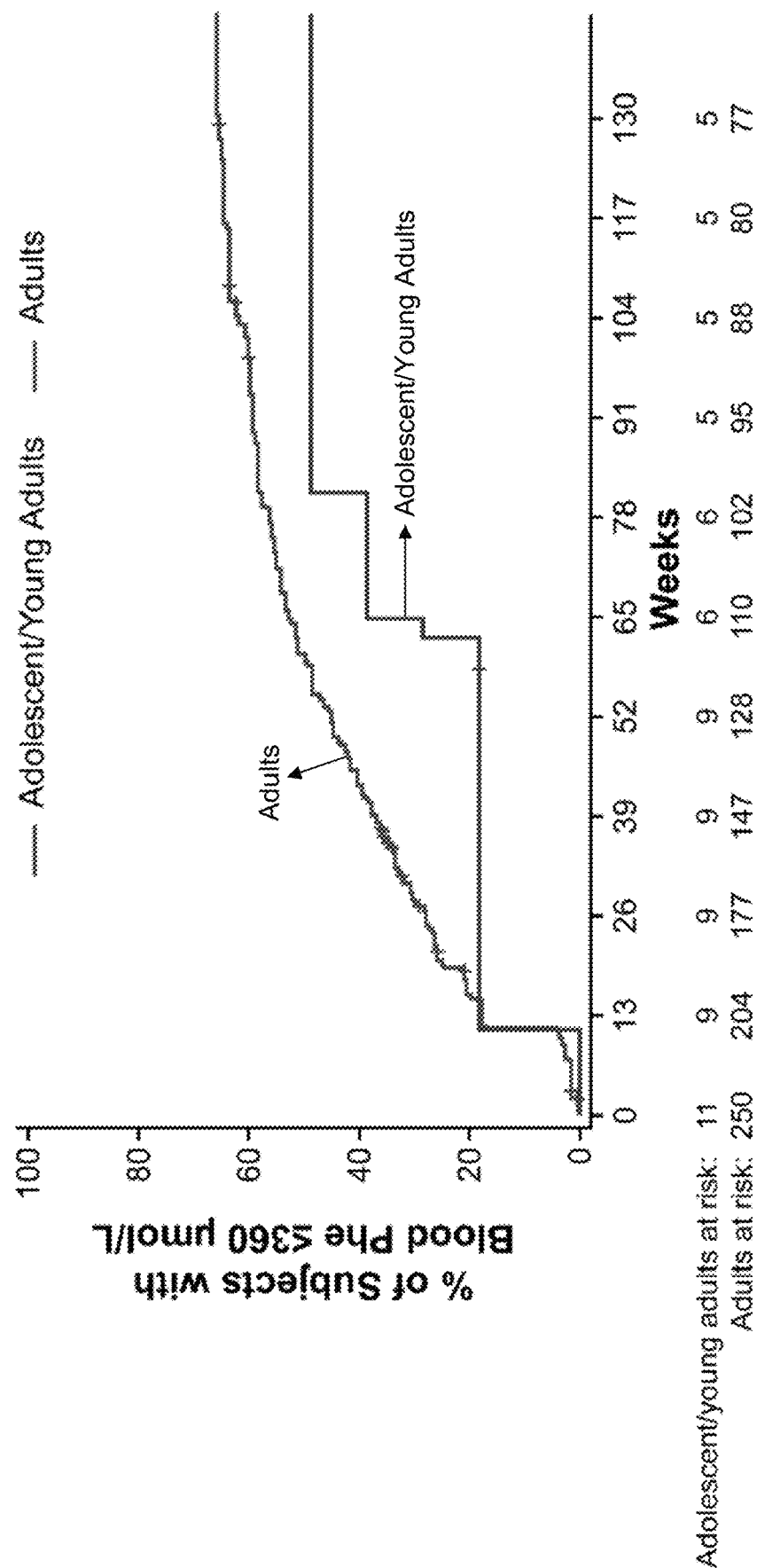
Figure 1C:
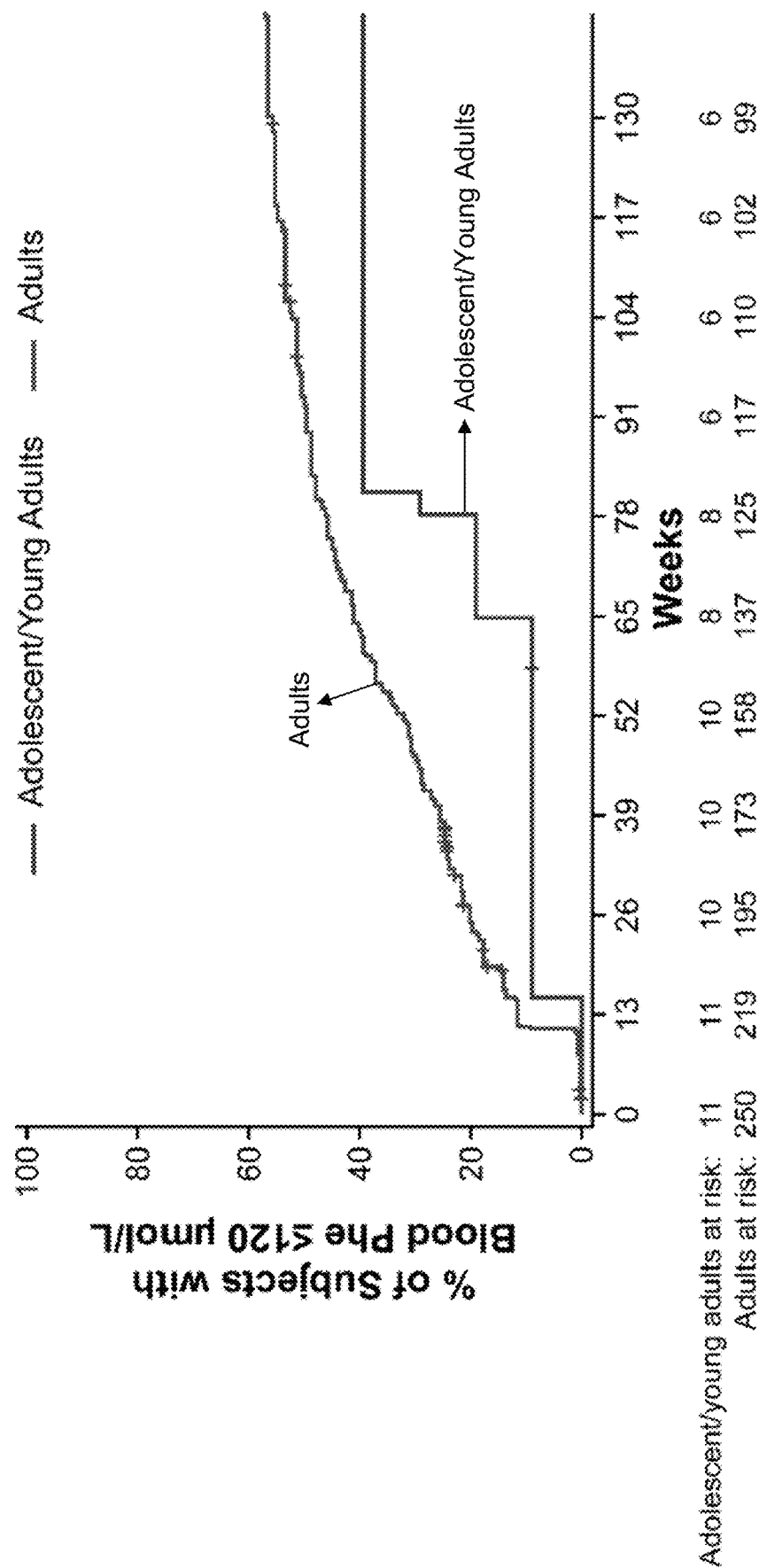

FIG. 1A shows percentage of subjects who met blood Phe threshold≤600 μmol/L. FIG. 1B shows percentage of subjects who met blood Phe threshold≤360 μmol/L. FIG. 1C shows percentage of subjects who met blood Phe threshold≤120 μmol/L.

Figure 2A:
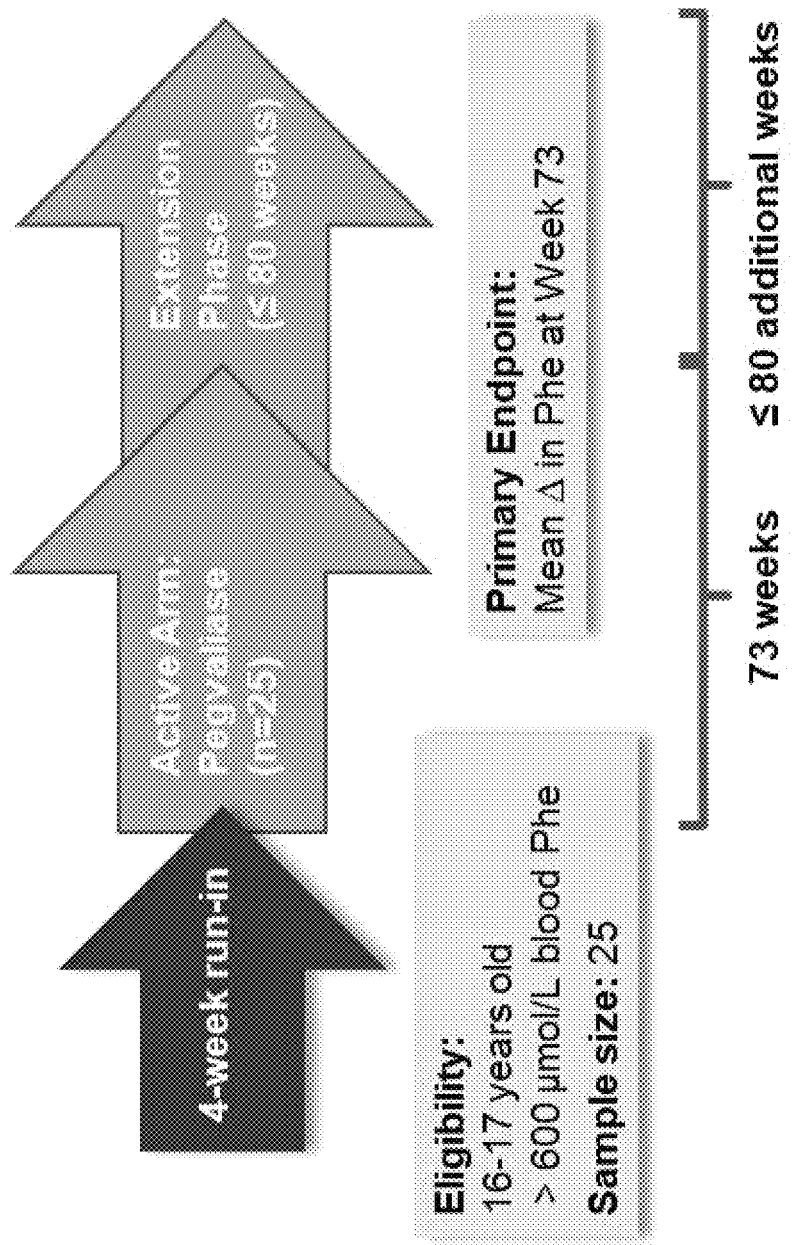
Figure 2B:
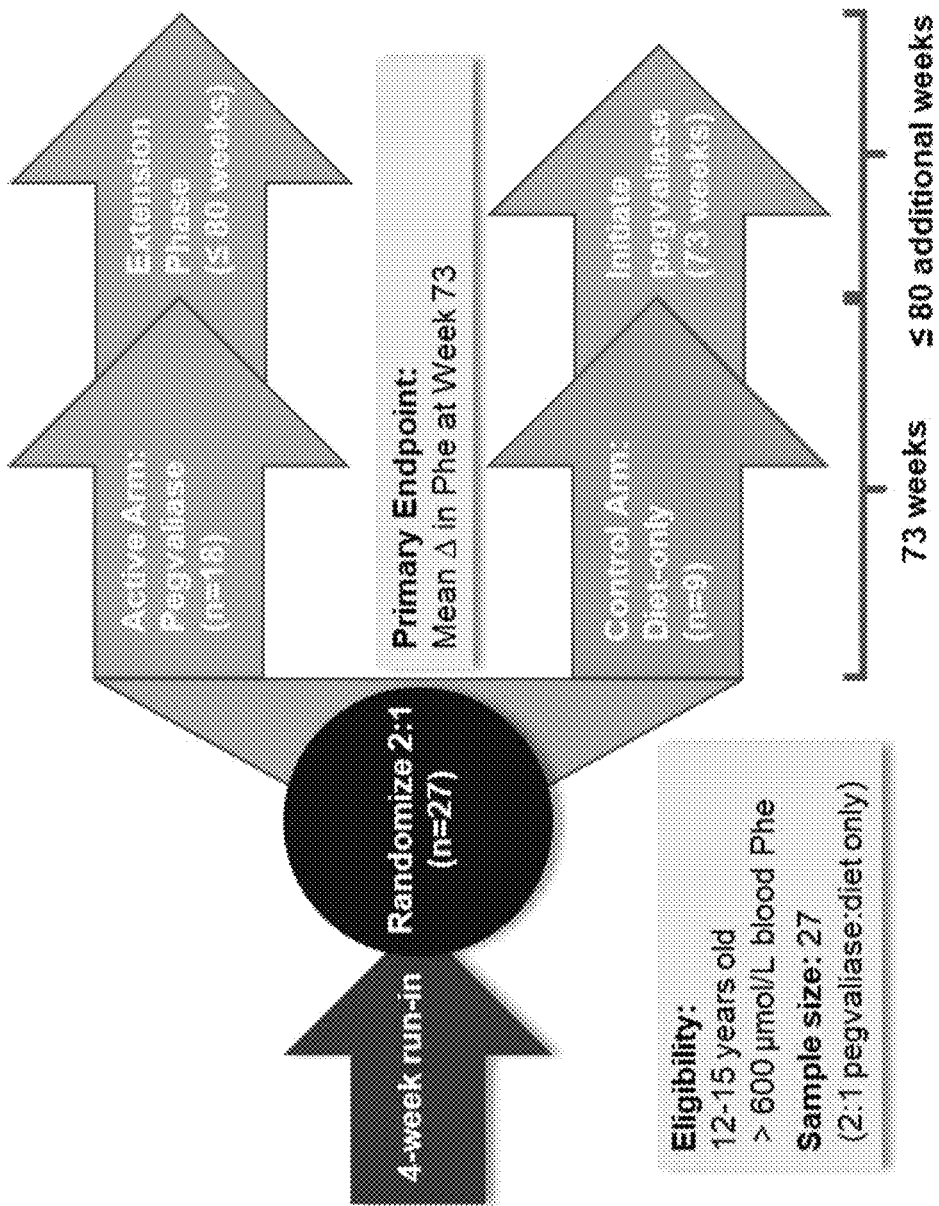
Figure 2C:
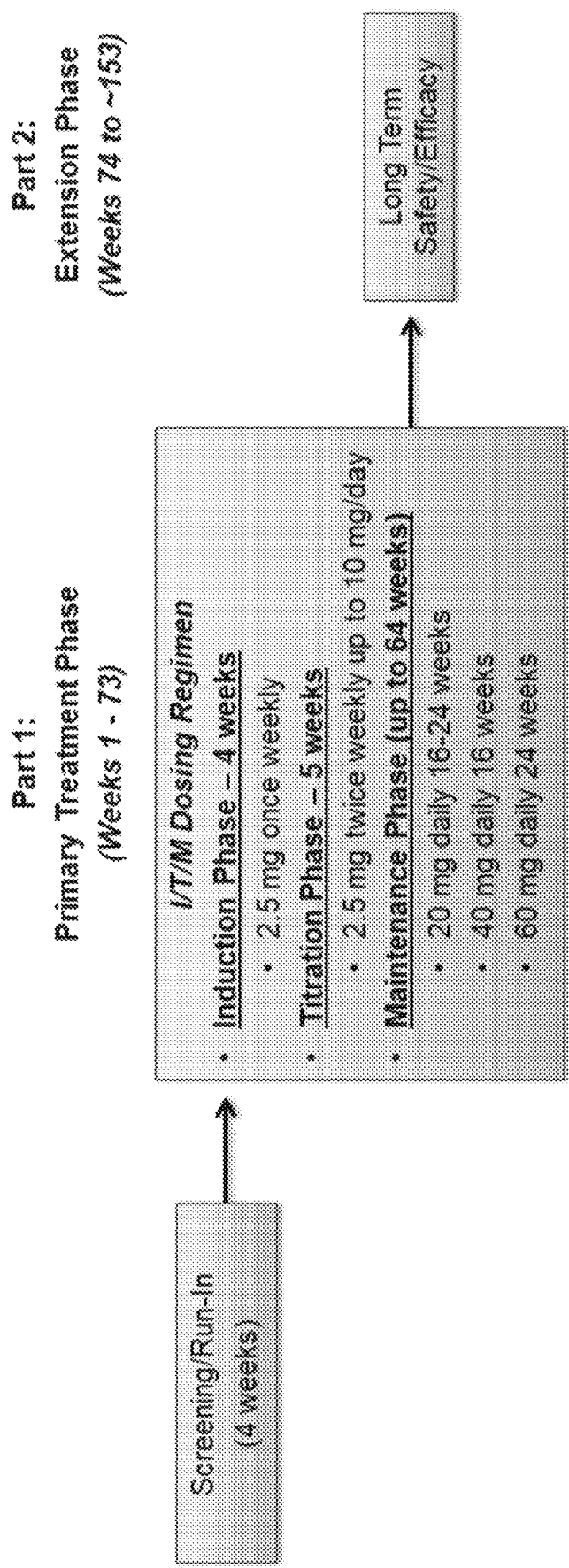

FIG. 2A illustrates study schema for Cohort A (16-17 Year-Olds): Single-Arm Open-Label Study. FIG. 2B illustrates study schema for Cohort B (12-15 Year-Olds): Pegvaliase active treatment arm vs diet-only control arm (randomized treatment assignment at enrollment). FIG. 2C shows dosing schematic for Cohort A and active arm of Cohort B. The 9 Cohort B diet only control subjects follows the Part 1 assessment schedule (except for pegvaliase dosing) from Weeks 1 through 73 and then repeats the Part 1 assessment schedule including pegvaliase dosing from Weeks 74 through 146.

FIG. 3 shows schedule of assessments for Part 1 (Cohort A and Cohort B active arm). ACTH, adrenocorticotropic hormone; ADHD-RS IV, attention deficit hyperactivity disorder rating scale IV; BRIEF, Behavior Rating Inventory of Executive Function, ECG, electrocardiogram; eCRF, electronic Case Report Form; HRV, hypersensitivity reaction visit; PK, pharmacokinetics; PKU, phenylketonuria; SC/ET, study completion/early termination visit. a) All scheduled visits are in the study clinic or by a home healthcare nurse; non-clinic visits are via telephone. Assessments are performed pre-dose unless otherwise specified. b) After written informed consent, screening assessments must be performed within 28 days prior to Part 1, Day 1. Subjects are assessed for blood Phe concentration during Screening/Run-in with 2 measurements 2 to 4 weeks apart. c) Self administration of the first study drug dose occurs in study clinic; once competence is documented, subjects self administer study drug daily. d) Must be completed prior to administration of the first dose of study drug. Additional observers identified after screening must be trained. e) PKU history includes highest blood Phe (and age), subject appraisal of metabolic control, and age when low-Phe diet was discontinued. f) HIV, hepatitis B and C screens are performed. g) It is recommended that urine samples are obtained as a first or second morning void. In the event of elevated urinary protein on a test result, a repeat urinalysis should be performed. This repeat urine sample must be performed in the morning at the first or second morning void to allow for accurate test results and may be performed by a home healthcare nurse. h) To be done by a local laboratory. i) Serum cortisol samples should be taken before study drug administration in the morning before 10:00 am. A home healthcare nurse may collect samples for subject convenience. If two results are low and abnormal, the subject is asked to perform additional sampling for plasma ACTH and a low-dose conventional ACTH stimulation test or the ACTH test method based on the clinical practice at the site. j) It is recommended that urine samples are obtained as a first or second morning void. Subjects with a confirmed urine/albumin creatinine ratio of ≥100 mg/g should be referred to a nephrologist for consultation if results were within normal range at baseline. Subjects who had elevated results at baseline followed by a confirmed subsequent increase of 100-200 mg/g from baseline should also be referred to a nephrologist for consultation. k) To be done locally (if applicable). If urine pregnancy test is positive or equivocal, serum pregnancy test (central laboratory) must be done. l) Subjects should record at home all food, beverages, special low-protein foods, and medical foods consumed during the three consecutive days preceding a study visit. No change in protein (dietary and medical food) intake is allowed in Part 1. At Screening, diet diary is dispensed for use in reporting at Part 1, Week 1. m) Blood is collected before study drug administration (pre-dose). Intensive PK sampling is performed at Week 73 in all subjects. Samples are taken at pre-dose, 2, 4, 8, 12, and 24 hours post dose. The 24-hour sample is taken prior to the next daily dose. n) Blood is collected for plasma Phe analysis after fasting 2.5 to 5 hours. o) Immunogenicity assays include total anti-pegvaliase antibodies (TAb), anti-PAL IgG, anti-PAL IgM, anti-PEG IgM, anti-PEG IgG, and neutralizing antibodies (NAb). At hypersensitivity reaction visit (HRV), only anti-pegvaliase IgE are assessed. p) Investigator-rated. q) Completed by caregiver/parent. r) Between scheduled clinic visits, the clinic staff contact the subject weekly to monitor if the subject is experiencing problems with self-administration, to ask about any AEs or concomitant medications, and to answer questions. s) AEs and concomitant medications should be noted whenever a subject is assessed by study personnel. Following signed informed consent and prior to the first dose of pegvaliase, only SAEs associated with study procedures are collected. After the first dose, all AEs and SAEs are collected until 4 weeks after the last study drug dose or the Study Completion Visit/Early Termination Visit, whichever occurs last. If there is a skin reaction that lasts ≥14 days, the Skin Reaction eCRF should be completed. Subjects who experience an injection-site skin reaction that lasts ≥14 days should be referred to a dermatologist for consultation and a skin biopsy (optional). It is recommended that a photograph of the skin reaction be taken by the subject or the site to help assess the event; photographs may be collected by the sponsor. t) Subjects may be premedicated with an H1 antagonist, and an H2 antagonist, and an antipyretic (e.g., acetaminophen) approximately 2-3 hours prior to study drug per investigator determination. If non-steroidal anti-inflammatory medication (NSAIDs) is administered as a premedication, it should be given with food. For non-clinic visits, subjects are asked about study drug self administration.

FIG. 4 illustrates schedule of Assessments for Part 2 (Cohort A and Cohort B Active Arm). ACTH, adrenocorticotropic hormone; ADHD-RS IV, attention deficit hyperactivity disorder rating scale IV; BRIEF, Behavior Rating Inventory of Executive Function, ECG, electrocardiogram; eCRF, electronic Case Report Form; HRV, hypersensitivity reaction visit; PK, pharmacokinetics; PKU, phenylketonuria; SC/ET, study completion/early termination visit. a) All scheduled visits are in the study clinic or by a home healthcare nurse; non-clinic visits are via telephone. Assessments are performed pre dose unless otherwise specified. b) The Week 73 visit marks both the end of the Primary Treatment Phase (Part 1) and the beginning of the Extension Phase (Part 2). The pre-dose assessments constituting the end of the Primary Treatment Phase and the administration of study drug constituting the beginning of the Extension Phase are shown in the Week 73 columns of both FIG. 3 and FIG. 4. c) Additional observers identified after screening must be trained. d) It is recommended that urine samples are obtained as a first or second morning void. In the event of elevated urinary protein on a test result, a repeat urinalysis should be performed. This repeat urine sample must be performed in the morning at the first or second morning void to allow for accurate test results and may be performed by a home healthcare nurse. e) To be done by a local laboratory. f) Serum cortisol samples should be taken before study drug administration in the morning before 10:00 am. A home healthcare nurse may collect samples for subject convenience. If two results are low and abnormal, the subject is asked to perform additional sampling for plasma ACTH and a low dose conventional ACTH stimulation test or the ACTH test method based on the clinical practice at the site. g) It is recommended that urine samples are obtained as a first or second morning void. Subjects with a confirmed urine/albumin creatinine ratio of ≥100 mg/g should be referred to a nephrologist for consultation if results were within normal range at baseline. Subjects who have elevated results at baseline followed by a confirmed subsequent increase of 100 200 mg/g from baseline should also be referred to a nephrologist for consultation. h) To be done locally (if applicable). If urine pregnancy test is positive or equivocal, serum pregnancy test (central laboratory) must be done. i) Subjects should record at home all food, beverages, special low-protein foods, and medical foods consumed during the three consecutive days preceding a study visit. No change in protein (dietary and medical food) intake is allowed in Part 1. At Screening, diet diary is dispensed for use in reporting at Part 1, Week 1. j) Blood is collected before study drug administration (pre dose). Intensive PK sampling is performed at Week 73 in all subjects. Samples are taken at pre-dose, 2, 4, 8, 12, and 24 hours post dose. The 24 hour sample is taken prior to the next daily dose. k) Blood is collected for plasma Phe analysis after fasting 2.5 to 5 hours. l) Immunogenicity assays include total anti-pegvaliase antibodies (TAb), anti-PAL IgG, anti-PAL IgM, anti-PEG IgM, anti-PEG IgG, and neutralizing antibodies (NAb). At hypersensitivity reaction visit (HRV), only anti-pegvaliase IgE is assessed. m) Investigator-rated. n) Completed by caregiver/parent. o) Between scheduled clinic visits, the clinic staff contact the subject weekly to monitor if the subject is experiencing problems with self administration, to ask about any AEs or concomitant medications, and to answer questions. p) AEs and concomitant medications should be noted whenever a subject is assessed by study personnel. All AEs and SAEs are collected until 4 weeks after the last study drug dose or the Study Completion Visit/Early Termination Visit, whichever occurs last. If there is a skin reaction that lasts ≥14 days, the Skin Reaction eCRF should be completed. Subjects who experience an injection-site skin reaction that lasts ≥14 days should be referred to a dermatologist for consultation and a skin biopsy (optional). It is recommended that a photograph of the skin reaction be taken by the subject or the site to help assess the event; photographs may be collected by the sponsor. q) Subjects may be premedicated with an H1 antagonist, and an H2 antagonist, and an antipyretic (e.g., acetaminophen) approximately 2-3 hours prior to study drug per investigator determination. If non-steroidal anti-inflammatory medication (NSAIDs) is administered as a premedication, it should be given with food. For non-clinic visits, subjects are asked about study drug self administration.

FIG. 5 illustrates schedule of assessments for Part 1 (Cohort B diet-only control arm). ACTH, adrenocorticotropic hormone; ADHD-RS IV, attention deficit hyperactivity disorder rating scale IV; BRIEF, Behavior Rating Inventory of Executive Function, ECG, electrocardiogram; eCRF, electronic Case Report Form; HRV, hypersensitivity reaction visit; PK, pharmacokinetics; PKU, phenylketonuria; SC/ET, study completion/early termination visit. a) All scheduled visits are in the study clinic or by a home healthcare nurse; non-clinic visits are via telephone. b) After written informed consent, screening assessments must be performed within 28 days prior to Part 1, Day 1. Subjects are assessed for blood Phe concentration during Screening/Run-in with 2 measurements 2 to 4 weeks apart. c) Self administration of the first study drug dose occurs in Part 2 in the clinic; once competence is documented, subjects self administer study drug daily during Part 2. d) Must be completed prior to administration of the first dose of study drug in Part 2. Additional observers identified after Screening must be trained. e) PKU history includes highest blood Phe (and age), subject appraisal of metabolic control, and age when low-Phe diet was discontinued. f) HIV, hepatitis B and C screens are performed. g) It is recommended that urine samples are obtained as a first or second morning void. In the event of elevated urinary protein on a test result, a repeat urinalysis should be performed. This repeat urine sample must be performed in the morning at the first or second morning void to allow for accurate test results and may be performed by a home healthcare nurse. h) To be done by a local laboratory. i) Serum cortisol samples should be taken before study drug administration in the morning before 10:00 am. A home healthcare nurse may collect samples for subject convenience. If two results are low and abnormal, the subject is asked to perform additional sampling for plasma ACTH and a low dose conventional ACTH stimulation test or the ACTH test method based on the clinical practice at the site. j) It is recommended that urine samples are obtained as a first or second morning void. Subjects with a confirmed urine/albumin creatinine ratio of ≥100 mg/g should be referred to a nephrologist for consultation if results were within normal range at baseline. Subjects who had elevated results at baseline followed by a confirmed subsequent increase of 100 200 mg/g from baseline should also be referred to a nephrologist for consultation. k) To be done locally (if applicable). If urine pregnancy test is positive or equivocal, serum pregnancy test (central laboratory) must be done. l) Subjects should record at home all food, beverages, special low-protein foods, and medical foods consumed during the three consecutive days preceding a study visit. No change in protein (dietary and medical food) intake is allowed in Part 1. At Screening, diet diary is dispensed for use in reporting at Part 1, Week 1. m) Blood is collected for plasma Phe analysis after fasting 2.5 to 5 hours. n) Investigator-rated. o) Completed by caregiver/parent. p) Between scheduled clinic visits, the clinic staff contact the subject weekly to ask about any AEs or concomitant medications, and to answer questions. q) AEs and concomitant medications should be noted whenever a subject is assessed by study personnel. Following signed informed consent and prior to Day 1, only SAEs associated with study procedures are collected. Beginning with the Day 1 visit, all AEs and SAEs are collected until 4 weeks after the last study drug dose or the Study Completion Visit/Early Termination Visit, whichever occurs last. If there is a skin reaction that lasts ≥14 days, the Skin Reaction eCRF should be completed. Subjects who experience an injection-site skin reaction that lasts ≥14 days should be referred to a dermatologist for consultation and a skin biopsy (optional). It is recommended that a photograph of the skin reaction be taken by the subject or the site to help assess the event; photographs may be collected by the sponsor.

FIG. 6 illustrates schedule of assessments for Part 2 (pegvaliase treatment for Cohort B diet-only control arm). ACTH, adrenocorticotropic hormone; ADHD-RS IV, attention deficit hyperactivity disorder rating scale IV; BRIEF, Behavior Rating Inventory of Executive Function, ECG, electrocardiogram; eCRF, electronic Case Report Form; HRV, hypersensitivity reaction visit; PK, pharmacokinetics; PKU, phenylketonuria; SC/ET, study completion/early termination visit. All scheduled visits are in the study clinic or by a home healthcare nurse; non-clinic visits are via telephone. a) Assessments are performed pre dose unless otherwise specified. b) For Cohort B control subjects, the Week 73 visit marks both the end of Part 1, when their PKU is treated with diet alone, and the beginning of Part 2, when they receive pegvaliase. The Week 73 pre-dose assessments constituting the end of Part 1 are shown in the Week 73 column of FIG. 5. These same assessments, used as Baseline assessments for Part 2, are shown in the Week 73 column of FIG. 6, along with the administration of study drug that marks the beginning of Part 2. c) Self administration of the first study drug dose occurs in study clinic; once competence is documented, subjects self administer study drug daily. d) Must be completed prior to administration of the first dose of study drug. Additional observers identified after screening must be trained. e) It is recommended that urine samples are obtained as a first or second morning void. In the event of elevated urinary protein on a test result, a repeat urinalysis should be performed. This repeat urine sample must be performed in the morning at the first or second morning void to allow for accurate test results and may be performed by a home healthcare nurse. f) To be done by a local laboratory. g) Serum cortisol samples should be taken before study drug administration in the morning before 10:00 am. A home healthcare nurse may collect samples for subject convenience. If two results are low and abnormal, the subject is asked to perform additional sampling for plasma ACTH and a low dose conventional ACTH stimulation test or the ACTH test method based on the clinical practice at the site. h) It is recommended that urine samples are obtained as a first or second morning void. Subjects with a confirmed urine/albumin creatinine ratio of ≥100 mg/g should be referred to a nephrologist for consultation if results were within normal range at baseline. Subjects who had elevated results at baseline followed by a confirmed subsequent increase of 100 200 mg/g from baseline should also be referred to a nephrologist for consultation. i) To be done locally (if applicable). If urine pregnancy test is positive or equivocal, serum pregnancy test (central laboratory) must be done. j) Subjects should record at home all food, beverages, special low-protein foods, and medical foods consumed during the three consecutive days preceding a study visit. No change in protein (dietary and medical food) intake is allowed in Part 1. At Screening, diet diary is dispensed for use in reporting at Part 1, Week 1. k) Blood is collected before study drug administration (pre dose). Intensive PK sampling is performed at Week 73 in all subjects. Samples are taken at pre-dose, 2, 4, 8, 12, and 24 hours post dose. The 24 hour sample is taken prior to the next daily dose. l) Blood is collected for plasma Phe analysis after fasting 2.5 to 5 hours. m) Immunogenicity assays include total anti-pegvaliase antibodies (TAb), anti-PAL IgG, anti-PAL IgM, anti-PEG IgM, anti-PEG IgG, and neutralizing antibodies (NAb). At hypersensitivity reaction visit (HRV), only anti-pegvaliase IgE is assessed. n) Investigator-rated. o) Completed by caregiver/parent. p) Between scheduled clinic visits, the clinic staff contact the subject weekly to monitor if the subject is experiencing problems with self administration, to ask about any AEs or concomitant medications, and to answer questions. q) AEs and concomitant medications should be noted whenever a subject is assessed by study personnel. All AEs and SAEs are collected until 4 weeks after the last study drug dose or the Study Completion Visit/Early Termination Visit, whichever occurs last. If there is a skin reaction that lasts ≥14 days, the Skin Reaction eCRF should be completed. Subjects who experience an injection-site skin reaction that lasts ≥14 days should be referred to a dermatologist for consultation and a skin biopsy (optional). It is recommended that a photograph of the skin reaction be taken by the subject or the site to help assess the event; photographs may be collected by the sponsor. r) Subjects may be premedicated with an H1 antagonist, and an H2 antagonist, and an antipyretic (e.g., acetaminophen) approximately 2-3 hours prior to study drug per investigator determination. If non-steroidal anti-inflammatory medication (NSAIDs) is administered as a premedication, it should be given with food. For non-clinic visits, subjects are asked about study drug self administration.

FIG. 7A shows the sequence of wild type AvPAL (SEQ ID NO:1). FIG. 7B shows sequences of three AvPAL variants (SEQ ID NOs:2-4).

7. DETAILED DESCRIPTION OF THE DISCLOSURE

The present disclosure is based in part on the superior effects for treating adolescent subjects (e.g., subjects of 12 to 17 years old) having PKU with rAvPAL according to the dosing regimen provided herein. Thus, in one aspect, provided herein is a method for treating an adolescent subject having PKU comprising administering an rAvPAL provided herein according to the dosing regimen described herein, e.g., as in the Example section below.

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms can be found in reference works, including Carey and Sundberg, Advanced Organic Chemistry, 3rd Edition, Vols. A and B (Plenum Press, New York 1992). The practice of the present disclosure will employ, unless otherwise indicated, conventional methods of synthetic organic chemistry, mass spectroscopy, preparative and analytical methods of chromatography, protein chemistry, biochemistry, recombinant DNA techniques and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., 4th Edition, 2004); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990).

All publications, patents and patent applications cited herein, whether supra or infra, are hereby incorporated by reference in their entirety.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide-binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA can include introns.

"Recombinant polynucleotide" refers to a polynucleotide having sequences that are not naturally joined together. An amplified or assembled recombinant polynucleotide can be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide can serve a non-coding function (e.g., promoter, origin of replication, ribosome-binding site, etc.) as well.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but can be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to the substitution in a polypeptide of an amino acid with a functionally similar amino acid. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Amino acids can also be grouped as follows:
(1) hydrophobic: Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using a sequence comparison algorithm described in U.S. Pat. No. 7,553,653, which is herein incorporated by reference in its entirety, or by visual inspection.

The phrase "substantially homologous" or "substantially identical" in the context of two nucleic acids or polypeptides, generally refers to two or more sequences or subsequences that have at least 40%, 60%, 80%, 90%, 95%, 98% nucleotide or amino acid residue identity, when compared and aligned for maximum correspondence, as measured using one of the following sequence comparison algorithms or by visual inspection. The substantial identity can exist over a region of the sequences that is at least about 50 residues in length, such as over a region of at least about 100 residues, or over a region of at least about 150 residues. In certain embodiments, the sequences are substantially identical over the entire length of either or both comparison biopolymers.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the prokaryotic PAL variant compositions are substantially pure or isolated. In some embodiments, the prokaryotic PAL variant compositions are substantially pure or isolated with respect to the macromolecular starting materials used in their synthesis. In some embodiments, the pharmaceutical compositions comprise a substantially purified or isolated prokaryotic PAL variant admixed with one or more pharmaceutically acceptable excipient.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally occurring.

"Wild-type" (wt) is a term referring to the natural genetic form of an organism. A wild-type is distinguished from a mutant form (an organism with a genetic mutation).

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation and the like. Furthermore, "polypeptide" as used herein refers to a protein, which includes modifications, such as deletions, additions and substitutions (generally conservative in nature), to the native sequence, as long as the protein maintains the desired activity. Such polypeptides may be referred to as "mutants" herein. These modifications can be deliberate, as through site-directed mutagenesis, or can be accidental, such as through mutations arising with hosts that produce the proteins or errors due to PCR amplification.

As used herein, "variant," "analog," or "derivative" is a compound, e.g., a peptide, having more than about 70% sequence but less than 100% sequence similarity with a given compound, e.g., a peptide. Such variants, analogs or derivatives can be comprised of non-naturally occurring amino acid residues, including by way of example and not limitation, homoarginine, ornithine, penicillamine, and norvaline, as well as naturally occurring amino acid residues. Such variants, analogs or derivatives can also be composed of one or a plurality of D-amino acid residues, and can contain non-peptide interlinkages between two or more amino acid residues.

As used herein, the "ratio" of a PAL polypeptide (e.g., AvPAL or variant thereof) and a water-soluble polymer (e.g., polyethylene glycol or PEG) refers to the reaction condition molar ratio between the PAL polypeptide and the water-soluble polymer. For example, a ratio of about 1:3 for AvPAL and polyethylene glycol (1:3 AvPAL:PEG) means that the chemically modified PAL was produced in a reaction condition with about 1 mol lysine residue on the AvPAL per 3 mol of polyethylene glycol. Because an AvPAL monomer has 18 lysine residues, a ratio of about 1:3 AvPAL:PEG corresponds to 1 mol AvPAL per 54 mol PEG in the pegylation reaction.

"Treatment" or "treating" as used herein refers to prophylactic treatment or therapeutic treatment or diagnostic treatment. A "prophylactic" treatment is a treatment administered to a subject who does not exhibit signs of disease or pathology, i.e., a PKU, or exhibits only early signs for the purpose of decreasing the risk of developing pathology. The prokaryotic PAL compositions, including formulations, provided herein can be given as a prophylactic treatment to reduce the likelihood of developing a pathology, i.e., a PKU, or to minimize the severity of the pathology, if developed. A "therapeutic" treatment is a treatment administered to a subject who exhibits signs or symptoms of pathology, i.e., a PKU, for the purpose of diminishing or eliminating those signs or symptoms. The signs or symptoms can be biochemical, cellular, histological, functional, subjective or objective. The prokaryotic PAL compositions can be given as a therapeutic treatment or for diagnosis. "Diagnostic" means identifying the presence or nature of a pathologic condition, i.e., a PKU. Diagnostic methods differ in their specificity and selectivity. While a particular diagnostic method may not provide a definitive diagnosis of a condition, it suffices if the method provides a positive indication that aids in diagnosis.

As used herein, the terms "prevent," "preventing," and "prevention" refer to the total or partial inhibition of the development, recurrence, onset or spread of a disease and/or symptom related thereto (e.g., a disease or symptom related thereto that is associated with elevated phenylalanine levels, such as PKU in a patient), resulting from the administration of a therapy or combination of therapies provided herein, e.g., AvPAL, AvPAL variant, or any derivative thereof.

"Pharmaceutical composition" refers to a composition suitable for pharmaceutical use in subject animal, including humans and mammals. A pharmaceutical composition comprises a pharmacologically effective amount of a prokaryotic PAL polypeptide and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions encompass any composition made by admixing a prokaryotic PAL polypeptide provided herein and a pharmaceutically acceptable carrier.

"Pharmaceutically acceptable carrier" refers to any of the standard pharmaceutical excipients, vehicles, diluents, stabilizers, preservatives, solubilizers, emulsifiers, adjuvants and/or carriers, such as, for example and not for limitation, a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Pharmaceutical carriers to be used can depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

By "pharmaceutically acceptable" or "pharmacologically acceptable" is meant a material which is not biologically or otherwise undesirable, i.e., the material can be administered to an individual without causing any undesirable biological effects or interacting in a deleterious manner with any of the components of the composition in which it is contained.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. The term does not denote a particular age or gender. As used herein, the terms "subject" and "patient" are used interchangeably. As used herein, a subject is preferably a mammal such as a non-primate (e.g., cows, pigs, horses, cats, dogs, rats, etc.) or a primate (e.g., monkey and human), most preferably a human. In some embodiments, the subject is a mammal, preferably a human, having been administered a PAL enzyme, such as AvPAL, or variants thereof (e.g., SEQ ID NO:2, SEQ ID NO:3 and/or SEQ ID NO:4 (FIG. 7B)) and/or any derivatives thereof (e.g., pegylated PAL) and/or any pharmaceutical compositions and/or any pharmaceutical compositions produced by any of the methods disclosed herein. In some embodiments of the methods and kits provided herein, the patient has a disease or symptom related thereto that is associated with elevated phenylalanine levels, such as HPA or PKU (e.g., classic PKU, severe PKU, moderate PKU or any subpopulation thereof). In some embodiments, the patient is a patient receiving EST (e.g., rAvPAL or rAvPAL-PEG) for elevated phenylalanine levels (e.g., a patient with PKU). In another embodiment of the methods provided herein, the patient is administered a low or modified protein diet, or a low or modified phenylalanine diet in combination with a pharmaceutical composition disclosed herein, such that plasma phenylalanine are decreased, e.g., by at least about 25%. See, e.g., U.S. Pat. Nos. 7,531,341 and 7,534,595 for further information on the management of patient populations with elevated phenylalanine levels (e.g., HPA and PKU) with a PAL or PAL-PEG (e.g., AvPAL or rAvPAL-PEG, or any variant thereof), which, in certain embodiments, can be used in conjunction with the methods and kits provided herein.

As used herein, the term "therapy" refers to any protocol, method and/or agent that can be used in the prevention, management, treatment and/or amelioration of disease (or symptom related thereto) associated with elevated phenylalanine levels (e.g., PKU). In certain embodiments, the terms "therapies" and "therapy" refer to a biological therapy, supportive therapy, and/or other therapies useful in the prevention, management, treatment and/or amelioration of a disease associated with elevated phenylalanine levels (e.g., PKU) known to one of skill in the art such as medical personnel.

The term "tissue" as used herein refers to tissues that are obtained from a mammal, e.g., human. For example, a tissue may be from a biopsy sample, surgically removed tissue, or postmortem collection. Furthermore, the tissue may be homogenized and extracted to isolate the enzyme or antibodies from the tissue.

Method for Treating Adolescent Subjects

In one aspect, provided herein is a method for reducing blood phenylalanine concentration in an adolescent subject, comprising administering to the adolescent subject a weekly dose of a formulation comprising a pegylated AvPAL variant. In some embodiments, the subject is between the ages of about 12 years old to about 18 years old. In some embodiments, the subject is between the ages of about 12 years old to about 17 years old. In some embodiments, the subject is between the ages of about 12 years old to about 16 years old. In some embodiments, the subject is between the ages of about 12 years old to about 15 years old. In some embodiments, the subject is between the ages of about 15 years old to about 18 years old. In some embodiments, the subject is between the ages of about 16 years old to about 18 years old. In some embodiments, the subject is between the ages of about 17 years old to about 18 years old. In some embodiments, the subject is between the ages of about 15 years old to about 17 years old. In some embodiments, the subject is between the ages of about 16 years old to about 17 years old. In some embodiments, the subject is about 12 years old. In some embodiments, the subject is about 13 years old. In some embodiments, the subject is about 14 years old. In some embodiments, the subject is about 15 years old. In some embodiments, the subject is about 16 years old. In some embodiments, the subject is about 17 years old. In some embodiments, the subject is about 18 years old.

In some embodiments, provided herein is a method for reducing blood phenylalanine concentration in a subject, comprising administering to the subject a weekly dose of a formulation comprising an AvPAL variant, wherein the subject is about 12 years old to about 18 years old, and wherein the weekly dose is administered for more than about 50 weeks. In some embodiments, the weekly dose is administered for more than about 60 weeks. In some embodiments, the weekly dose is administered for more than about 70 weeks. In some embodiments, the weekly dose is administered for more than about 80 weeks. In some embodiments, the weekly dose is administered for more than about 90 weeks. In some embodiments, the weekly dose is administered for more than about 100 weeks. In some embodiments, the weekly dose is administered for more than about 110 weeks. In some embodiments, the weekly dose is administered for more than about 120 weeks. In some embodiments, the weekly dose is administered for more than about 130 weeks. In some embodiments, the weekly dose is administered for more than about 140 weeks. In some embodiments, the weekly dose is administered for more than about 150 weeks. In some embodiments, the weekly dose is administered for more than about 160 weeks. In some embodiments, the weekly dose is administered for more than about 170 weeks. In some embodiments, the weekly dose is administered for more than about 180 weeks. In some embodiments, the weekly dose is administered for more than about 190 weeks. In some embodiments, the weekly dose is administered for more than about 200 weeks. In some embodiments, the weekly dose is administered for more than about 210 weeks. In some embodiments, the weekly dose is administered for more than about 220 weeks. In some embodiments, the weekly dose is administered for more than about 230 weeks. In some embodiments, the weekly dose is administered for more than about 240 weeks, or more than about 250 weeks.

In some embodiments, the dosage is in the range of about 0.1 mg per week to about 1 mg per week. In some embodiments, the dosage is in the range of about 1 mg per week to about 2 mg per week. In some embodiments, the dosage is in the range of about 2 mg per week to about 10 mg per week. In some embodiments, the dosage is in the range of about 10 mg per week to about 20 mg per week. In some embodiments, the dosage is in the range of about 20 mg per week to about 40 mg per week. In some embodiments, the dosage is in the range of about 40 mg per week to about 70 mg per week. In some embodiments, the dosage is in the range of about 70 mg per week to about 140 mg per week. In some embodiments, the dosage is in the range of about 140 mg per week to about 280 mg per week. In some embodiments, the dosage is in the range of about 280 mg per week to about 420 mg per week. In some embodiments, the dosage is in the range of about 420 mg per week to about 840 mg per week.

In some embodiments, the AvPAL variant is administered once weekly. In some embodiments, the AvPAL variant is administered twice weekly. In some embodiments, the AvPAL variant is administered four times per week. In some embodiments, the AvPAL variant is administered seven times per week. In some embodiments, the AvPAL variant is administered fourteen times per week. In some embodiments, the AvPAL variant is administered daily.

In some embodiments, the method provided herein comprises administering to the subject the pegylated AvPAL variant at an induction dosage, followed by administering to the subject the pegylated AvPAL variant at a titration dosage, followed by administering to the subject the pegylated AvPAL variant at a maintenance dosage. In some embodiments, the induction dosage is administered for 1-5 weeks, e.g., for 1, 2, 3, 4, or 5 week(s). In some embodiments, the titration dosage is administered for 4-10 weeks, e.g., for 4, 5, 6, 7, 8, 9, or 10 week(s). In some embodiments, the maintenance dosage is administered for 50 or more weeks, such as for 50, 51, 52, 53, 54, 55, 56, 57, 58, 59, 60, 61, 62, 63, 64, 65, 66, 67, 68, 69, 70, or more weeks. In some embodiments, the maintenance dosage is administered for 50 to 70 weeks. In some embodiments, the maintenance dosage is administered for more than 70 weeks.

In some embodiments, the method provided herein comprises administering to the subject the pegylated AvPAL variant at an induction dosage in the range of about 0.1 mg per week to about 10 mg per week, followed by administering to the subject the pegylated AvPAL variant at a titration dosage in the range of about 1 mg per week to about 200 mg per week, followed by administering to the subject the pegylated AvPAL variant at a maintenance dosage in the range of about 20 mg per week to about 840 mg per week. In some embodiments, the induction dosage is administered for 1-5 weeks, e.g., for 1, 2, 3, 4, or 5 week(s). In some embodiments, the titration dosage is administered for 4-10 weeks, e.g., for 4, 5, 6, 7, 8, 9, or 10 week(s). In some embodiments, the maintenance dosage is administered for 50 or more weeks, such as for 50, 51, 52, 53, 54, 55, 56, 57, 58, 59, 60, 61, 62, 63, 64, 65, 66, 67, 68, 69, 70, or more weeks. In some embodiments, the maintenance dosage is administered for 50 to 70 weeks. In some embodiments, the maintenance dosage is administered for more than 70 weeks.

In some embodiments, the method provided herein comprises administering to the subject the pegylated AvPAL variant at an induction dosage in the range of about 2.5 mg per week, followed by administering to the subject the pegylated AvPAL variant at a titration dosage in the range of about 5 mg per week to about 70 mg per week, followed by administering to the subject the pegylated AvPAL variant at a maintenance dosage in the range of about 140 mg per week to about 420 mg per week. In some embodiments, the induction dosage is administered for 1-5 weeks, e.g., for 1, 2, 3, 4, or 5 week(s). In some embodiments, the titration dosage is administered for 4-10 weeks, e.g., for 4, 5, 6, 7, 8, 9, or 10 week(s). In some embodiments, the maintenance dosage is administered for 50 or more weeks, such as for 50, 51, 52, 53, 54, 55, 56, 57, 58, 59, 60, 61, 62, 63, 64, 65, 66, 67, 68, 69, 70, or more weeks. In some embodiments, the maintenance dosage is administered for 50 to 70 weeks. In some embodiments, the maintenance dosage is administered for more than 70 weeks.

In some specific embodiments, the method provided herein comprises administering to the subject the pegylated AvPAL variant at an induction dosage in the range of about 2.5 mg per week for 4 weeks, followed by administering to the subject the pegylated AvPAL variant at a titration dosage in the range of about 5 mg per week to about 70 mg per week for 5 weeks, followed by administering to the subject the pegylated AvPAL variant at a maintenance dosage in the range of about 140 mg per week to about 420 mg per week for 56 to 64 weeks.

In some more specific embodiments, the method provided herein comprises administering to the subject the pegylated AvPAL variant according to the dosing regimen in Table 3.

The pegylated AvPAL variant is described in more detail in the sections below. In some specific embodiments, the pegylated AvPAL variant provided herein is composed of recombinant phenylalanine ammonia lyase (rAvPAL) conjugated to N-hydroxysuccinimide (NHS)-methoxypolyethylene glycol (PEG). The rAvPAL is a homotetrameric protein with a molecular weight of 62 kD per monomer. In some embodiments, to produce the pegylated AvPAL variant (rAvPAL-PEG), an average of nine (9) 20 kD PEG molecules are covalently bound (or conjugated) to each monomer of rAvPAL. In some embodiments, the total molecular weight of the pegylated rAvPAL is approximately 1000 kD. In some embodiments, the amino acid sequence of the rAvPAL monomer is SEQ ID NO:4, in which the serine residues at positions 503 and 565 are underlined:

(SEQ ID NO: 4)
MKTLSQAQSKTSSQQFSFTGNSSANVIIGNQKLTINDVARVARNGTLVSLT

NNTDILQGIQASCDYINNAVESGEPIYGVTSGFGGMANVAISREQASELQT

NLVWFLKTGAGNKLPLADVRAAMLLRANSHMRGASGIRLELIKRMEIFLNA

GVTPYVYEFGSIGASGDLVPLSYITGSLIGLDPSFKVDFNGKEMDAPTALR

QLNLSPLTLLPKEGLAMMNGTSVMTGIAANCVYDTQILTAIAMGVHALDIQ

ALNGTNQSFHPFIHNSKPHPGQLWAADQMISLLANSQLVRDELDGKHDYRD

HELIQDRYSLRCLPQYLGPIVDGISQIAKQIEIEINSVTDNPLIDVDNQAS

YHGGNFLGQYVGMGMDHLRYYIGLLAKHLDVQIALLASPEFSNGLPPSLLG

NRERKVNMGLKGLQICGNSIMPLLTFYGNSIADRFPTHAEQFNQNINSQGY

TSATLARRSVDIFQNYVAIALMFGVQAVDLRTYKKTGHYDARA<u>S</u>LSPATER

LYSAVRHVVGQKPTSDRPYIWNDNEQGLDEHIARISADIAAGGVIVQAVQD

ILP<u>S</u>LH.

The chemical structure of N-hydroxysuccinimide (NHS)-methoxypolyethylene glycol (PEG) is as follows:

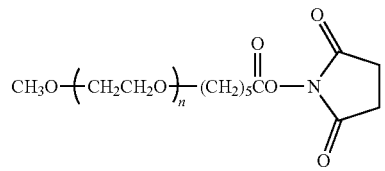

Phenylalanine Ammonia Lyase (PAL) and Variants Thereof

As used herein, "bacterial PAL" and "prokaryotic PAL" are used interchangeably to mean (1) wild-type PAL from a prokaryotic organism, including but not limited to PAL from *Streptomyces maritimus, Nostoc punctiforme, Anabaena variabilis, Anacystis nidulans* (Lofflehardt, Z. Naturforsch. 31(11-12):693-9 (1976), *Photorhabdus luminescens* TT01

(Williams, et al., Microbiology 151:2543-2550 (2005), and *Streptomyces verticillatus* (Bezanson, et al., Can. J. Microbiol. 16(3): 147-51 (1970); (2) fragments, mutants, variants or analogs of such wild-type PAL enzymes that retain similar (i.e., at least 50%) catalytic activity for phenylalanine, and that can, for example, exhibit increased catalytic activity, greater biochemical stability, increased half-life, and/or decreased immunogenicity, and (3) chemically modified versions of such wild-type PAL enzymes or fragments, mutants, variants or analogs thereof that are linked to other chemical moieties that provide other advantageous effects, such as, for example and not for limitation, enhanced half-life and/or decreased immunogenicity. For example, any references to methods of making or using prokaryotic PAL, and fragments, mutants, variants, analogs or chemically modified versions thereof, and compositions of such enzyme(s), for therapeutic purposes, are meant to refer to methods of making, using or formulating all such wild-type prokaryotic PAL or fragments, mutants, variants, analogs or chemical modifications thereof.

One embodiment is a prokaryotic PAL from *Anabaena variabilis* (SEQ ID NO:1) (see FIG. 7A) or biologically active fragment, mutant, variant or analog thereof.

The elucidation of a reliable three-dimensional structure or structural model for a specific macromolecule permits rational design to become a productive method for optimization of specific structure and/or function of said macromolecule. Methods of using a three-dimensional structure or structural model for optimizing PAL enzymes are described in U.S. Pat. No. 7,553,653, which is herein incorporated by reference in its entirety. A high-resolution three-dimensional protein crystal structure of a prokaryotic PAL can be used in methods involving protein engineering to improve the biochemical and biophysical properties of a prokaryotic PAL, and to increase the in vivo therapeutic effectiveness of a prokaryotic PAL. In certain embodiments, provided herein are prokaryotic PAL variants with greater phenylalanine-converting activity and/or reduced immunogenicity as compared to a wild-type prokaryotic PAL. Also provided herein are prokaryotic PAL variants with greater biochemical stability and/or biochemical half-life as compared to a wild-type prokaryotic PAL.

Previous experiments have described modified forms of PAL, such as PAL mutants (Schuster, et al, FEBS Lett. 349(2):252-254 (1994); Schuster, et al, Proc Natl Acad Sci USA 92(18):8433-8437 (1995); Langer, et al, Biochemistry 36: 10867-10871 (1997); El-Batal, et al, Acta Microbiol Pol. 49(1):51-61 (2000); Rother, et al, Eur. J. Biochem. 269: 3065-3075 (2002)) and HAL mutants (Taylor, et al, J. Biol. Chem. 269(44):27473-27477 (1994); Baedeker, et al, Eur. J. Biochem. 269(6): 1790-1797 (2002)).

The biologically active sites of wild-type PAL provided herein can be modified to optimize PAL kinetic characteristics. Km, the concentration of substrate that gives half-maximal activity, is intimately associated with the therapeutic efficacy of PAL in maintaining Phe levels within an acceptable range, i.e., 120 µM to 240 µM. Km is the affinity of the enzyme for the substrate. By controlling affinity, one can limit or control the efficacy of any enzyme against substrate at different concentrations. For example, if Km is 1000 µM (e.g., PAL from *Rhodosporidium toruloides*), the activity of the enzyme will be reduced to about 12.5% at blood Phe levels of 240 µM and to about 3% at blood Phe levels of 60 µM. If Km is 240 µM, the activity of the enzyme will be reduced to about 50%>at blood Phe levels of 240 µM and to about 12% at blood Phe levels of 60 µM. If Km is 120 µM, the activity of the enzyme will be reduced to about 70%>at blood Phe levels of 240 µM and to about 35%>at blood Phe levels of 60 µM. Optimally, a therapeutic objective would be to have an enzyme with sufficient activity to reduce but also maintain Phe within the optimal range of about 120 µM to about 240 µM. An enzyme with a high Km (i.e., 1000 µM) will lose activity rapidly as Phe levels drop to within normal range and will also require the impractical administration of highly concentrated or large volumes of doses. On the other hand, an enzyme with a very low Km can rapidly deplete Phe levels, which may be fatal for hyperphenylaninemias, but can be useful in the management of a disease or disorder.

In some embodiments, the biologically active modified PAL has a kcat of at least about 0.1 s-1 or greater than about 0.5 s-1. In other embodiments, the biologically active modified PAL has a kcat of at least about 0.2 s-1 or greater than about 1.0 s-1. In other embodiments, the biologically active modified PAL has a Km of between about 10 µM to about 1000 µM. In other embodiments, the biologically active modified PAL has a Km of between about 100 µM to about 1000 µM. In other embodiments, the biologically active modified PAL exhibits enzymatic activity that is from about two-fold to about 1000-fold times greater than that of the wild-type. In other embodiments, the biologically active modified PAL exhibits enzymatic activity that is from about 10% to about 100% higher than that of the wild-type. Such biological active modified PAL proteins can be formed using methods well known in the art, such as by site-directed mutagenesis.

A number of strategies are currently used to reduce protein immunogenicity. In certain embodiments, modifications that are introduced to minimize the immune response do not destroy the structure, function, or stability of the macromolecule. Effective strategies used include increasing human sequence content (chimeras and/or other humanization approaches), improving solution properties, removing antibody epitopes, introducing chemical derivatization (such as pegylation), and/or identifying and removing MHC agretopes.

Modification of antigenic surface protein regions reduces immunogenicity (Chirino, et al, Drug Discov. Today 9(2): 82-90 (2004)). One method of improvement involves the construction of smaller sized proteins that retain catalytic activity {e.g., an absorbance assay is used for activity measurement). Protein engineering coupled to ELISA screening, can also be used to identify mutants with reduced immunoreactivity. Another method introduces point mutations for additional surface Lys sites for pegylation derivatization, a method shown to reduce immunogenicity with the test enzyme purine nucleoside phosphorylase (Hershfield, et al. (1991), ibid.). An alternative pathway uses mutation of residues located in protein epitope regions to remove immunogenic sites (Yeung, et al, J. Immunol. 172(11):6658-6665 (2004)). In an approach that is analogous to antibody humanization, homologous loop regions and/or residues from human antibodies are substituted into the corresponding loop regions of a homologous protein.

Improving solution properties of proteins can increase specific enzyme activity and/or reduce immunogenicity. One solution property typical of bacterially expressed recombinant proteins is the formation of protein aggregates due, for example, to inter-chain disulfide bind formation, hydrophobic interactions and/or divalent cations (Chi, et al, Pharm. Res. 20(9): 1325-1336 (2003)). Aggregation of recombinantly expressed proteins can enhance the immune response (Hermeling, et al, Pharm. Res. 21(6): 897-903 (2994); Schellekens, Nephrol. Dial. Transplant. 20(suppl 6):vi3-9

(2005)). One method of improvement involves substituting surface cysteine residues with other amino acid residues (e.g., serine) to minimize the possibility of formation of inter-chain disulfide bonds. For example, substitution of two surface cysteine residues with serine residues reduced the aggregation of chorismate lyase with minor effects on enzyme activity (Holden, et al., Biochim. Biophys. Acta 1594(1): 160-167 (2002)).

Also provided herein are prokaryotic PAL variants that have the similar or greater phenylalanine-converting activity and/or reduced immunogenicity as compared to a wild-type PAL. Further provided herein are prokaryotic PAL variants that comprise one or more amino acids residues (e.g., cysteine) that have been substituted by another amino acid residues (e.g., serine) to reduce protein aggregation that can be associated with decreased enzyme activity, increased immunogenicity, and/or other disadvantageous effects, such as reduced bioavailability, in vivo. In some embodiments, provided herein are pharmaceutical compositions wherein one or more amino acid residues of the prokaryotic PAL variant have been substituted by another amino acid. In some embodiments, the substitution increases phenylalanine-converting activity and/or reduces immunogenicity as compared to the wild-type PAL.

In certain embodiments of the present methods or uses, the prokaryotic PAL variant is an *Anabaena variabilis* PAL (AvPAL) variant. In some embodiments, one or more amino acid residues of the AvPAL variant have been substituted by another amino acid residue. In some embodiments, one or more cysteine residues of the AvPAL variant have been substituted by a serine residue. In some embodiments, the one or more cysteine residues of the AvPAL variant that have been substituted by one or more serine residues are selected from the group consisting of cysteine residues at positions 503 and 565. In specific embodiments, the cysteine residue at position 503 of the AvPAL variant has been substituted by a serine residue (e.g., SEQ ID NO:2). In certain embodiments, the cysteine residue at position 565 of the AvPAL variant has been substituted by a serine residue (e.g., SEQ ID NO:3). In a certain embodiment, the cysteine residues at positions 503 and 565 of the AvPAL variant have been substituted by serine residues (e.g., SEQ ID NO:4).

Prokaryotic PAL variants can also include fusion proteins in which the PAL enzyme has been fused to another heterologous polypeptide, such as a native or modified constant region of an immunoglobulin or a fragment thereof that retains the salvage epitope, known in the art to increase half-life.

Pegylated PAL

Macromolecule chemical modification can be performed in a non-specific fashion (leading to mixtures of derivatized species) or in a site-specific fashion (based on wild-type macromolecule reactivity-directed derivatization and/or site-selective modification using a combination of site-directed mutagenesis and chemical modification) or, alternatively, using expressed protein ligation methods (Hofmann, et al., Curr. Opin. Biotechnol. 13(4):297-303 (2002)). In certain embodiments, chemical modification is used to reduce immunogenicity. Pegylation is a demonstrated method to reduce immunogenicity of proteins (Bhadra, et al., Pharmazie 57(1):5-29 (2002)), but glycosylation and other chemical derivatization procedures, using modification with phosphorylation, amidation, carboxylation, acetylation, methylation, creation of acid-addition salts, amides, esters, and N-acyl derivatives are also possible (Davis, Science 303:480-482 (2004)).

A series of different pegylation reactions on PAL, using a range of PEG chemical reagent to PAL protein ratios, will provide PEG-PAL derivatives for each modification method. The optimal degree of pegylation can be determined based upon the residual activity obtained for each derivatized PAL species using the absorbance assay in combination with PAGE and native gel analysis, or by using SE-HPLC with multiangle light scattering (MALS), to determine the extent of PEG derivatization. After initial ranges of optimal modification are determined, comparative kinetic analysis (including Vmax and Km determinations, binding constants of substrates, proteolytic stability, pH dependence of activity, temperature-dependence of activity) and immunoreactivity of optimal PEG-PAL species can be determined by ELISA, immunoprecipitation, and Western blot. Protein engineering can also be used to generate the most favorable PAL mutant for pegylation using the optimal derivatization conditions; by minimizing the size of the PAL protein and only modifying the most antigenic regions of the PAL surface, cost of PEG modification will be reduced while at the same time retaining the maximum amount of enzymatic activity and minimum amount of immunogenicity. Similarly, site-specific pegylation can be used to provide enzyme derivatives.

Other chemical modifications such as phosphorylation or other chemical modification of Lys, Arg, and Cys residues can be used to mask immunogenic regions and/or proteolytic sensitive regions. Such chemical modifications include the polymer addition method of Bednarsaki and the Altus Corporation cross-linking method for improving PAL stability, reducing immunogenicity, and improving protease resistance are representative examples. Bednarsaki demonstrated that polymer addition improves protein temperature stability (Wang, et al., J. Am. Chem. Soc. 114(1):378-380 (1992)), and Altus Corporation has found that glutaraldehyde cross-linking improves enzyme stability.

To discover if the in vivo therapeutic half-life of a protein such as PAL would benefit from pegylation, a variety of different PEG:PAL conjugates are synthesized, characterized in vitro and tested in vivo for L-Phe reduction. In order to both optimize the potential effects of pegylation and to identify one or more sites of PEG attachment, a design strategy is employed wherein polymer length, conformation, and the degree of PEG attachment is varied. In some embodiments, methods for preparing the pegylated PAL generally comprise: (a) reacting PAL with polyethylene glycol under conditions whereby PAL becomes attached to one or more PEG groups, and (b) obtaining the reaction product(s). Because the specific sites of PAL modification might significantly alter the intrinsic activity of the conjugate, different types and amounts of PEG were explored. The chemistry used for pegylation of PAL was the acylation of the primary amines of PAL using the NHS-ester of methoxy-PEG (O—[(N-Succinimidyloxycarbonyl)-methyl]-O'-methylpolyethylene glycol). Acylation with methoxy-PEG-NHS or methoxy-PEG-SPA results in an amide linkage that eliminates the charge from the original primary amine.

The present methods provide for a substantially homogenous mixture of polymer:protein conjugate. "Substantially homogenous" as used herein means that only polymer:protein conjugate molecules are observed. The polymer:protein conjugate has biological activity and the present "substantially homogenous" pegylated PAL preparations provided herein are those which are homogenous enough to display the advantages of a homogenous preparation, e.g., ease in clinical application in predictability of lot to lot pharmacokinetics.

The polymer molecules contemplated for use in the pegylation approaches described herein can be selected from among water-soluble polymers or a mixture thereof. The water-soluble polymer can be selected from the group consisting of, for example, polyethylene glycol, monomethoxy-polyethylene glycol, dextran, poly-(N-vinyl pyrrolidone), propylene glycol homopolymers, a polypropylene oxide/ethylene oxide co-polymer, polyoxyethylated polyols (e.g., glycerol), HPMA, Fleximer™, and polyvinyl alcohol, mono-(C1-C10)alkoxy-PEG, aryloxy-PEG, tresyl monomethoxy PEG, PEG propionaldehyde, bis-succinimidyl carbonate PEG, cellulose, or other carbohydrate-based polymers. The polymer selected should be water-soluble so that the protein to which it is attached does not precipitate in an aqueous environment, such as a physiological environment. The polymer can be branched or unbranched. In some embodiments, for therapeutic use of the end-product preparation, the polymer will be pharmaceutically acceptable.

In some embodiments, a water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol.

The proportion of polyethylene glycol molecules to protein molecules will vary, as will their concentrations in the reaction mixture. In general, the optimum ratio (in terms of efficiency of reaction in that there is no excess unreacted protein or polymer) will be determined by the molecular weight of the polyethylene glycol selected and on the number of available reactive groups (typically amino groups) present. In general, the higher the molecular weight of the polymer used, the fewer number of polymer molecules which can be attached to the protein. Similarly, branching of the polymer can be taken into account when optimizing these parameters. Generally, the higher the molecular weight (or the more branches) the higher the polymer:protein ratio. Several different linear PEG polymer lengths are contemplated, including but not limited to, 5 kDa and 20 kDa, conjugates of two-armed branched PEG polymers, including but not limited to 10 kDa and 40 kDa. In some embodiments, for the PEGylation reactions contemplated herein, the average molecular weight is about 2 kDa to about 100 kDa (the term "about" indicating +/−1 kDa). In other embodiments, the average molecular weight is about 5 kDa to about 40 kDa.

Examples 7 through 9 of co-owned U.S. Pat. No. 7,531,341, which is herein incorporated by reference in its entirety, describe the effects of pegylated and nonpegylated forms of lysine mutant R91K PAL from *Rhodosporidium toruloides* (RtPAL), NpPAL and AvPAL on Phe levels in the ENU2 or BTBR$^{enu2}$ mouse. This animal model is a homozygous mutant at the PAH locus resulting in an animal with severe hyperphenylalaninemia. The high plasma Phe levels make this animal the appropriate model for evaluating the ability of PAL to reduce plasma Phe. Administration of pegylated forms of NpPAL and AvPAL resulted in greater reduction in Phe in the ENU2 mice as compared to unpegylated NpPAL and AvPAL, respectively. Such effects were maintained for NpPAL upon weekly injections over a ten-week period. These results show that pegylation of PAL from the cyanobacteria, *Nostoc punctiforme* and *Anabaena variabilis*, is essential in reducing Phe levels in PKU affected mice.

The effect of serine substitution of the cysteine residues (e.g., at positions 503 and 565) in the AvPAL polypeptide on Phe levels in ENU2 mice has also been shown. The administration of the pegylated AvPAL double cysteine mutant (at positions 503 and 565) AvPAL_C565SC503S results in a reduction in plasma Phe that is comparable to that achieved with pegylated wild-type AvPAL. It has been shown that AvPAL_C565SC503S has in vivo PAL enzyme activity that is comparable to the pegylated wild-type AvPAL, and has reduced immunogenicity compared to the pegylated wild-type AvPAL.

Pegylated PAL variants with reduced immunogenicity are provided herein. One embodiment is a pegylated form of AvPAL variant with reduced immunogenicity. Specific embodiments contemplate AvPAL variants in which pegylation is achieved by reacting the AvPAL variant with a water-soluble polymer, e.g., polyethylene glycol (PEG). In some embodiments, pegylation is achieved by reacting the AvPAL variant once with PEG at a ratio of at least 1:1, at least 1:1.5, at least 1:2, at least 1:3, at least 1:4, at least 1:5, at least 1:6, at least 1:7, at least 1:8, at least 1:9, or at least 1:10 (PAL:PEG). In one embodiment, the PAL variant is an AvPAL variant, and the pegylation is achieved using a PAL:PEG ratio of about 1:1 to about 1:20. In another embodiment, the PAL variant is an AvPAL variant, and the pegylation is achieved using a PAL:PEG ratio of about 1:3 to about 1:12. In yet another embodiment, the PAL variant is an AvPAL variant, and the pegylation is achieved using a PAL:PEG ratio of about 1:5 to about 1:10. In yet another embodiment, the PAL variant is an AvPAL variant, and the pegylation is achieved using a PAL:PEG ratio of about 1:9.

In certain embodiments, one or more lysine residues are introduced at and/or near the active site of a prokaryotic PAL variant to enhance catalytic activity, reduce immunogenicity and/or improve biochemical stability, in part by blocking potential pegylation of other amino acid residues (e.g., tyrosine) at and/or near the active site of the enzyme or by blocking potential pegylation of a lysine residue important for enzyme activity. Without being bound to a particular theory, it is hypothesized that a tyrosine residue at and/or near the active site of a prokaryotic PAL (i.e., position 78 or 314 in AvPAL) can be a site for pegylation, which reduces enzyme activity. In some embodiments, one or more amino acid residues at and/or near the active site of the prokaryotic PAL, which are not required for enzyme activity, are substituted by a lysine residue. In a certain embodiment, the prokaryotic PAL is AvPAL. In one embodiment, the AvPAL tyrosine residue at position 78 or 314 is not accessible for pegylation. Again without being bound to a particular theory, it is hypothesized that a lysine residue of a prokaryotic PAL (i.e., position 419 in AvPAL), which is normally blocked from pegylation due to pegylation of a neighboring lysine residue PAL (i.e., position 413 in AvPAL), can be a site for pegylation, which reduces substrate binding and/or catalytic activity. In some embodiments, one or more amino acid residues of the prokaryotic PAL are substituted by a lysine residue, such that a lysine residue important for the enzyme's substrate binding and/or catalytic activity is not accessible for pegylation. In a specific embodiment, the prokaryotic PAL is AvPAL. In one embodiment, the AvPAL lysine residue at position 419 is not accessible for pegylation.

In some embodiments, the composition comprises highly purified prokaryotic PAL variant derived from bacteria, or a biologically active fragment, mutant or analog thereof alone or in combination with a pharmaceutically suitable carrier. In some embodiments, preparations contain prokaryotic PAL variant with a purity greater than about 90%, 95%, 96%, 97%, 98%, 99%, 99.2%, 99.5%, 99.6%, 99.7%, 99.8%, or 99.9%. In other embodiments, the relative specific activity of the prokaryotic PAL variant is at least about 50%, or greater than about 110%, of the specific activity of wild-type prokaryotic PAL.

Such prokaryotic PAL variants can be isolated and purified in accordance with the methods known in the art and is thereby present in amounts which enable using the prokaryotic PAL enzyme therapeutically. In some embodiments, a cDNA encoding for a complete or wild-type prokaryotic PAL is used. However, in other embodiments, a cDNA encoding for a biologically active fragment, mutant, variant or analog thereof can be used. Furthermore, provided herein are compositions of optimized prokaryotic PAL obtained by structure-based molecular engineering approaches and/or chemically-modified (e.g., pegylated) forms of PAL. Specific embodiments contemplate optimal compositions of prokaryotic PAL with improved specific activity, enhanced stability, reduced immunogenicity and/or proteolytic sensitivity appropriate for therapeutic use. In some embodiments, the PAL is a pegylated form of *Anabaena variabilis* PAL with improved specific activity, enhanced stability, reduced immunogenicity and/or proteolytic sensitivity.

In some embodiments, the pegylated prokaryotic PAL variant is an AvPAL variant and the cysteine residues at position 503 of AvPAL has been substituted with a serine residue (SEQ ID NO:2). In some embodiments, the pegylated prokaryotic PAL variant is an AvPAL variant and the cysteine residues at position 565 of AvPAL has been substituted with a serine residue (SEQ ID NO:3). In some embodiments, the pegylated prokaryotic PAL variant is an AvPAL variant and the cysteine residues at positions 503 and 565 of AvPAL have been substituted with serine residues (SEQ ID NO:4).

Prokaryotic PAL Compositions, Pharmaceutical Compositions and Formulations

The present disclosure contemplates pharmaceutical compositions comprising therapeutically effective amounts of prokaryotic PAL compositions of the disclosure together with one or more pharmaceutically acceptable excipients, vehicles diluents, stabilizers, preservatives, solubilizers, emulsifiers, adjuvants and/or carriers. Such pharmaceutical compositions include diluents of various buffer content (e.g., Tris-HCl, phosphate), pH and ionic strength; additives such as detergents and solubilizing agents (e.g., Polysorbate 20, Polysorbate 80), anti-oxidants (e.g., ascorbic acid, sodium metabisulfite), preservatives (e.g., Thimerosol, benzyl alcohol) and bulking substances (e.g., lactose, mannitol); see, e.g., Remington's Pharmaceutical Sciences, 18$^{th}$ Edition (1990, Mack Publishing Co., Easton, Pa.) pages 1435:1712, which are herein incorporated by reference. An effective amount of active ingredient is a therapeutically, prophylactically, or diagnostically effective amount, which can be readily determined by a person skilled in the art by taking into consideration such factors as body weight, age, and therapeutic goal.

The prokaryotic PAL pharmaceutical compositions of the present disclosure may include a buffering agent to maintain the pH of the solution within a desired range. Preferred buffering agents include Tris-HCl, sodium acetate, sodium phosphate, and sodium citrate. Mixtures of these buffering agents may also be used. The amount of buffering agent useful in the composition depends largely on the particular buffer used and the pH of the solution. For example, acetate is a more efficient buffer at pH 5 than pH 6 so less acetate may be used in a solution at pH 5 than at pH 6. A more preferred buffering agent is Tris-HCl. A preferred pH range for the pharmaceutical compositions of the present disclosure is about pH 6.0-8.5. A more preferred pH range for the pharmaceutical compositions of the present disclosure is about pH 7.0-8.0. A most preferred pH range for the pharmaceutical compositions of the present disclosure is about pH 7.0-7.6.

The pharmaceutical compositions of the present disclosure may further include an isotonicity-adjusting agent to render the solution isotonic and more compatible for injection. A preferred agent is sodium chloride within a concentration range of 50-200 mM. A more preferred agent is sodium chloride within a concentration range of 100-150 mM. A most preferred agent is sodium chloride within a concentration range of 130-150 mM.

Pharmaceutically acceptable carriers or excipients may include stabilizers, which are molecules that stabilize the prokaryotic PAL compositions of the disclosure. The term "stabilize" as used herein, is meant to include, for example and not for limitation, increasing the shelf-life of a prokaryotic PAL enzyme, protecting the prokaryotic PAL enzyme from proteolytic digestion, maintaining the prokaryotic PAL enzyme in an active conformation, and preserving the prokaryotic PAL enzyme activity upon storage at elevated temperatures.

Stabilizers of the present disclosure include L-phenylalanine (Phe) and structural analogs thereof, such as trans-cinnamic acid (t-CA), benzoic acid, tyrosine (Tyr), and the like. Loss of activity of a plant PAL from *Phaseolus vulgaris* (PvPAL) has been shown upon removal of its substrate L-phenylalanine after affinity purification (Da Cunha, Eur. J. Biochem. 178:243-248 (1988)), and a yeast PAL from *Rhodosporidium toruloides* (RtPAL) has been shown to be protected from protease inactivation by tyrosine (Wang, et al., Mol. Genet. Metab. 86:134-140 (2005); Pilbak, et al., FEBS J. 273:1004-1019 (2006)). As shown herein below, Phe and certain of its structural analogs have the ability to stabilize PEG:PAL conjugates of a prokaryotic PAL from *Anabaena variabilis* (AvPAL) (see EXAMPLE 11). Without being bound to a particular theory, it is hypothesized that the prokaryotic PAL enzyme is more stable as an enzyme-substrate complex, wherein the bound substrate Phe is converted to the product t-CA or to a transition state analog of t-CA. The t-CA remains bound to the otherwise highly reactive active site center (MIO group), thereby stabilizing the PAL enzyme. Accordingly, the PAL enzyme substrate, Phe, product, t-CA, or structural analogs thereof are stabilizers of the disclosure.

The disclosure contemplates a pharmaceutical composition comprising a prokaryotic PAL variant and a pharmaceutically acceptable carrier, wherein the pharmaceutically acceptable carrier comprises a stabilizer. The stabilizer is Phe or structural analog thereof. The stabilizer is selected from the group consisting of L-phenylalanine, trans-cinnamic acid and benzoic acid. A preferred range for the stabilizers of the disclosure is from about 0.1 to 20 moles of stabilizer per mole active site of prokaryotic PAL. A more preferred range for the stabilizers of the disclosure is from about 0.5 to 10 moles of stabilizer per mole active site of prokaryotic PAL. A most preferred range for the stabilizers of the disclosure is from about 1 to 10 moles of stabilizer per mole active site of prokaryotic PAL.

In some embodiments, the pharmaceutical composition comprises a prokaryotic PAL variant and a pharmaceutically acceptable carrier, wherein the prokaryotic PAL variant has a greater phenylalanine-converting activity and/or a reduced immunogenicity as compared to a wild-type PAL and is effective in reducing the Phe concentration in the blood, serum or plasma of the subject to a range from below the level of detection to between about 20 µM to 60 µM, preferably to less than about 20 μM, and even more preferably to less than about 10 μM, and wherein the pharmaceutically acceptable carrier comprises a stabilizer. In some embodiments, the stabilizer is Phe or structural analog thereof. In some embodiments, the stabilizer is selected from the group consisting of L-phenylalanine, trans-cinnamic acid and benzoic acid.

In some specific embodiments, the pharmaceutical composition comprises a prokaryotic PAL variant and a pharmaceutically acceptable carrier, wherein the prokaryotic PAL variant is an *Anabaena variabilis* PAL (AvPAL) variant, wherein the cysteine residues at positions 503 and 565 of the AvPAL variant have been substituted by serine residues, the AvPAL variant further comprises a water-soluble polymer of polyethylene glycol, wherein the ratio of AvPAL variant and the polyethylene glycol is about 1:3; and the AvPAL variant is effective in reducing the phenylalanine concentration in the blood, serum or plasma of the subject to a range from below the level of detection to between about 20 μM to 60 μM, preferably to less than about 20 μM, and even more preferably to less than about 10 μM, and wherein the pharmaceutically acceptable carrier comprises a stabilizer. In some embodiments, the stabilizer is Phe or structural analog thereof. In some embodiments, the stabilizer is selected from the group consisting of L-phenylalanine, trans-cinnamic acid and benzoic acid.

In some more specific embodiments, the pharmaceutical composition provided herein comprises an AvPAL variant comprising an amino acid sequence of SEQ ID NO:2, SEQ ID NO:3 or SEQ ID NO:4, and trans-cinnamic acid. In some embodiments, the AvPAL variant comprises the amino acid sequence of SEQ ID NO:2. In some embodiments, the AvPAL variant comprises the amino acid sequence of SEQ ID NO:3. In some embodiments, the AvPAL variant comprises the amino acid sequence of SEQ ID NO:4. In some embodiments of the various pharmaceutical compositions described above, the pharmaceutical composition further comprises sodium chloride, and tromethamine and tromethamine hydrochloride.

As used herein, when contemplating prokaryotic PAL variant compositions, the term "therapeutically effective amount" refers to an amount that is effective to produce the intended beneficial effect on health of a patient. In some embodiments, a therapeutically effective amount of a prokaryotic PAL variant gives a decrease in blood, plasma or serum, preferably plasma, L-phenylalanine levels that provides benefit to the patient. The amount will vary from one individual to another and will depend upon a number of factors, including the overall physical condition of the patient, diet and disease state. The amount of prokaryotic PAL used for therapy gives an acceptable decrease in blood, plasma or serum, preferably plasma, L-phenylalanine levels, and maintains this value during PAL treatment at a beneficial level (typically in a range from less than about 5% to between about 35% and 100%, preferably in a range from less than about 5% to about 35%, and even more preferably in a range from less than about 5% to about 15% of the normal range of blood, plasma or serum, preferably plasma, L-phenylalanine). In some embodiments, a therapeutically effective amount of a prokaryotic PAL variant reduces tumor growth, tumor size or tumor burden by greater than about 10%, 30%, 50%, 70%, 90%, 95%, 98% or 99% in a treated patient as compared to an untreated patient. In some embodiments, a therapeutically effective amount of a prokaryotic PAL variant maintains the tumor in static condition in a treated patient as compared to an untreated patient. In some embodiments, a therapeutically effective amount of a prokaryotic PAL variant increases survival time or disease-free time at least about 10%, 20%, 50%, 100%, 2-fold, 5-fold or 10-fold longer in a treated patient as compared to an untreated patient. A therapeutically effective amount of the prokaryotic PAL variant compositions of the disclosure may be readily ascertained by one skilled in the art using publicly available materials and procedures.

The disclosure provides for administering prokaryotic PAL variants less frequently than native PAL. The dosing frequency will vary depending upon the condition being treated, but in general will be about one time per week. It is understood that the dosing frequencies actually used may vary somewhat from the frequencies disclosed herein due to variations in responses by different individuals to the prokaryotic PAL variants; the term "about" is intended to reflect such variations. It is contemplated that the prokaryotic PAL variants are administered about two times per week, about one time per week, about one time every two weeks, about one time per month, or longer than about one time per month.

The present disclosure may thus be used to reduce blood, plasma or serum L-phenylalanine levels. Numerous conditions, where depletion of blood, plasma or serum L-phenylalanine levels would be beneficial, may be treated with the prokaryotic PAL variant pharmaceutical compositions of the disclosure.

The prokaryotic PAL pharmaceutical compositions prepared in accordance with the present disclosure are preferably administered by parenteral injection, either intravenously, intraperitoneally, subcutaneously, intramuscularly, intraarterially or intrathecally. However, it would be clear to one skilled in the art that other routes of delivery could also be effectively utilized using the pharmaceutical compositions of the present disclosure.

The methods described herein use prokaryotic PAL pharmaceutical compositions comprising the molecules described above, together with one or more pharmaceutically acceptable excipients, vehicles, diluents, stabilizers, preservatives, solubilizers, emulsifiers, adjuvants and/or carriers, and optionally other therapeutic and/or prophylactic ingredients. Such excipients include liquids such as water, saline, glycerol, polyethylene glycol, hyaluronic acid, ethanol, cyclodextrins, modified cyclodextrins (i.e., sufobutyl ether cyclodextrins), etc. Suitable excipients for non-liquid formulations are also known to those of skill in the art.

Pharmaceutically acceptable salts can be used in the compositions of the present disclosure and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in Remington's Pharmaceutical Sciences, $18^{th}$ Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include a therapeutically effective amount of the prokaryotic PAL in combination with a pharmaceutically acceptable carrier and, in addition, may include other pharmaceutical agents, adjuvants, diluents, buffers, etc.

In general, the prokaryotic PAL pharmaceutical compositions of this disclosure will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is intravenous using a convenient daily dosage regimen, which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., a prokaryotic PAL variant composition as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, or softgel capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid or lyophilized forms suitable for reconstitution, solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. In addition, parenteral administration may involve the use of a slow release or sustained release system such that a constant level of dosage is maintained.

The prokaryotic PAL compositions of the disclosure described herein can be administered to a patient at therapeutically effective doses. The toxicity and therapeutic efficacy of such prokaryotic PAL compositions can be determined by standard pharmaceutical procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prokaryotic PAL compositions exhibiting large therapeutic indices are normally preferred.

Identifying and Monitoring Patient Populations

As discussed herein throughout, it will be necessary in various embodiments of the present disclosure to determine whether a given patient is responsive to PAL therapy, and to determine the phenylalanine concentrations of the patient both initially to identify the class of PKU patient being treated and during an ongoing therapeutic regimen to monitor the efficacy of the regimen. Exemplary such methods are described herein below.

BH4 Loading Test

The BH4 loading test allows discrimination between patients that have HPA due to a deficit in BH4 or through a deficiency in PAH.

The simplest BH4 loading test is one in which exogenous BH4 is administered and the effects of the administration on lowering of plasma Phe concentrations is determined. Intravenous loading of 2 mg/kg BH4 was initially proposed by Danks, et al., Lancet 1:1236 (1976), as BH4 of greater purity has become available it has become possible to perform the test using an oral administration of BH4 in amounts of about 2.5 mg/kg body weight. Ultimately, a standardized approach was proposed by Niederwieser et al. in which a 7.5 mg/kg single oral dose of BH4 is administered (Niederwieser, et al., Eur. J. Pediatr. 138:441 (1982)), although some laboratories do still use upwards of 20 mg BH4/kg body weight.

In order for the simple BH4 loading test to produce reliable results, the blood Phe levels of the patient need to be higher than 400 µM. Therefore, it is often customary for the patient to be removed from the PKU diet for 2 days prior to performing the loading test. A BH4 test kit is available and distributed by Dr. Schircks Laboratories (Jona, Switzerland). This kit recommends a dosage of 20 mg BH4/kg body weight about 30 minutes after intake of a normal meal.

Determination of Phe Concentrations

There are numerous methods for determining the presence of Phe in blood (Shaw et al., Analytical Methods in Phenylketonuria-Clinical Biochemistry, In Bickett et al. Eds., Phenylketonuria and Some Other Inborn Errors of Amino Acid Metabolism, Stuttgart, Georg Thiem Verlag, 47-56 (1971)). Typically, phenylalanine and tyrosine concentrations are determined from the serum of a patient using a fluorometric assay. This assay relies on the formation of fluorescent substance when phenylalanine is heated with ninhydrin in the presence of leucylalanine (McCaman, et al., J. Lab. Clin. Med. 59:885-890 (1962)).

The most popular method for determining Phe concentrations is the Guthrie test in which discs are punctured from filter paper that has been saturated with a blood sample from the patient. The uniform discs are incubated in a tray of agar that has been seeded with *Bacillus subtilis* and contains a specific inhibitor of *Bacillus subtilis* growth. As the phenylalanine transfers from the uniform discs onto the agar, the Phe reverse the inhibition of bacterial growth thereby yielding an area of bacterial growth that can be correlated to phenylalanine concentration by comparison to similar assays performed using discs containing known amounts of Phe.

Other methods of quantifying Phe concentration include HPLC, mass spectrometry, thin layer chromatography and the like. Such methods can be used to determine the plasma Phe concentration of a patient before the therapy and to monitor the Phe concentration during the therapeutic regimen to determine the efficacy thereof.

It is contemplated that the plasma Phe levels of the patients will be monitored at convenient intervals (e.g., daily, every other day or weekly) throughout the time course of the therapeutic regimen. By monitoring the plasma Phe levels with such regularity, the clinician will be able to assess the efficacy of the treatment and adjust the PAL and/or dietary protein requirements accordingly.

Combination Therapy

Certain methods of the invention involve the combined use of PAL and dietary protein restriction to effect a therapeutic outcome in patients with various forms of HPA. To achieve the appropriate therapeutic outcome in the combination therapies contemplated herein, one would generally administer to the subject the PAL composition and the dietary restriction in a combined amount effective to produce the desired therapeutic outcome (i.e., a lowering of plasma Phe concentration and/or the ability to tolerate greater amounts of Phe/protein intake without producing a concomitant increase in plasma Phe concentrations). This process may involve administering the PAL composition and the dietary protein therapeutic composition at the same time. This may be achieved by administering a single composition or pharmacological protein formulation that includes all of the dietary protein requirements and also includes the PAL within said protein formulation. Alternatively, the dietary protein (supplement or normal protein meal) is taken at about the same time as a pharmacological formulation (tablet, injection or drink) of PAL. PAL also may be formulated into a protein bar or other foodstuff such as brownies, pancakes, cake, suitable for ingestion.

In other alternatives, PAL treatment may precede or follow the dietary protein therapy by intervals ranging from minutes to hours. In embodiments where the protein and the PAL compositions are administered separately, one would generally ensure that a significant period of time did not expire between the time of each delivery, such that PAL will still be able to exert an advantageously effect on the patient. In such instances, it is contemplated that one would administer the PAL within about 2-6 hours (before or after) of the dietary protein intake, with a delay time of only about 1 hour being most preferred. In certain embodiments, it is contemplated that PAL therapy will be a continuous therapy where a daily dose of PAL is administered to the patient indefinitely. In other situations, e.g., in pregnant women having only the milder forms of PKU and HPA, it may be that PAL therapy is only continued for as long as the woman is pregnant and/or breast feeding.

Further, in addition to therapies based solely on the delivery of PAL and dietary protein regulation, the methods of the present invention also contemplate combination therapy with a third composition that specifically targets one or more of the symptoms of HPA. For example, it is known that the deficit in tyrosine caused by HPA results in a deficiency in neurotransmitters dopamine and serotonin. Thus, in the context of the present invention, it is contemplated that PAL and dietary protein based methods could be further combined with administration of L-dopa, carbidopa and 5-hydroxytryptophan neurotransmitters to correct the defects that result from decreased amounts of tyrosine in the diet.

As the administration of PAL would not generate tyrosine (unlike administration of PAH), such treatment will still result in tyrosine being an essential amino acid for such patients. Therefore, dietary supplementation with tyrosine may be desirable for patients receiving PAL in combination with the BH4 therapy.

Dietary Protein

In addition to administering prokaryotic PAL compositions to the subjects, it is contemplated that the dietary protein of the patients also may be restricted or modified. Those of skill in the art are aware of various commercially available protein formulas for use in the treatment of PKU. Such formulas include MAXIMAID, PHENEX 1, PHENEX 2 (Ross Laboratories, Liverpool, UK), LOFENALAC, PHENYL-FREE (Mead-Johnson), and the like.

Those of skill in the art may use the referenced protein formulas, which are generally free of Phe concentrations. The protein formulas often are supplemented with amino acids that are deficient in PKU patients. Such amino acids include, for example, L-tyrosine, and L-glutamine.

Further, as it is known that L-carnitine and taurine, which are normally found in human milk and other foodstuffs of animal origin, also should be supplied in addition to the protein restriction. In certain embodiments, the L-carnitine may be supplied as 20 mg/100 g of protein supplement, and the taurine may be supplied as 40 mg/100 g protein supplement in order to help supply amounts of these factors normally found in human milk and foods of animal origin.

In addition, those of skill in the art are referred to the 2000 National Academy of Sciences-National Research Council Dietary Reference Intakes for a further listing of other components, such as essential vitamins and minerals that should be supplied to the patient to ensure that other supplements are being provided despite the dietary protein restriction.

Referring to the discussion above regarding total protein amounts and desirable plasma Phe concentrations, one of skill in the art will be able to determine the amount of dietary protein restriction that is required and thus adjust the diet of the patient accordingly. Upon administering prokaryotic PAL to that subject, determining whether the methods of the disclosure are effective will entail determining the plasma Phe concentrations of the patient on a regular basis to ensure that the plasma Phe concentrations remain in a range from below the level of detection to between about 20 $\mu$M to 60 $\mu$M, preferably to less than about 20 $\mu$M, and even more preferably to less than about 10 $\mu$M. Tests for determining such concentrations are described below. Preferably, concentrations of less than the level of detection to between about 20 $\mu$M to 60 $\mu$M are achieved, more preferably to less than about 20 $\mu$M, and even more preferably to less than about 10 $\mu$M.

In certain embodiments, the disclosure provides a method for treating a subject comprising administering to a subject in need of such treatment a therapeutically effective amount of a pharmaceutical composition comprising a prokaryotic phenylalanine ammonia-lyase (PAL) variant and a pharmaceutically acceptable carrier, wherein the PAL variant has a greater phenylalanine-converting activity and/or a reduced immunogenicity as compared to a wild-type PAL, and is effective in reducing the phenylalanine concentration in the blood, serum or plasma of the subject to a range from below the level of detection to between about 20 $\mu$M to 60 $\mu$M, preferably to less than about 20 µM, and even more preferably to less than about 10 µM, and further comprising administering to the subject a protein-restricted (i.e., phenylalanine-free) diet.

To achieve the appropriate therapeutic outcome in the combination therapies contemplated herein, preferably one would generally administer to the subject the prokaryotic PAL composition and the dietary restriction in a combined amount effective to produce the desired therapeutic outcome (i.e., a lowering of plasma Phe concentration to a range from below the level of detection to optimally about 20 µM to 60 µM, preferably to less than about 20 µM, and even more preferably to less than about 10 µM, using standard detection methods well known in the art). This process may involve administering the prokaryotic PAL composition and the dietary protein therapeutic composition at the same time. This may be achieved by administering a single composition or pharmacological protein formulation that includes all of the dietary protein requirements and also includes the prokaryotic PAL within said protein formulation. Alternatively, the dietary protein (supplement or normal protein meal) is taken at about the same time as a pharmacological formulation (tablet, injection or drink) of prokaryotic PAL. Prokaryotic PAL also may be formulated into a protein bar or other foodstuff such as brownies, pancakes, cake, suitable for ingestion.

As the administration of prokaryotic PAL would not generate tyrosine (unlike administration of PAH), such treatment will still result in tyrosine being an essential amino acid for such patients. Therefore, dietary supplementation with tyrosine may be desirable for patients receiving prokaryotic PAL alone in combination with the dietary protein therapy.

In other alternatives, prokaryotic PAL treatment may precede or follow the dietary protein therapy by intervals ranging from minutes to hours. In embodiments where the protein and the prokaryotic PAL compositions are administered separately, one would generally ensure that a significant period of time did not expire between the time of each delivery, such that PAL will still be able to exert an advantageously effect on the patient. In such instances, it is contemplated that one would administer the PAL within about 2-6 hours (before or after) of the dietary protein intake, with a delay time of only about 1 hour being most preferred. In certain embodiments, it is contemplated that PAL therapy will be a continuous therapy where a daily dose of PAL is administered to the patient indefinitely.

Production of Prokaryotic PAL

Another aspect of the invention is a method of producing prokaryotic PAL. In a preferred embodiment, recombinant PAL is over-expressed as an N-terminal octahistidyl-tagged fusion protein in a vector preferably E. coli BL21 (DE3)/pLysS (Invitrogen) with an inducible promoter such as with IPTG (isopropyl-beta-D-thiogalactopyranoside). In another preferred embodiment, recombinant PAL is over-expressed in E. coli BL21 (DE3)/pLysS cells without an N-terminal tag. Seed culture for a bioreactor/fermenter is grown from a glycerol stock in shake flasks. Such seed culture is then used to spike into a controlled bioreactor in fed-batch mode. Glucose is supplemented and pH is controlled with base (NH4OH) and agitation is up to 1200 rpm. $O_2$ feed keeps dissolved oxygen to greater than 20%. The cells are grown at a temperature of 30° C. until reaching and $OD_{600}$ of 70-100 (~22-25 hrs) and then induced with 0.4 mM IPTG. The temperature is reduced to 22 to 26° C. and grown until activity change is <0.1 IU/ml (approximately 40-48 hrs and an $OD_{600}$ typically of 200). Cell culture media is typically defined and composed of yeast extract protein, peptone-tryptone, glucose, glycerol, casamino acids, trace salts and phosphate buffering salts. The recombinant PAL product is produced intra-cellularly and not secreted. The bacteria are harvested by continuous centrifugation (Alfa-Laval, Carr, Ceba, or equivalent).

Purification of Prokaryotic PAL

A further aspect of the present invention features a method to purify bacterial PAL or a biologically active fragment, mutant or analog thereof. According to a first embodiment, a transformed cell mass is grown and ruptured leaving crude recombinant enzyme. Exogenous materials are normally separated from the crude bulk to prevent fouling of the columns. Chromatographic purification is conducted using one or several chromatographic resins. Subsequently, the purified protein is formulated into a buffer designed to provide stable activity over an extended period of time. In another preferred embodiment, the method to purify the bacterial PAL comprises: (a) lysis of the bacteria containing recombinant PAL using a pressure homogenizer (but potentially by other physical means such as glass bead lysis); (b) heat treatment; (c) clarification of this lysate using a second continuous centrifugation step and/or depth filtration (as with Cuono Zeta Plus or Maximizer, Pall Filtron, or Millipore Millistak or Opticao filters); (d) passage through a charcoal filtration step (as with Millipore Millistak 40AC); (e) passage through a final filtration step (as with a Sartorious Sartopore 0.2 µm filter); (f) passage over a butyl hydrophobic interaction chromatography (as in Toyopearl Butyl 650M from Tosoh Biosciences); (g) passage over a Q ion exchange column (as in a Macroprep High Q from BioRad); and (h) recovery of final product by buffer exchange with tangential flow filtration (as with a Sartorious Hydrosart or PES100 kDa membrane). Those skilled in the art readily appreciate that one or more of the chromatography steps may be omitted or substituted, or that the order of the chromatography steps may be changed within the scope of the present invention. Finally, appropriate sterilizing steps may be performed as desired.

Having now generally described the invention, the same may be more readily understood through the following reference to the following examples. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Therapeutic Uses and Administration

Various Forms of Hyperphenylalaninemia (HPA)

Provided herein are methods of treating a variety of HPA patient populations comprising the use of pharmaceutical compositions provided herein, either alone or in combination with other therapeutic regimens, for managing HPA and/or PKU. In particular, it is contemplated that the pharmaceutical compositions provided herein can be used to treat the patient population with phenylalanine concentrations that are low enough that dietary intervention is not normally used (i.e., patients with mild HPA), patients with moderate PKU, patients with classic or severe PKU, and any subpopulations thereof.

Certain embodiments are directed to treating classic severe PKU by administering to the subject a protein-restricted diet in combination with a composition comprising prokaryotic PAL variant or a biologically active variant, mutant, or fragment thereof, wherein the combined administration of the protein-restricted diet and prokaryotic PAL variant is effective to lower the phenylalanine concentration in the plasma of said subject as compared to said concentration in the absence of said combined administration. In specific embodiments, therapy is contemplated for a patient who manifests Phe levels greater than 420 μM. In another specific embodiments, therapy is contemplated for a patient who manifests Phe levels greater than 500 μM. In yet another specific embodiments, therapy is contemplated for a patient who manifests Phe levels greater than 550 μM. In yet specific embodiments, therapy is contemplated for a patient who manifests Phe levels greater than 600 μM. In specific embodiments, therapy is contemplated for a patient who manifests Phe levels greater than 650 μM.

Other embodiments entail administering the pharmaceutical composition comprising prokaryotic PAL variant provided herein to any individual that has HPA, characterized by a plasma Phe concentration greater than 180 μM prior to the administration of prokaryotic PAL variant, in an amount effective to produce a decrease in such a plasma Phe concentration of the patient.

Characteristics of Severe Classical PKU and Methods of Treatment Thereof

Severe PKU manifests in a plasma Phe concentration greater than 1200 μM and can be found to be as high as 4800 μM. Patients that have this disorder must be treated with a Phe-free diet in order to bring their plasma Phe concentrations down to a level that is clinically acceptable (typically, less than 600 μM or less than 300 μM). These patients are only able to tolerate a maximum of between 250-350 mg dietary Phe per day (Spaapen et al., Mol. Genet Metab. 78:93-99 (2003)). As such, these patients are started on a Phe-restricted formula diet between 7-10 days after birth and are burdened with this dietary restriction for the remainder their lifespan. Any alleviation of the strict dietary restrictions that these individuals are encumbered with would be beneficial.

The tests used for the diagnosis of individuals with classical Phe are described in further detail here. These tests have revealed that patients with classical severe PKU require a low phenylalanine diet (Lucke et al, Pediatr. Neurol. 28:228-230 (2003)). Thus, it is contemplated that certain methods provided herein will entail determining that the patient is suffering from classical PKU by monitoring the plasma Phe concentration of the individual. The patient can then be treated by administering the pharmaceutical composition comprising the prokaryotic PAL variant provided herein alone or a combined regimen of a low protein diet and PAL variant such that there is produced at least a 25% decrease in the plasma Phe concentrations of the patient. In some embodiments, the method will produce a 30% decrease in the plasma Phe concentration. In other embodiments, the method will produce a 40%, 50%, 60%, 70%, 80%, 90% or greater decrease in the plasma Phe concentration of the individual (for example, where a patient with severe classical PKU has a Phe concentration of 4800 μM a 90% decrease in the Phe concentration will produce a plasma Phe concentration of 480 μM, a concentration that is sufficiently low to require little dietary restriction). Of course, it should be understood that the treatment methods provided herein, whether for treating severe classical PKU or any other HPA described herein, should attempt to lower the plasma Phe concentrations of the patient to levels as close to a range of about 120 μM to about 360 μM±15 μM as possible, or to an optimal range of about 120 μM to about 240 μM.

In some embodiments, the plasma Phe concentrations of the classical PKU patient being treated is reduced from any amount of unrestricted plasma Phe concentration that is greater than 1000 μM to any plasma Phe level that is less than 600 μM. Of course, even if the combined treatment with prokaryotic PAL variant and the protein-restricted diet produces a lesser decrease in plasma Phe concentration, e.g., to a level of between 800 μM to about 1200 μM, this will be viewed as a clinically useful outcome of the therapy because patients that have a plasma Phe concentration in this range can manage the disease by simply restricting the amount of protein in the diet as opposed to eating a Phe-restricted formula, thereby resulting in a marked improvement in the quality of life of the individual, as well as leading to greater patient compliance with the dietary restriction.

Any increase in the amount of dietary Phe levels that can be tolerated by the patient as a result of the treatment will be considered to be a therapeutically effective outcome. For example, it is contemplated that as a result of administering the prokaryotic PAL variant therapy, the patient will be able to increase his/her intake of dietary Phe from 250-350 mg/day to 350-400 mg/day (i.e., the Phe tolerance phenotype of the patient is altered from that of a classic PKU patient to a moderate PKU patient). It would be desirable that the therapeutic intervention taught herein would allow the patient to increase his/her intake of dietary Phe from 250-350 mg/day to 400-600 mg/day (i.e., the Phe tolerance phenotype of the patient is altered from that of a classic PKU patient to a mild PKU patient), or in some cases, to allow the patient to have an intake of greater than 600 mg Phe/day (i.e., normal dietary intake).

Characteristics of BH4-Non-Responsive PKU Patients and Methods of Treatment Thereof A second group of patients that can be treated with the pharmaceutical compositions and methods provided herein are those individuals that have been determined to have an elevated plasma Phe concentrations i.e., any concentration that is greater than 200 μM, but have been diagnosed to be non-responsive to BH4 therapy (as determined by the BH4 loading test described below). Such patients can include those individuals that have mild PKU (i.e., plasma Phe concentrations of up to 600 μM), individuals that have moderate PKU (i.e., plasma Phe concentrations of between 600 μM to about 1200 μM), as well as patients that have classic severe PKU (i.e., plasma Phe concentrations that are greater than 1200 μM).

In some embodiments, patients that are non-responsive to BH4 therapy are given PAL variant in combination with a reduced amount of protein in their diet in order to decrease the plasma Phe concentrations of the patient. The administration of prokaryotic PAL variant can produce a greater decrease in the plasma Phe concentrations of the patient as compared to the decrease that is produced with the same dietary protocol administered in the absence of prokaryotic PAL variant therapy. The dietary restrictions can be a diet that restricts the Phe intake by providing a synthetic medical protein formula that has a diminished amount of Phe or alternatively, the dietary restriction can be one which simply requires that the patient limit his/her overall protein intake but nevertheless allows the patient to eat normal foodstuffs in limited quantities.

The therapeutic outcomes discussed for classical PKU patients are incorporated into the present section by reference. For example, the therapeutic outcomes for patients with moderate PKU (i.e., patients that has an unrestricted plasma Phe concentration of 600 μM to 1200 μM) can include at least a 25% decrease in the plasma Phe concentrations of the patient. In some embodiments, the method will produce a 30% decrease in the plasma Phe concentration. In other embodiments, the method will produce a 40%, 50%, 60%, 70%, 80%, 90% or greater decrease in the plasma Phe concentration of the individual (for example, where a patient with moderate classical PKU has a Phe concentration of 1000 μM, a 90% decrease in the Phe concentration will produce a plasma Phe concentration of 100 μM, a concentration that is sufficiently low to require little or no dietary restriction).

In some embodiments, the plasma Phe concentrations of the moderate PKU patient being treated is reduced from any amount of unrestricted plasma Phe concentration that is between 600 μM to 1200 μM to any plasma Phe level that is less than 300 μM. In one embodiment, treatment with prokaryotic PAL variant (either alone or in combination with a dietary restriction) produces a decrease in plasma Phe concentration, e.g., to a level of between 200 μM to about 400 μM, which will be viewed as a clinically useful outcome of the therapy because patients that have a plasma Phe concentration in this range can manage the disease by simply restricting the amount of protein in the diet as opposed to eating a Phe-restricted formula. Indeed, in many studies, it is taught that such patients can even eat a normal diet.

Any increase in the amount of dietary Phe levels that can be tolerated by the patient as a result of the treatment will be considered to be a therapeutically effective outcome. For example, it is contemplated that as a result of administering the prokaryotic PAL variant therapy (either alone or in combination with other therapeutic intervention), the patient will be able to increase his/her intake of dietary Phe from 350-400 mg/day to 400-600 mg/day (i.e., the Phe tolerance phenotype of the patient is altered from that of a moderate PKU patient to a mild PKU patient). Of course, it would be desirable that the therapeutic intervention taught herein would allow the patient to increase his/her intake of dietary Phe from 350-400 mg/day to have an intake of greater than 600 mg Phe/day (i.e., normal dietary intake).

A patient manifesting only mild PKU, i.e., has a dietary allowance of 400-600 mg Phe intake/day, can be treated using the compositions and methods provided herein and can benefit from the prokaryotic PAL variant-based therapies because it is desirable to produce a normalized plasma Phe concentration that is as close to 360 μM±15 μM as possible. For such patients, an advantageous therapeutic outcome will include at least a 25% decrease in the plasma Phe concentrations of the patient. In one embodiment, the method will produce a 30% decrease in the plasma Phe concentration. In another embodiment, the method will produce a 40%>, 50%>, 60%>, or greater decrease in the plasma Phe concentration of the individual (for example, where a patient with mild PKU has a Phe concentration of 600 μM, a 60% decrease in the Phe concentration will produce a plasma Phe concentration of 360 μM, i.e., an acceptable, normal concentration of plasma Phe).

In some embodiments, the plasma Phe concentrations of the mild PKU patient being treated is reduced from any amount of non-restricted plasma Phe concentration that is between 400 μM to 600 μM to any plasma Phe level that is less than 100 μM. Of course, even if the treatment with prokaryotic PAL variant (either alone or in combination with a dietary restriction) produces a lesser decrease in plasma Phe concentration, e.g., to a level of between 200 μM to about 400 μM, this will be viewed as a clinically useful outcome of the therapy.

Any increase the amount of dietary Phe levels that can be tolerated by the patient as a result of the treatment will be considered to be a therapeutically effective outcome. For example, it is contemplated that as a result of administering the prokaryotic PAL variant therapy (either alone or in combination with other therapeutic intervention), the patient will be able to increase his/her intake of dietary Phe from 400-600 mg/day (i.e., the Phe tolerance phenotype of the patient is altered from that of a mild PKU patient to a mild HPA patient) to allow the patient to have an intake of greater than 600 mg Phe/day (i.e., normal dietary intake). [00145] Furthermore, even if the patient is one who only manifests the symptoms of non PKU HPA, i.e., has an elevated plasma Phe concentration of up to 600 μM, but is otherwise allowed to eat a normal protein diet will benefit from prokaryotic PAL variant therapy because it has been shown that elevated Phe concentrations have significant effects on the IQ of such individuals.

For the sake of conciseness, certain abbreviations are used herein. One example is the single letter abbreviation to represent amino acid residues. The amino acids and their corresponding three letter and single letter abbreviations are as follows:

| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Each publication, patent application, patent, and other reference cited herein is incorporated by reference in its entirety to the extent that it is not inconsistent with the

8. EMBODIMENTS

Embodiment 1. A method for reducing blood phenylalanine concentration in a subject, comprising administering to the subject a weekly dose of a formulation comprising an AvPAL variant, wherein the subject is about 12 years old to about 18 years old, and wherein the weekly dose is administered for more than about 50 weeks, wherein the AvPAL variant comprises an amino acid sequence of SEQ ID NO:2, SEQ ID NO:3 or SEQ ID NO:4.

Embodiment 2. The method of embodiment 1, wherein the weekly dose is administered for more than about 60 weeks, more than about 70 weeks, more than about 80 weeks, more than about 90 weeks, more than about 100 weeks, more than about 110 weeks, more than about 120 weeks, more than about 130 weeks, more than about 140 weeks, more than about 150 weeks, more than about 160 weeks, more than about 170 weeks, more than about 180 weeks, more than about 190 weeks, more than about 200 weeks, more than about 210 weeks, more than about 220 weeks, more than about 230 weeks, more than about 240 weeks, or more than about 250 weeks.

Embodiment 3. The method of embodiment 1 or 2, wherein the dosage is in the range of about 0.1 mg per week to about 1 mg per week.

Embodiment 4. The method of embodiment 1 or 2, wherein the dosage is in the range of about 1 mg per week to about 2 mg per week.

Embodiment 5. The method of embodiment 1 or 2, wherein the dosage is in the range of about 2 mg per week to about 10 mg per week.

Embodiment 6. The method of embodiment 1 or 2, wherein the dosage is in the range of about 10 mg per week to about 20 mg per week.

Embodiment 7. The method of embodiment 1 or 2, wherein the dosage is in the range of about 20 mg per week to about 40 mg per week.

Embodiment 8. The method of embodiment 1 or 2, wherein the dosage is in the range of about 40 mg per week to about 70 mg per week.

Embodiment 9. The method of embodiment 1 or 2, wherein the dosage is in the range of about 70 mg per week to about 140 mg per week.

Embodiment 10. The method of embodiment 1 or 2, wherein the dosage is in the range of about 140 mg per week to about 280 mg per week.

Embodiment 11. The method of embodiment 1 or 2, wherein the dosage is in the range of about 280 mg per week to about 420 mg per week.

Embodiment 12. The method of embodiment 1 or 2, wherein the dosage is in the range of about 420 mg per week to about 840 mg per week.

Embodiment 13. The method of any one of embodiments 1-12, wherein the AvPAL variant is administered once weekly.

Embodiment 14. The method of any one of embodiments 1-12, wherein the AvPAL variant is administered twice weekly.

Embodiment 15. The method of any one of embodiments 1-12, wherein the AvPAL variant is administered four times per week.

Embodiment 16. The method of any one of embodiments 1-12, wherein the AvPAL variant is administered seven times per week.

Embodiment 17. The method of any one of embodiments 1-12, wherein the AvPAL variant is administered fourteen times per week.

Embodiment 18. The method of any one of embodiments 1-12, wherein the AvPAL variant is administered daily.

Embodiment 19. The method of embodiment 1, wherein the method comprises: (1) administering to the subject the AvPAL variant at an induction dosage in the range of about 0.1 mg per week to about 10 mg per week, followed by (2) administering to the subject the AvPAL variant at a titration dosage in the range of about 1 mg per week to about 200 mg per week, followed by (3) administering to the subject the AvPAL variant at a maintenance dosage in the range of about 20 mg per week to about 840 mg per week.

Embodiment 20. The method of embodiment 19, wherein the induction dosage is about 2.5 mg per week.

Embodiment 21. The method of embodiment 19 or 20, wherein the titration dosage is in the range of about 5 mg per week to about 70 mg per week.

Embodiment 22. The method of any one of embodiments 19 to 21, wherein the maintenance dosage is in the range of about 140 mg per week to about 420 mg per week.

Embodiment 23. The method of any one of embodiments 19 to 22, wherein the induction dosage is administered for a duration of between about 2 week and about 6 weeks, the titration dosage is administered for a duration of between about 3 weeks and about 8 weeks, and the maintenance dosage is administered for a duration of between about 50 weeks and about 80 weeks.

Embodiment 24. The method of embodiment 23, wherein the induction dosage is administered for a duration of about 4 weeks, the titration dosage is administered for a duration of about 5 weeks, and the maintenance dosage is administered for a duration of between about 56 weeks and 64 weeks.

Embodiment 25. The method of embodiment 23, wherein the maintenance dosage is comprised of a first maintenance dosage of between about 70 mg per week and about 280 mg per week, a second maintenance dosage of between about 140 mg per week and about 560 mg per week, and a third maintenance dosage of between about 210 mg per week and about 840 mg per week.

Embodiment 26. The method of embodiment 25, wherein the first maintenance dosage is administered for a duration of between about 16 weeks and about 24 weeks, the second maintenance dosage is administered for a duration of about 16 weeks, and the third maintenance dosage is administered for a duration of about 24 weeks.

Embodiment 27. The method of an one of embodiments 19 to 26, wherein following the administration of the maintenance dosage, the method further comprises administering to a subject the AvPAL variant an extension dosage in the range of about 20 mg per week to about 840 mg per week.

Embodiment 28. The method of embodiment 27, wherein the extension dosage is administered for a duration of between about 40 weeks and about 120 weeks.

Embodiment 29. The method of embodiment 28, wherein the induction dosage is administered for a duration of about 4 weeks, the titration dosage is administered for a duration of about 5 weeks, the maintenance dosage is administered for a duration of between about 64 weeks, and the extension dosage is administered for a duration of about 80 weeks.

Embodiment 30. The method of any one of embodiments 19 to 29, wherein the method further comprises assessing the blood phenylalanine concentration prior to administering the induction dosage.

Embodiment 31. The method of embodiment any one of embodiments 19 to 30, wherein the method further comprises assessing the blood phenylalanine concentration after administration of one or more induction dosages, titration dosages, maintenance dosages, and/or extension dosages.

Embodiment 32. The method of embodiment 31, wherein the method further comprises adjusting the dosage based on the blood phenylalanine concentration.

Embodiment 33. The method of embodiment 32, wherein the dosage is adjusted to attain a blood phenylalanine concentration of below about 600 μM.

Embodiment 34. The method of embodiment 32, wherein the dosage is adjusted to attain a blood phenylalanine concentration of below about 360 μM.

Embodiment 35. The method of embodiment 33, wherein the maintenance dosage is increased if blood phenylalanine concentration is greater than about 360 μM.

Embodiment 36. The method of any one of embodiments 1 to 35, wherein the subject has phenylketonuria (PKU).

Embodiment 37. The method of any one of embodiments 1 to 36, wherein the subject is between about 12 years old and about 15 years old.

Embodiment 38. The method of any one of embodiments 1 to 36, wherein the subject is between about 16 years old and about 17 years old.

Embodiment 39. The method of any one of embodiments 1 to 38, wherein the AvPAL variant comprises the amino acid sequence of SEQ ID NO:2.

Embodiment 40. The method of any one of embodiments 1 to 38, wherein the AvPAL variant comprises the amino acid sequence of SEQ ID NO:3.

Embodiment 41. The method of any one of embodiments 1 to 38, wherein the AvPAL variant comprises the amino acid sequence of SEQ ID NO:4.

Embodiment 42. The method of any one of embodiments 1 to 41, wherein the AvPAL variant is pegylated.

Embodiment 43. The method of embodiment 42, wherein said pegylation is achieved by reacting the AvPAL variant with NHS-activated polyethylene glycol at a ratio of at least 1.6 polyethylene glycol per lysine residue of AvPAL variant.

Embodiment 44. The method of embodiment 42, wherein said pegylation is achieved by reacting the AvPAL variant with NHS-activated polyethylene glycol at a ratio of at least 2.4 polyethylene glycol per lysine residue of AvPAL variant.

Embodiment 45. The method of embodiment 42, wherein said pegylation is achieved by reacting the AvPAL variant with NHS-activated polyethylene glycol at a ratio of 3 polyethylene glycol per lysine residue of AvPAL variant.

Embodiment 46. The method of embodiment 42, wherein said pegylation is achieved by reacting the AvPAL variant with NHS-activated polyethylene glycol at a ratio of 5 polyethylene glycol per lysine residue of AvPAL variant.

Embodiment 47. The method of embodiment 42, wherein said pegylation is achieved by reacting the AvPAL variant with NHS-activated polyethylene glycol at a ratio of 6 polyethylene glycol per lysine residue of AvPAL variant.

Embodiment 48. The method of embodiment 42, wherein said pegylation is achieved by reacting the AvPAL variant with NHS-activated polyethylene glycol at a ratio of 7 polyethylene glycol per lysine residue of AvPAL variant.

Embodiment 49. The method of embodiment 42, wherein said pegylation is achieved by reacting the AvPAL variant with NHS-activated polyethylene glycol at a ratio of 8 polyethylene glycol per lysine residue of AvPAL variant.

Embodiment 50. The method of embodiment 42, wherein said pegylation is achieved by reacting the AvPAL variant with NHS-activated polyethylene glycol at a ratio of 9 polyethylene glycol per lysine residue of AvPAL variant.

Embodiment 51. The method of any one of embodiments 1 to 50, wherein the AvPAL variant is adminstered as a formulation comprising a pharmaceutically acceptable carrier comprising a stabilizer.

Embodiment 52. The method of embodiment 51, wherein the stabilizer is L-phenylalanine or structural analog thereof.

Embodiment 53. The method of embodiment 52, wherein the stabilizer is selected from the group consisting of L-phenylalanine, trans-cinnamic acid and benzoic acid.

Embodiment 54. The method of embodiment 53, wherein the stabilizer is trans-cinnamic acid.

Embodiment 55. The method of embodiment 54, wherein the formulation further comprises sodium chloride, and tromethamine and tromethamine hydrochloride.

A number of embodiments of the invention have been described. Nevertheless, it will be understood that various modifications may be made without departing from the spirit and scope of the invention. Accordingly, the descriptions in the Experimental section are intended to illustrate but not limit the scope of invention described in the claims.

9. EXAMPLES

9.1 Example 1: Effects of AvPAL Variants on Subjects Aged 16 to 17 Years

Studies were performed to investigate the effect a PEGylated form of an AvPAL polypeptide variant (e.g., with serine substitution of the cysteine residues at positions 503 and 565 (SEQ ID NO:4)) on adolescent/young adult PKU patients aged 16 to 17 years.

Methods of preparing pegylated AvPAL double cysteine mutant AvPAL_C565SC503S are described in co-owned U.S. Pat. No. 7,534,595B2, which is herein incorporated by reference in its entirety. The pegylated AvPAL double cysteine mutant AvPAL_C565SC503S was prepared as described in Example 10 of U.S. Pat. No. 7,534,595B2.

The study designs for PRISM-1 (165-301, NCT01819727) and PRISM-2 (165-302, NCT01889862) have been described previously (Thomas J A et al. *Mol Genet Metab*. 2018; 124(1):27-38). The safety, efficacy, and immunogenicity of pegvaliase for the 11 subjects who were aged 16 or 17 years at the time of consent was assessed.

Subject Exposure and Disposition

Exposure to pegvaliase and disposition for the 11 adolescent/young adult subjects in PRISM-2 were similar to the adult (≥18 years) population. Baseline demographics and characteristics are shown in Table 1.

TABLE 1

| Baseline demographics and characteristics by age for subjects entering PRISM-1 | | |
|---|---|---|
| | Adolescent/ Young Adult | Adults |
| Number of subjects | 11 | 250 |
| Age at consent, Mean (SD), years | 16.6 (0.5) | 29.7 (8.5) |
| Sex Female, n (%) | 7 (63.6) | 123 (49.2) |
| Body mass index, Mean (SD), kg/m² | 24.7 (4.4) | 28.6 (6.8) |
| Weight, Mean (SD), kg | 64.7 (8.8) | 81.2 (20.8) |

TABLE 1-continued

Baseline demographics and characteristics
by age for subjects entering PRISM-1

|  | Adolescent/<br>Young Adult | Adults |
|---|---|---|
| Blood Phe, Mean (SD), μmol/L | 1038.1 (280.5) | 1241.3 (388.5) |
| Blood Phe, Median, μmol/L | 968.0 | 1236.5 |
| Protein from intact food,<br>Mean (SD), g/day | 21.1 (15.3) | 39.3 (27.9) |

The mean (SD) duration of exposure for the adolescent/young adult subjects was 885.5 (645.06) days, with a mean (SD) daily dose of 36.9 (12.70) mg/day. Most adolescent/young adult subjects were administered a mean dose of ≥40 mg/day to <60 mg/day (45.5% [n=5]) or ≥20 mg/day to <40 mg/day (36.4% [n=4]), with 18.2% (n=2) administered a mean dose<20 mg/day and none were administered a mean dose≥60 mg/day. 4 (36%) of the 11 adolescent/young adult subjects discontinued from study drug: 2 (18%) due to an AE, 1 (9%) withdrawn from study drug per investigator decision (due to subject non-compliance), and 1 (9%) lost to follow-up.

Efficacy Results

Like adults, adolescent/young adults receiving long-term dosing of pegvaliase in PRISM-2 Part 4 were able to achieve clinically relevant blood Phe thresholds (<600 μmol/L [European guideline target for patients aged >12 years], <360 μmol/L [American College of Medical Genetics and Genomics (ACMG) target for all patients], <120 μmol/L [upper limit of normal]) (FIGS. 1A-1C) and had a substantial and sustained reduction in mean blood Phe over time, with a mean (SD) of 595.8 (539.07) μmol/L by Week 49 and 500.0 (625.01) μmol/L by Week 169, a reduction from baseline Phe values of 36.8% and 47.1%, respectively.

Safety/Immunogenicity Results

Safety and immunogenicity were assessed by determining the adverse event rates by age group for subjects enrolled in PRISM-2. Results are shown in Table 2. Adverse events (AEs) occurred at a similar rate in both age groups (Table 2). None of the acute systemic hypersensitivity reactions were associated with drug-specific immunoglobulin E and all events resolved without sequelae. Neither of the 2 adolescent/young adult who experienced a serious adverse event (SAE) discontinued from study drug or from the study due to the event. Immunogenicity and pharmacokinetics/pharmacodynamics (PK/PD) profile were consistent between the two age groups. PAL IgG antibodies were found in 100% of subjects and neutralizing antibodies (NAbs) were found in most subjects with mean detectable levels remaining stable or decreasing over time in both age groups.

TABLE 2

Summary of adverse event rates by age
group for subjects enrolled in PRISM2

|  | Adolescent/<br>Young Adults<br>(n = 11) | Adults<br>(n = 204) |
|---|---|---|
| Adverse event (AE) | 11 (100.0%) | 200 (98.0%) |
| Any AE assessed by the investigator as drug related | 10 (90.9%) | 192 (94.1%) |
| Any AE causing permanent study drug discontinuation | 3 (27.3%) | 9 (4.4%) |
| Serious adverse event (SAE) | 2 (18.2%) | 38 (18.6%) |
| SAE assessed by the investigator as drug related | 1 (9.1%) | 18 (8.8%) |
| SAE causing permanent study drug discontinuation | 0 | 5 (2.5%) |
| SAE assessed by the investigator as drug related causing study discontinuation | 0 | 3 (1.5%) |
| SAE causing study discontinuation | 0 | 3 (1.5%) |
| Any hypersensitivity AE | 10 (90.9%) | 175 (85.8%) |
| Acute systemic hypersensitivity reaction | 1 (9.1%) | 7 (3.4%) |
| Severe acute systemic hypersensitivity reaction | 0 | 0 |
| Generalized skin reaction (≥14 Days) | 0 | 90 (44.1%) |
| Injection site skin reaction (≥14 Days) | 6 (54.5%) | 84 (41.2%) |
| Arthralgia | 7 (63.6%) | 140 (68.6%) |
| Injection site reaction | 10 (90.9%) | 154 (75.5%) |
| Death | 0 | 0 |

Results indicate that adolescent/young adult subjects aged 16 to 17 years achieved substantial and sustained blood Phe reductions with pegvaliase dosages up to 60 mg/day with a manageable safety profile for most subjects with long term treatment. The efficacy, safety, and immunogenicity results in adolescent/young adults are consistent with those found in adults, demonstrating a positive benefit:risk profile and supporting inclusion of adolescent/young adult PKU patients aged 16 to 17 years for treatment with pegvaliase. As adherence to dietary management begins to deteriorate during adolescence, pharmacotherapy should be considered to achieve optimum blood Phe control in this patient population.

9.2 Example 2: Clinical Evaluation with
Prokaryotic PAL Compositions for Treatment of
Adolescents Aged 12-17 Years Phenylketonuria (PKU) is a rare autosomal recessive genetic disorder associated with absent or deficient phenylalanine hydroxylase activity. Subsequent elevation of blood phenylalanine (Phe) can cause neurocognitive and psychiatric symptoms. Thus, lifelong dietary management to sustain Phe below recommended thresholds is important. Difficulty sustaining Phe is frequently reported in adolescents as they transition away from childhood and parental oversight of dietary management decreases. Pegvaliase is a pegylated PAL enzyme substitution therapy approved to lower Phe in adults with PKU (Phe>600 μmol/L). The following example provides guidance on the parameters used for the clinical evaluation of compositions comprising prokaryotic PAL or biologically active fragments, mutant, variants or analogs thereof in the therapeutic methods of the present disclosure. The Phase 3 open-label randomized control study is designed to evaluate the safety and efficacy of pegvaliase in adolescents (NCT05270837). As discussed herein throughout, prokaryotic PAL compositions are used in the treatment of adolescent subjects aged 12-17 years. Clinical trials are conducted which provide an assessment of subcutaneous doses of prokaryotic PAL for safety, pharmacokinetics, and initial response of both surrogate and defined clinical endpoints.

Methods

The study is conducted to evaluate the safety and efficacy self-administered subcutaneous injections of pegvaliase in adolescent subjects (aged 12-17 years) with phenylketonuria (PKU). Adolescent subjects aged between 12 and 17 years with PKU are divided into two age cohorts (Cohort A ages 16-17 years and Cohort B ages 12-15 years). Cohorts A and B is enrolled and dosed concurrently (see FIGS. 2A-2C).

Cohort A consists of approximately 25 U.S. subjects 16 to 17 years old who are evaluated using an open-label single-arm study design. The primary efficacy endpoint is the change from baseline in blood Phe at Week 73, which is the end of the Primary Treatment Phase (Part 1). Following Week 73, Cohort A subjects continue to receive open-label pegvaliase in the Extension Phase (Part 2) for up to an additional 80 weeks.

Cohort B consists of 27 U.S. and European subjects 12 to 15 years old, inclusive, who are evaluated using an open-label, 2-arm, randomized control design, with diet-only management of PKU as the control. Subjects are randomized in a 2:1 ratio to the active and control arms, respectively, with 18 subjects receiving pegvaliase and 9 subjects managing their PKU with diet alone. The primary efficacy endpoint is the change from baseline in blood Phe at Week 73, the end of Part 1. After Week 73, the 18 subjects in the active treatment arm continue to receive open-label pegvaliase in the Extension Phase (Part 2) for up to an additional 80 weeks. The 9 subjects in the diet-only control arm initiate pegvaliase treatment beginning Week 74 and, from Weeks 74 through 146, follow the same dosing and assessment schedule that the active subjects in both Cohort A and Cohort B followed from Weeks 1 through 73.

The two-part randomized controlled Phage 3 clinical study is conducted to characterize the risk and benefits of pegvaliase compared with diet only in adolescents, who have a substantial unmet need from current treatment options. The study will enroll approximately 54 adolescents with Phe>600 µmol/L (ages 12-17 years (US), inclusive; 12-15 years (EU), inclusive). In Part 1, participants are randomized 2:1 to pegvaliase (n=36) or dietary management (n=18) and followed for 72 weeks. Following a 4-week induction period and subsequent titration period, the maintenance dose of pegvaliase will be individualized up to a maximum of 60 mg/day depending on patient response. The primary efficacy endpoint is the change from baseline in blood Phe following 72 weeks on study. All participants from Part 1 will continue into Part 2 (beginning Week 73) and will receive pegvaliase treatment until Week 153. In addition to safety and Phe endpoints, neurocognitive changes will be evaluated.

Design Rationale for Separate Cohorts

The rationale for using 2 different designs to study the older (ages 16-17) and younger (ages 12-15) adolescents within a single overarching study is based on an assessment of a way to expeditiously meet the unmet medical need in all adolescent PKU patients within a single study.

Based on extensive clinical experience with evaluating both sapropterin dihydrochloride and pegvaliase in PKU patients, in order to assess blood Phe efficacy in the PKU population, dietary protein intake is maintained steady throughout the study and using individual subjects as their own control in an open-label design. Intra-subject comparison to baseline blood Phe is warranted to demonstrate efficacy, as it controls for the substantial inter-subject variability that results from each subject's individual dietary Phe tolerance (i.e., the amount of dietary Phe that an individual can consume daily while maintaining blood Phe concentrations within a defined target range). Phe tolerance can be driven by physiologic attributes such as residual PAH activity, which is genetically determined and stable, along with the catabolic/anabolic status of the subject.

For Cohort A, consisting of older adolescent PKU patients (ages 16-17) enrolled at centers in the U.S., an open-label single-arm design enhances the safety assessment of pegvaliase by permitting a larger safety database for a given study size since all subjects are on active treatment from the start of study. This is accomplished without losing the insights into safety often generated in a randomized control trial (RCT) design. The Type III immune complex-mediated hypersensitivity events that largely define the safety profile for pegvaliase are not typically observed in the adult or adolescent PKU patient population not receiving pegvaliase. As a result, a comparison of safety data between a pegvaliase treatment group and a control group (whether diet-only or a blinded placebo) is unlikely to uncover safety signals not revealed in an open-label trial. Because the immune system matures prior to adolescence (Olin et al., Cell. 174(5):1277-1292.e14 (2018); Georgountzou et al., Front Immunol. 8:957 (2017)), the immune response to pegvaliase among adolescent subjects is expected to be similar to the responses observed in 16- to 57-year-old study subjects in the pegvaliase clinical development program. Importantly, 12 subjects in the 16- to 17-year-old population have been studied in past pegvaliase clinical trials, as described in Example 1, and their data demonstrate this adolescent population is similar to adults with respect to both safety and efficacy.

For Cohort B, consisting of younger adolescent PKU patients (ages 12-15 years) enrolled at centers in both the EU and the U.S., a randomized control trial (RCT) design, with diet-only management of PKU as the control, ensures the acquisition of robust data in the younger, previously untested adolescent population and minimizes the possibility of bias. A diet control arm is the best comparator for this age group as daily placebo injections would place undue burden on adolescent PKU patients. Dietary control addresses the impact that age might have on response due to the potential for behavioral difference from adults related to dietary compliance. Subjects randomized to diet control continue on their current prescribed diet.

Adolescent subjects in Cohorts A and B are effectively participating in 2 separate cohorts under a single overarching protocol. This is done in an effort to address the unmet need in adolescent PKU patients as efficiently as possible given that the study procedures, dosing and assessment schedules, safety monitoring, and other operational aspects of the study for Cohorts A and B are essentially the same. Combining the cohorts into one study ensures a consistency in study procedures, sites, and key personnel that ensures a more consistent evaluation of safety and efficacy across the 2 cohorts.

Rationale for Dosing Regimen

Pegvaliase is a daily treatment for patients with PKU. Previous clinical studies have suggested the primary clearance mechanism of pegvaliase from plasma is via formation of circulating immune complexes leading to complement activation and removal of the drug by phagocytosis, indicating pegvaliase plasma exposure was driven by immune response. Considering that the immune system matures prior to adolescence (Olin et al., Cell. 174(5):1277-1292.e14 (2018); Georgountzou et al., Front Immunol. 8:957 (2017)), the immune response to pegvaliase among adolescent subjects is expected to be similar to the responses observed in 16 to 57-year-old study subjects in our clinical development program.

Following in-clinic dosing for the initial doses (first 8 weeks), pegvaliase are self-administered by the subject under observation of a parent or guardian (trained adult observer). Self-administration at home makes daily treatment less burdensome for patients, thereby improving treatment compliance. In addition to training in self-administration prior to first in-clinic dose, subjects and trained adult observers receive extensive training on how to monitor and respond to possible adverse events (AEs) that may be associated with study drug treatment.

Pegvaliase is administered using an Induction/Titration/Maintenance (I/T/M) dosing regimen according to Table 3 (modified from the regimen used in Phase 3 studies performed in the US and United States Prescribing Information (USPI)). During pegvaliase clinical development, this dosing regimen was found to help mitigate the onset and severity of hypersensitivity reactions while substantially reducing blood Phe concentrations.

The pegvaliase dose levels in this study have been evaluated in 6 multiple-dose Phase 2 and Phase 3 studies. The dose level for induction is 2.5 mg once weekly and was chosen because this dose with a once weekly dosing frequency administered during the initial 4 weeks of treatment (i.e., induction) has been associated with a lower incidence and severity of hypersensitivity reactions when compared with 5 days per week dosing frequency at a higher starting dose (0.4 mg/kg).

The duration of 73 weeks for Part 1 was chosen because that is the anticipated amount of time it takes, following the protocol-specified dosing schedule, for subjects to reach the 60 mg/day dose level, if needed, to achieve the optimal blood Phe level.

Objectives and Endpoints (Cohorts A and B)

The primary objective is to evaluate the safety and efficacy of pegvaliase in adolescent subjects with PKU.

For Cohort A, the primary efficacy evaluation is the change in blood Phe concentration from treatment naïve baseline to Week 73. For Cohort A (ages 16-17), subjects serve as their own controls. Subjects are assessed for blood Phe concentration during Screening/Run-in (two measurements 2 to 4 weeks apart), pre-dose on Day 1, every 4 weeks up to completion of the Primary Treatment Phase (Part 1), and every 8 weeks in the Extension Phase (Part 2). The primary efficacy evaluation is the change in blood Phe concentration from treatment naïve baseline at Week 73.

For Cohort B (ages 12-15), the change in blood Phe from baseline is compared between subjects in the active (pegvaliase) arm and the control (diet-only) arm. Subjects are assessed for blood Phe concentration during Screening/Run-in (two measurements 2 to 4 weeks apart), pre-dose on Day 1, every 4 weeks up to completion of the Primary Treatment Phase (Part 1), and every 8 weeks in the Extension Phase (Part 2).

Safety variables assessed include: AEs, including serious AEs (SAES); clinical laboratory test (chemistry, hematology, and urinalysis) results; Vital signs (which includes growth); physical examination; electrocardiogram (ECG) test results; and immunogenicity test results (anti-PEG IgG, anti-PEG IgM, anti-PAL IgG, anti-PAL IgM, TAb, NAb, complements C3 and C4, and anti pegvaliase IgE [hypersensitivity reaction visits only]).

Safety assessments in Part 1 are performed at clinic visits occurring weekly for the first 8 weeks, then every 4 weeks through Week 73, with visits occurring every 8 weeks during Part 2. In the weeks when subjects do not have a scheduled clinic visit, telephone assessments are conducted to answer dosing questions and review AEs and concomitant medications. Immunogenicity testing is performed at Day 1, Weeks 4, 8, 12, 16, 20, 24, and every 8 weeks thereafter in the Part 1 and every 8 weeks in Part 2.

Secondary efficacy evaluations are conducted to evaluate the effect of pegvaliase treatment on neurocognitive outcomes in adolescent subjects with PKU. Neurocognitive assessments, using the attention deficit hyperactivity disorder rating scale (ADHD-RS) inattention sub-score and the Behavior Rating Inventory of Executive Function (BRIEF), are performed at Day 1 (Baseline, prior to study drug) and every 12 weeks.

To characterize dietary protein intake from intact food in adolescent subjects with PKU after pegvaliase treatment, the change in protein intake from medical food and/or intact foods after study drug treatment is explored.

To characterize the pharmacokinetics (PK) of pegvaliase in adolescent subjects with PKU, plasma samples for trough PK samples are taken at Day 1 and every 4 weeks for the first 24 weeks, followed by sampling every 8 weeks thereafter during Part 1. Intensive PK sampling is performed at Week 73 in all subjects. Samples are taken at pre-dose, 2, 4, 8, 12, and 24 hours post dose. The 24-hour sample is taken prior to the next daily dose. Trough PK samples are collected every 8 weeks during Part 2.

Tertiary efficacy evaluations are conducted to explore the biochemical, molecular, and cellular aspects of PKU. Blood and urine samples are collected to evaluate biochemical, molecular, and cellular aspects of PKU and to develop the assays used for these evaluations.

Overall Study Design

Subject Eligibility (Cohorts A and B). To evaluate the safety and efficacy of pegvaliase self-administered daily by adolescent subjects (ages 12-17, inclusive) with PKU, the 2 cohorts in the study are enrolled, dosed, and assessed concurrently. Cohort A includes subjects 16-17 years old at Screening and Cohort B includes subjects 12-15 years old at Screening.

Subjects who meet any of the following criteria are not be eligible to participate in the study: previous treatment with pegvaliase; use of any investigational product or investigational medical device within 30 days prior to Screening/Run-in or requirement for any investigational agent prior to completion of all scheduled study assessments; use of any medication that is intended to treat PKU, including the use of large neutral amino acids, within 14 days prior to the administration of study drug on Day 1; use or planned use of any injectable drugs containing polyethylene glycol (PEG; other than pegvaliase), including medroxyprogesterone injection, within 3 months prior to Screening/Run-in and during study participation; a positive test for HIV antibody, hepatitis B surface antigen, or hepatitis C antibody; a history of organ transplantation or on chronic immunosuppressive therapy; a history of substance abuse (as defined by the American Psychiatric Association: Diagnostic and Statistical Manual of Mental Disorders [DSM]) in the past 12 months or current alcohol or drug abuse; pregnant or breastfeeding at Screening/Run-in or planning to become pregnant (self or partner) or breastfeeding at any time during the study; concurrent disease or condition that would interfere with study participation or safety (e.g., history or presence of clinically significant cardiovascular, pulmonary, hepatic, renal, hematologic, gastrointestinal, endocrine, immunologic, dermatologic, neurological, oncologic, or psychiatric disease); major surgery planned during the study period; any condition that, in the view of the investigator, places the subject at high risk of poor treatment compliance or terminating early from the study; alanine aminotransferase (ALT) concentration>2× the upper limit of normal (ULN); and creatinine>1.5×ULN.

Cohort B Design Summary. The design for Cohort B is an open-label, two-arm, randomized control evaluation of 27 subjects 12-15 years old conducted at study sites in the US and EU, with diet only as the control arm. At enrollment, subjects in Cohort B are randomized 2:1 to the active and control arms, with 18 subjects receiving daily pegvaliase and 9 subjects managing PKU by diet alone. Treatment assignment is stratified by baseline blood Phe (average of the last assessments) of ≤1000 µmol/L or >1000 µmol/L. The primary efficacy endpoint is the change from baseline blood Phe at Week 73. Cohort B subjects in the active and control arms follow the same visit schedules and perform the same assessments throughout the 73-week Primary Treatment Phase (Part 1) except that the control subjects do not be receive pegvaliase and do not have PK draws. Details of the induction/titration/maintenance (I/T/M) dosing regimen for the active subjects in Cohort B are as described for Cohort A above. The timing of Part 1 assessments for Cohort B active and control subjects is provided in FIGS. 3 and 5, respectively.

After Week 73, the 18 subjects in the Cohort B active treatment arm continue to receive open-label pegvaliase in the Extension Phase (Part 2) for up to 80 additional weeks. After Week 73 the 9 subjects in the Cohort B control arm initiate pegvaliase treatment and follow a parallel schedule for dosing, study visits, and assessments in Weeks 74 through 146 to that followed by the Part B active arm subjects during the Primary Treatment Phase (Part 1) from Weeks 1 through 73. The timing of Part 2 assessments for Cohort B active and control subjects is provided in FIGS. 4 and 6, respectively.

BRIEF SUMMARY

The purpose of the study is to evaluate the safety and efficacy of pegvaliase and characterize the PK of pegvaliase in adolescent subjects with PKU. Study details include:

Condition/Disease: Phenylketonuria (PKU) is a rare autosomal recessive genetic disorder caused by mutations in the phenylalanine hydroxylase (PAH) gene, leading to an absence or deficiency in PAH enzyme activity and subsequent elevation of the amino acid phenylalanine (Phe) in the blood, known as hyperphenylalaninemia (HPA) (Vockley et al., Genet Med. 16(2):188-200 (2014); Mitchell et al., Genet Med. 13(8):697-707 (2011)). Deficiency of PAH results in abnormally elevated concentrations of Phe, which is toxic to the brain. High Phe levels during infancy and early childhood cause profound neurocognitive and developmental defects, and poorly controlled blood Phe levels in older children and adults are associated with learning disabilities, attention deficit hyperactivity disorder, behavioral problems, and psychiatric symptoms.

Study Hypothesis: The Safety population consists of all subjects who received at least 1 dose of the study drug. The efficacy population consists of all subjects who received at least 1 dose of the study drug during the study and have post-treatment blood Phe measurements. Categorical data is presented using counts and percentages of subjects. Continuous variables are presented using number of subjects, mean, standard deviation (SD), median, minimum, and maximum.

For Cohort A, the primary analysis on efficacy endpoints is descriptive. In addition, a 95% confidence interval of the mean change in blood Phe concentration at Week 73 is presented and compared to 250 µmol/L using an Analysis of Covariance (ANCOVA) model which includes baseline blood Phe as a covariate. For Cohort B, the primary analysis on efficacy (blood Phe concentration at Week 73) is an ANCOVA model which includes baseline blood Phe as covariate and treatment group as factor. The LS mean and 95% confidence intervals are calculated for the treatment difference between pegvaliase and diet only.

Safety analyses are performed on the Safety Population. AEs are coded using the most recent version of Medical Dictionary for Regulatory Activities (MedDRA). The incidence of treatment-emergent AEs, SAES, and AEs of special interest are summarized by MedDRA system organ class, preferred term, relationship to study drug, and severity. Subjects with AEs that result in study drug discontinuation, dosing interruption, or dose level reduction are tabulated. A by-subject listing of all AEs is be provided.

Clinical laboratory data are summarized descriptively at baseline and post-baseline visits. Shift tables are created to summarize the change in Common Terminology Criteria for Adverse Events (CTCAE) grade from baseline to worst post-baseline value. Clinically significant laboratory abnormalities reported as AEs are summarized. Descriptive statistics for vital signs, physical examination results, ECG test results, and immunogenicity test results are also provided. Details of statistical methods are provided in the Statistical Analysis Plan (SAP).

Study Duration: The study duration is up to 157 weeks for Cohort A subjects and Cohort B subjects randomized to active treatment. This includes a 4-week Screening/Run-in period and up to 153 weeks of pegvaliase treatment in Parts 1 and 2. The study duration is 150 weeks for Cohort B subjects randomized to the diet-only control arm. This includes a 4-week Screening/Run-in period, 73 weeks managing PKU with diet alone while following the Part 1 assessment schedule, and 73 weeks of pegvaliase treatment from Week 74 through Week 146 following the same Part 1 assessment schedule.

Treatment Duration (treatment defined as subcutaneous pegvaliase): The treatment duration is up to 153 weeks for Cohort A subjects and those randomized to pegvaliase in Cohort B. The treatment duration is 73 weeks for Cohort B subjects randomized to the diet-only control arm.

Health Measurement/Observation: Reduction in Blood Phe.

Visit Frequency: For subjects in Cohort A and the active (pegvaliase) arm of Cohort B, clinic visits in Part 1 occur weekly for the first 8 weeks, then every 4 weeks through Week 73, and every 8 weeks during Part 2. For subjects in the control (diet only) arm of Cohort B, clinic visits in Part 1 occur weekly for the first 3 weeks, then every 4 weeks in through Week 73. After Week 73, these subjects repeat the visit schedule for Part 1 while initiating pegvaliase treatment: weekly visits for 8 weeks, then every 4 weeks until Week 146.

Number of Subjects: Approximately 25 subjects are enrolled into Cohort A. In subjects (ages 16-57) who completed 17 months of treatment in previous pegvaliase studies utilizing an I/T/M dosing regimen, the mean (standard deviation [SD]) reduction in blood Phe concentration from treatment naïve baseline at Month 17 was 640 µmol/L (570 µmol/L). Assuming a similar treatment effect in adolescent subjects aged 16 to 17 years, including 25 subjects provides more than 90% power to detect a reduction in blood Phe concentration from treatment naïve baseline at Month 17 that is statistically significantly different from 250 µmon. The analysis is based on the 2-sided one sample T-test on blood Phe change from baseline and significance level of 0.05.

Approximately 27 subjects are enrolled into Cohort B and randomized to the pegvaliase or diet only groups in 2:1 ratio. Assuming the mean (SD) reduction in Phe at Week 73 is 640 (570) µmol/L in the pegvaliase group and 100 (250) µmol/L in the diet only group, a total sample size of 27 subjects provides more than 90% power to detect a treatment difference, based on the two-sample T-test with unequal variance and significance level 0.05 (two sided).

Treatment Groups and Duration

The investigational product is pegvaliase (formerly referred to as BMN 165; marketed name Palynziq; recombinant *Anabaena variabilis* phenylalanine ammonia lyase-PEG [rAvPAL-PEG]) and is supplied to subjects in prefilled syringes (PFS) for self-administration. Pegvaliase is provided in PFS in 3 dose strengths: 2.5 mg (0.5 mL of 5 mg/mL protein concentration), 10 mg (0.5 mL of 20 mg/mL protein concentration), and 20 mg (1.0 mL of 20 mg/mL protein concentration).

Subjects receive pegvaliase at a concentration of 5.0 or 20.0 mg/mL. Pegvaliase is administered subcutaneously at dose levels in the range of 2.5 to 60 mg. The minimum dose of pegvaliase is 2.5 mg/week. The maximum allowable daily dose of pegvaliase is 60 mg/day (for a maximum weekly dose of 420 mg). Duration between dose titration steps may be increased in response to AEs. Dose level reductions due to AEs or hypophenylalaninemia (blood Phe level of <30 μmon) may be made at any time during the study.

The duration of the Primary Treatment Phase (Part 1) is 73 weeks, during which pegvaliase treatment is initiated using an I/T/M dosing regimen. The recommended dosing schedule for all subjects dosing with pegvaliase in either Cohort A or B is shown in Table 3. Induction consists of a 4-week period when subjects receive pegvaliase subcutaneously with a PFS at a fixed dose of 2.5 mg/week and during which the dosing regimen is not modified in response to blood Phe concentration. Once subjects complete induction they titrate up to a dose of 10 mg/day. The dosing frequency is increased gradually during the titration phase to daily (7 days/week). During the maintenance phase the dose is increased to 20 mg/day, 40 mg/day, and 60 mg/day depending upon individual blood Phe lowering efficacy (per the investigator's discretion). The dose should be increased to 40 mg/day if blood Phe is >360 μmol/L after 24 weeks dosing at 20 mg/day and increased to 60 mg/day if blood Phe is >360 μmol/L after 16 weeks dosing at 40 mg/day. The target blood Phe levels should be based on individual needs, with a minimum target blood Phe<600 μmon.

Following completion of Part 1, subjects enter the Extension Phase (Part 2), during which subjects continue dosing with pegvaliase up to 60 mg/day for up to an additional 80 weeks in order to evaluate the long-term safety and efficacy of pegvaliase in adolescent subjects with PKU.

TABLE 3

Study Drug Dose Titration Schedule

| Part 1 Dosing Phase | Duration $^a$ | Dose (mg) | Frequency of Administration (Doses Per Week) |
|---|---|---|---|
| Induction | 4 weeks | 2.5 | 1 |
| Titration | 5 weeks | 2.5 | 2 |
|  |  | 10 | 1 |
|  |  | 10 | 2 |
|  |  | 10 | 4 |
|  |  | 10 | 7 |
| Maintenance | 64 weeks 20 mg daily | 20 | 7 |
|  | 16-24 weeks 40 mg daily 16 weeks $^b$ 60 mg daily 24 weeks $^b$ | 40 60 | 7 7 |

$^a$ Titration/dose escalation may be delayed depending on subject tolerability.
$^b$ All subjects begin maintenance at 20 mg daily. The dose is increased to 40 mg/day and/or 60 mg/day only if required.

Following enrollment, subjects (and a subject-designated caregiver) are trained to administer study drug at home. At a minimum, the first 3 study drug doses (Weeks 1, 2, and 3) are administered by the subject (or caregiver) in the clinic under clinic staff supervision. The subject (or caregiver) must demonstrate competency with injecting study drug in order to be permitted to administer study drug at home. During Part 1 of treatment (i.e., through Week 73), a competent adult (adult trained observer) must also be present during study drug administration and for a minimum of 1 hour following administration. Administration of study drug may only be performed if this adult observer is present. Subjects and the adult trained observers who are observing them during study drug administration are provided with information and extensive training regarding how to recognize a possible allergic reaction, the severity of the reaction, and instructions on what to do if a reaction occurs.

Requiring an adult trained observer for self-administered doses beyond the first 73 weeks of treatment may be considered as an option for an individual subject based on the investigator's clinical judgement. For example, an adult trained observer may be considered for subjects with intellectual disabilities, or for subjects who previously experienced anaphylaxis per National Institute of Allergy and Infectious Disease/Food Allergy and Anaphylaxis Network (NIAID/FAAN) criteria.

Subjects are provided with 2 epinephrine injectors and instructed to carry at least 1 epinephrine injector with them at all times. Subjects and adult trained observers are trained to recognize the signs and symptoms of anaphylaxis or acute systemic hypersensitivity reaction (ASHR) and, if these reactions occur, to call for emergency medical support and administer the epinephrine injector. For the duration of the study, each subject is contacted weekly by study site personnel to monitor for self-administration problems and adverse events (AEs).

All subjects receiving pegvaliase are pre-medicated with an H1 antagonist, and an H2 antagonist, and an antipyretic approximately 2 to 3 hours prior to each dose of study drug during the induction and titration phases. Pre-medication may be considered during the maintenance phase at the investigator's discretion. Pre-medication may also be administered, based on clinical judgement, approximately 2 to 3 hours prior to study drug for 1 week upon reintroduction of study drug, upon resolution of an AE, following any dose interruption of ≥4 days, and for any dose increases in the Extension Phase. Subjects may also be pre-medicated at any time in the study per investigator discretion. This premedication regimen was successfully implemented in the Phase 3 adult clinical program. Subjects are provided with a workbook to document the date and time of study drug injections, the injection site, pre-medications use, and suspected AEs.

If ≥4 doses are missed for reasons other than safety related issues, the investigator should consult with and obtain approval from the medical monitor prior to the subject restarting study drug.

Diet Monitoring. Subjects are asked to maintain stable dietary protein intake from medical food and/or intact food throughout the 73-week I/T/M Phase (Part 1). The ability of a subject to maintain stable protein intake is essential for the success of the study in order to ensure that the efficacy and safety endpoints are attributable to study treatment rather than changes in dietary protein intake. Subjects are required to maintain dietary protein intake levels that are consistent with their baseline levels for the entire duration of the study, with a consistent diet defined as one in which the intact protein changes are <10% from baseline and the medical food protein changes <10% from baseline.

A dietitian under investigator supervision is required to monitor and manage the subject's diet for the entire duration of the study. Subjects are provided with 3-day diaries in which all dietary protein intake (including medical food and/or intact food) must be recorded for 3 consecutive days immediately prior to each scheduled clinic visit for review with the dietitian. All subjects are provided the option of tyrosine supplementation (500 mg, 3 times per day with meals) at the discretion of the investigator.

In the Screening/Run-in Phase, 3-day diet diary assessments are to occur twice, 2 to 4 weeks apart. Subjects are instructed not to change their dietary protein intake (medical food and/or intact food) during the Screening/Run-in and Primary Treatment Phase (Part 1) of the study. However, modifications to a subject's diet and reductions in study drug dose level must be implemented if blood Phe levels are reduced to <30 µmol/L and confirmed upon recheck (performed within approximately 4 weeks).

Once subjects enter the Extension Phase (Part 2), dietary protein intake may be modified if blood Phe concentration is ≤360 µmol/L for a minimum of 4 weeks. Subjects with blood Phe measurements ≤360 µmol/L during Part 2 may adjust dietary protein intake based on individual subject response to pegvaliase and guidance from the investigator or designee.

If the dose level is reduced for a subject, reductions from 60 mg/day to 40 mg/day or from 40 mg/day to 20 mg/day pegvaliase are recommended. Reductions to intermediate doses may be allowed after discussion with the medical monitor. Dose reductions may be performed over the telephone or in the clinic. If diet is modified, it is recommended that intact protein be increased in 10 gm increments unless the subject is already consuming age appropriate protein levels (World Health Organization, Food and Agriculture Organization of the United Nations, 2007). Medical food may be discontinued once the dietitian determines that the essential amino acids meet age-appropriate levels.

Pregnancy. Because the risks of taking study drug during pregnancy and breastfeeding are unknown, subjects cannot take study drug if they are trying to conceive, are pregnant, or are breastfeeding. From Day -28 sexually active subjects must use 2 acceptable methods of contraception as outlined in the inclusion criteria section of this protocol. Subjects who are confirmed to be pregnant by a serum pregnancy test and are temporarily off study drug are not required to perform the scheduled urine pregnancy tests.

Subject Discontinuation. If study drug is discontinued before study completion, the investigator asks the subject to remain in the study to continue study visits and assessments. Subjects who discontinue from study drug early should continue to have study assessments performed for 30 days after discontinuation, as long as such continued participation does not detrimentally affect the health, safety, and welfare of the subject per investigator determination.

Safety Management Plan

An independent Data Monitoring Committee (DMC) monitors the safety of study subjects.

Response to Hypersensitivity Adverse Events. Subjects are evaluated for safety throughout the study and are trained to recognize potential hypersensitivity AEs (HAEs), including anaphylaxis or acute systemic hypersensitivity reaction (per NIAID/FAAN criteria), and how to respond. Subjects are instructed to contact the investigator for any suspected HAE. After a telephone assessment, the investigator may require further evaluation at the clinic. If a hypersensitivity reaction (eg, injection-site reaction, rash, joint pain, itching) occurs, the subject may be advised to pre-medicate with an H1 antagonist, and an H2 antagonist, and an antipyretic (eg, acetaminophen) approximately 2 to 3 hours prior to subsequent study drug doses. If nonsteroidal anti-inflammatory drugs (NSAIDs) are administered as a premedication, they should be given with food.

If a subject develops a severe or dermatologically significant skin reaction (or a reaction that could potentially be vasculitis) the subject should be referred for a dermatology consultation. A skin biopsy may be considered as part of the assessment of any such manifestation.

The occurrence of HAEs are expected with study drug administration. In response to a suspected HAE, study drug dosing may be modified or halted depending on the severity of the event and suspected study drug causality. Individual AEs per Medical Dictionary for Regulatory Activities (MedDRA) preferred term that are considered an HAE are defined consistent with the "Hypersensitivity Reaction" adverse drug reaction (ADR) definition. Severity of AEs (preferred term) related to HAEs are graded per National Cancer Institute—Common Terminology Criteria for Adverse Events (NCI-CTCAE) criteria.

Individual Stopping Criteria Evaluation for Adverse Events During Pegvaliase Treatment. Subjects who have an anaphylaxis related episode that is, in the judgment of the investigator and/or the sponsor's medical monitor, related to study drug and suspected to meet Brown's criteria for severe (Grade 3), are permanently discontinued from study drug.

Dosing in Response to Hypersensitivity Adverse Events. Dosing in response to a HAE depends on the NCI-CTCAE grade and suspected relationship to study drug. Dosing instructions are provided in Table 4 (regardless of previous occurrence).

TABLE 4

Dosing Instructions in Response to a Hypersensitivity Adverse Event

| NCI-CTCAE Grade [a] | Related to Study Drug | Action with Study Drug | | | Individual Stopping Criteria Evaluation [d] | HRV Assessment [e] |
|---|---|---|---|---|---|---|
| | | Maintain [b] | Reduce [c] | Interrupt [c] | | |
| 1 | Yes or No | X | (X) Optional | (X) Optional | | Investigator discretion |
| 2 | Yes or No | X | (X) Optional | (X) Optional | | Investigator discretion |
| 3 | No | | | | X Immediately consult with sponsor medical monitor | Investigator discretion |
| 3 | Yes | | | | X Immediately consult with sponsor medical monitor | Yes (if within 24 hours of onset) |
| 3 [d] | Yes | | | | X Immediately consult with sponsor medical monitor | Yes (if within 24 hours of onset) |

TABLE 4-continued

Dosing Instructions in Response to a Hypersensitivity Adverse Event

| NCI-CTCAE Grade [a] | Related to Study Drug | Action with Study Drug | | | Individual Stopping Criteria Evaluation [d] | HRV Assessment [e] |
|---|---|---|---|---|---|---|
| | | Maintain [b] | Reduce [c] | Interrupt [c] | | |
| 4 [d] | Yes or No | | | | X Immediately consult with sponsor medical monitor | Yes (if within 24 hours of onset) |

AE, adverse event; CTCAE, Common Terminology Criteria for Adverse Events, Version 5.0; HRV, Hypersensitivity Reaction Visit; NCI, National Cancer Institute.
[a] NCI-CTCAE grade determination is performed by the investigator and may be done either via telephone or clinic visit.
[b] The investigator instructs the subject to maintain the study drug dose at the time of AE onset until improvement to Grade 1 or resolution (per investigator assessment in the clinic or via telephone).
[c] The study drug dose may be reduced or interrupted if necessary per investigator determination.
[d] If a subject has an NCI-CTCAE Grade ≥ 3 hypersensitivity AE that is related to study drug and is suspected to meet Brown's criteria for severe (Grade 3) in the judgment of the investigator and/or the sponsor's medical monitor, the subject is permanently discontinued from study drug.
[e] If the investigator determines that the NCI-CTCAE Grade ≥ 3 hypersensitivity reaction is related to administration with study drug, the subject is asked to return to the clinic within 24 hours of event onset for evaluation, including laboratory tests (chemistry, hematology, urinalysis, anti-pegvaliase IgE [sampling should be performed 8 to 24 hours after event onset and before the next dose of study drug], urine albumin/creatinine ratio, CRP, C3, and C4).

Once an HAE (other than anaphylaxis) improves to Grade 1 or resolves, the study drug dose may be increased, maintained, or reduced, at the discretion of the investigator. If reduced, reductions should be from 60 to 40 mg/day, from 40 to 20 mg/day, or from 20 to 10 mg/day, whichever is appropriate.

Response to Anaphylaxis or Acute Systemic Hypersensitivity Reaction. If a subject experiences anaphylaxis or an acute systemic hypersensitivity reaction, they are instructed to inject epinephrine, to seek immediate medical attention, and to inform the investigator.

If the investigator suspects that an AE is anaphylaxis as defined by NIAID/FAAN, the subject is assessed in the clinic and the sponsor's medical monitor should be immediately notified. Laboratory assessments for suspected anaphylaxis events are performed prior to the next administration of study drug (if applicable) and include anti-pegvaliase IgE (for optimal results, sampling should be performed 8 to 24 hours after event onset). If the investigator determines it is safe for the subject to resume dosing with study drug following resolution of anaphylaxis at any time during the study, the following steps are required: at least the first dose administered after resolution of anaphylaxis is given at the clinic with equipment for emergency resuscitation (including epinephrine) within easy access; the subject must be pre-medicated with an H1 antagonist, and an H2 antagonist, and an antipyretic (eg, acetaminophen) approximately 2 to 3 hours prior to each dose of study drug for at least 1 week upon resumption of dosing, regardless of the duration of dose interruption; an adult trained observer must observe the subject during study drug administration and for a minimum of 1 hour following study drug administration for at least 1 week upon resumption of dosing, regardless of the duration of dose interruption; and administration of study drug may only be performed if this person is present.

Study Stopping Criteria Evaluation for Adverse Events During Treatment with Study Drug. If anaphylaxis or acute systemic hypersensitivity reaction meeting Brown's criteria for severe (Grade 3; Table 4) occurs, the DRB chair and/or committee is informed and advises the sponsor on potential changes to study conduct. Clinically severe hypersensitivity per Brown's criteria is defined as significant hypoxia, hypotension or neurologic compromise that is life-threatening or required treatment to prevent a life-threatening event: cyanosis or $SpO_2 \leq 92\%$; hypotension with SBP<90 mm Hg; neurologic alteration (e.g., confusion, loss of consciousness, collapse, and incontinence).

Numerous modifications and variations in the disclosure as set forth in the above illustrative examples are expected to occur to those skilled in the art. Consequently only such limitations as appear in the appended claims should be placed on the disclosure.

What is claimed:

1. A method for reducing blood phenylalanine concentration in a subject, comprising administering to the subject a weekly dose of a formulation comprising an AvPAL variant, wherein the subject is about 12 years old to about 17 years old, and wherein the weekly dose is administered for more than 50 weeks, wherein the AvPAL variant comprises the amino acid sequence of SEQ ID NO:2, SEQ ID NO:3 or SEQ ID NO:4.

2. The method of claim 1, wherein
   a. the weekly dose is administered for more than 60 weeks, more than 70 weeks, more than 80 weeks, more than 90 weeks, more than 100 weeks, more than 110 weeks, more than 120 weeks, more than 130 weeks, more than 140 weeks, more than 150 weeks, more than 160 weeks, more than 170 weeks, more than 180 weeks, more than 190 weeks, more than 200 weeks, more than 210 weeks, more than 220 weeks, more than 230 weeks, more than 240 weeks, or more than 250 weeks; and/or
   b. the dosage is in the range of about 0.1 mg per week to about 1 mg per week, about 1 mg per week to about 2 mg per week, about 2 mg per week to about 10 mg per week, about 10 mg per week to about 20 mg per week, about 20 mg per week to about 40 mg per week, about 40 mg per week to about 70 mg per week, about 70 mg per week to about 140 mg per week, about 140 mg per week to about 280 mg per week, about 280 mg per week to about 420 mg per week, or about 420 mg per week to about 840 mg per week.

3. The method of claim 1, wherein the AvPAL variant is administered once weekly, twice weekly, four times per week, seven times per week, fourteen times per week, or daily.

4. The method of claim 1, wherein the method comprises:
   a. administering to the subject the AvPAL variant at an induction dosage in the range of about 0.1 mg per week to about 10 mg per week, followed by
   b. administering to the subject the AvPAL variant at a titration dosage in the range of about 1 mg per week to about 200 mg per week, followed by
   c. administering to the subject the AvPAL variant at a maintenance dosage in the range of about 20 mg per week to about 840 mg per week.

5. The method of claim 4, wherein
   a. the induction dosage is about 2.5 mg per week;
   b. the titration dosage is in the range of about 5 mg per week to about 70 mg per week; and/or
   c. the maintenance dosage is in the range of about 140 mg per week to about 420 mg per week.

6. The method of claim 4, wherein the induction dosage is administered for a duration of between 2 weeks and 6 weeks, the titration dosage is administered for a duration of between 3 weeks and 8 weeks, and the maintenance dosage is administered for a duration of between 50 weeks and 80 weeks; wherein optionally
   a. the induction dosage is administered for a duration of about 4 weeks, the titration dosage is administered for a duration of about 5 weeks, and the maintenance dosage is administered for a duration of between 56 weeks and 64 weeks; or
   b. the maintenance dosage is comprised of a first maintenance dosage of between 70 mg per week and 280 mg per week, a second maintenance dosage of between 140 mg per week and 560 mg per week, and a third maintenance dosage of between 210 mg per week and 840 mg per week; wherein optionally the first maintenance dosage is administered for a duration of between 16 weeks and 24 weeks, the second maintenance dosage is administered for a duration of about 16 weeks, and the third maintenance dosage is administered for a duration of about 24 weeks.

7. The method of claim 4, wherein following the administration of the maintenance dosage, the method further comprises administering to a subject the AvPAL variant an extension dosage in the range of about 20 mg per week to about 840 mg per week.

8. The method of claim 4, wherein the method further comprises assessing the blood phenylalanine concentration
   a. prior to administering the induction dosage; and/or
   b. after administration of one or more induction dosages, titration dosages, maintenance dosages, and/or extension dosages.

9. The method of claim 8, wherein the method further comprises adjusting the dosage based on the blood phenylalanine concentration; wherein optionally the dosage is adjusted to attain a blood phenylalanine concentration of
   a. below 600 µM; wherein optionally the maintenance dosage is increased if blood phenylalanine concentration is greater than 360 µM; or
   b. below 360 µM.

10. The method of claim 1, wherein the subject has phenylketonuria (PKU); wherein the subject is between 12 years old and 15 years old, or between 16 years old and 17 years old.

11. The method of claim 1, wherein the AvPAL variant comprises the amino acid sequence of SEQ ID NO:2, SEQ ID NO:3, or SEQ ID NO:4.

12. The method of claim 1, wherein the AvPAL variant is pegylated.

13. The method of claim 1, wherein the AvPAL variant is administered as a formulation comprising a pharmaceutically acceptable carrier comprising a stabilizer; wherein optionally
   a. the stabilizer is L-phenylalanine or structural analog thereof;
   b. the stabilizer is selected from the group consisting of L-phenylalanine, trans-cinnamic acid and benzoic acid;
   c. the stabilizer is trans-cinnamic acid; and/or
   d. the formulation further comprises sodium chloride, and tromethamine and tromethamine hydrochloride.

14. The method of claim 7, wherein the extension dosage is administered for a duration of between 40 weeks and 120 weeks.

15. The method of claim 14, wherein the induction dosage is administered for a duration of about 4 weeks, the titration dosage is administered for a duration of about 5 weeks, the maintenance dosage is administered for a duration of about 64 weeks, and the extension dosage is administered for a duration of about 80 weeks.

16. The method of claim 12, wherein said pegylation is achieved by reacting the AvPAL variant with NETS-activated polyethylene glycol at a ratio of at least 1.6 polyethylene glycol per lysine residue of AvPAL variant, at a ratio of at least 2.4 polyethylene glycol per lysine residue of AvPAL variant, at a ratio of 3 polyethylene glycol per lysine residue of AvPAL variant, at a ratio of 5 polyethylene glycol per lysine residue of AvPAL variant, at a ratio of 6 polyethylene glycol per lysine residue of AvPAL variant, at a ratio of 7 polyethylene glycol per lysine residue of AvPAL variant, at a ratio of 8 polyethylene glycol per lysine residue of AvPAL variant, or at a ratio of 9 polyethylene glycol per lysine residue of AvPAL variant.

\* \* \* \* \*

UNITED STATES PATENT AND TRADEMARK OFFICE
CERTIFICATE OF CORRECTION

PATENT NO. : 11,918,633 B2
APPLICATION NO. : 17/747697
DATED : March 5, 2024
INVENTOR(S) : Debra Lounsbury It is certified that error appears in the above-identified patent and that said Letters Patent is hereby corrected as shown below:

In the Claims

Claim 16:
Column 70, Line 42, "NETS-acti-" should read -- NHS-acti- --.

Signed and Sealed this
Fourth Day of June, 2024

Katherine Kelly Vidal
Director of the United States Patent and Trademark Office